US012790383B2

(12) United States Patent
Shen et al.

(10) Patent No.: US 12,790,383 B2
(45) Date of Patent: Nov. 10, 2026

(54) GENETICALLY MODIFIED NON-HUMAN ANIMAL EXPRESSING A B2M/FCRN FUSION PROTEIN

(71) Applicant: Biocytogen Pharmaceuticals (Beijing) Co., Ltd., Beijing (CN)

(72) Inventors: Yuelei Shen, Beijing (CN); Jiawei Yao, Beijing (CN); Yanan Guo, Beijing (CN); Yang Bai, Beijing (CN); Chengzhang Shang, Beijing (CN)

(73) Assignee: Biocytogen Pharmaceuticals (Beijing) Co., Ltd., Beijing (CN)

(*) Notice: Subject to any disclaimer, the term of this patent is extended or adjusted under 35 U.S.C. 154(b) by 944 days.

(21) Appl. No.: 18/010,964

(22) PCT Filed: Jun. 18, 2021

(86) PCT No.: PCT/CN2021/100958

§ 371 (c)(1),
(2) Date: Dec. 16, 2022

(87) PCT Pub. No.: WO2021/254491

PCT Pub. Date: Dec. 23, 2021

(65) Prior Publication Data

US 2023/0227531 A1 Jul. 20, 2023

(30) Foreign Application Priority Data

Jun. 19, 2020 (CN) ........................ 202010568508.7

(51) Int. Cl.

| | |
|---|---|
| ***C07K 14/705*** | (2006.01) |
| ***A01K 67/0275*** | (2024.01) |
| ***A61K 49/00*** | (2006.01) |
| ***C12N 9/22*** | (2006.01) |
| ***C12N 15/62*** | (2006.01) |
| ***C12N 15/85*** | (2006.01) |
| ***C12N 15/90*** | (2006.01) |

(52) U.S. Cl.

CPC .... *C07K 14/70539* (2013.01); *A01K 67/0275* (2013.01); *A61K 49/0008* (2013.01); *C07K 14/70535* (2013.01); *C12N 9/22* (2013.01); *C12N 15/62* (2013.01); *C12N 15/8509* (2013.01); *C12N 15/907* (2013.01); *A01K 2207/12* (2013.01); *A01K 2217/072* (2013.01); *A01K 2217/15* (2013.01); *A01K 2227/105* (2013.01); *A01K 2267/0325* (2013.01); *A01K 2267/0387* (2013.01); *C07K 2319/02* (2013.01); *C07K 2319/30* (2013.01); *C12N 2310/20* (2017.05); *C12N 2800/107* (2013.01)

(58) Field of Classification Search

CPC ............ A01K 2207/15; C07K 2319/00; C07K 14/70539

See application file for complete search history.

(56) References Cited

U.S. PATENT DOCUMENTS

| | | | |
|---|---|---|---|
| 6,911,321 B2 | 6/2005 | Presta et al. | |
| 6,992,234 B2 | 1/2006 | Roopenian | |
| 7,358,416 B2 | 4/2008 | Roopenian | |
| 10,820,580 B2 | 11/2020 | Shen et al. | |
| 11,576,984 B2 | 2/2023 | Voronina et al. | |
| 2015/0106961 A1 | 4/2015 | Rojas et al. | |
| 2018/0015185 A1 | 1/2018 | MacDonald et al. | |
| 2018/0282392 A1* | 10/2018 | Seidel, III | A61P 31/12 |
| 2019/0113519 A1* | 4/2019 | Cameron | C07K 14/70535 |
| 2019/0320631 A1 | 10/2019 | Shen et al. | |
| 2024/0081301 A1 | 3/2024 | Shang et al. | |

FOREIGN PATENT DOCUMENTS

| | | |
|---|---|---|
| CN | 101595128 | 12/2009 |
| CN | 107567460 | 1/2018 |
| CN | 110055223 | 7/2019 |
| CN | 111073907 | 4/2020 |
| CN | 111118019 | 5/2020 |
| CN | 111172190 | 5/2020 |
| CN | 113429486 | 9/2021 |
| WO | WO 2015/157415 A1 | 10/2015 |
| WO | WO 2018/001241 | 1/2018 |
| WO | WO 2018/041118 | 3/2018 |
| WO | WO 2018/041119 | 3/2018 |
| WO | WO 2018/041120 | 3/2018 |
| WO | WO 2018/041121 | 3/2018 |
| WO | WO 2018/068756 | 4/2018 |
| WO | WO 2018/086583 | 5/2018 |
| WO | WO 2018/086594 | 5/2018 |

(Continued)

OTHER PUBLICATIONS

Li Q, Qin Z, Wang Q, Xu T, Yang Y, He Z. Applications of Genome Editing Technology in Animal Disease Modeling and Gene Therapy. Comput Struct Biotechnol J. Jun. 8, 2019;17:689-698. doi: 10.1016/j.csbj.2019.05.006. PMID: 31303973; PMCID: PMC6603303. (Year: 2019).*

Lee H, Yoon DE, Kim K. Genome editing methods in animal models. Anim Cells Syst (Seoul). Feb. 17, 2020;24(1):8-16. doi: 10.1080/19768354.2020.1726462. PMID: 32158611; PMCID: PMC7048190. (Year: 2020).*

Sato K, Sasaki E. Genetic engineering in nonhuman primates for human disease modeling. J Hum Genet. Feb. 2018;63(2):125-131. doi: 10.1038/s10038-017-0351-5. Epub Dec. 4, 2017. PMID: 29203824; PMCID: PMC8075926. (Year: 2018).*

Sander JD, Joung JK. CRISPR-Cas systems for editing, regulating and targeting genomes. Nat Biotechnol. Apr. 2014;32(4):347-55. doi: 10.1038/nbt.2842. Epub Mar. 2, 2014. PMID: 24584096; PMCID: PMC4022601. (Year: 2014).*

(Continued)

*Primary Examiner* — Fereydoun G Sajjadi
*Assistant Examiner* — Qinhua Gu
(74) *Attorney, Agent, or Firm* — Fish & Richardson P.C.

(57) ABSTRACT

The present disclosure relates to genetically modified non-human animals that express a fusion protein including B2M and FcRn, and methods of use thereof. In some embodiments, the animals can have a B-NDG background. In some embodiments, the endogenous B2M gene is knocked out in the animals.

17 Claims, 12 Drawing Sheets

Specification includes a Sequence Listing.

(56) References Cited

FOREIGN PATENT DOCUMENTS

| | | |
|---|---|---|
| WO | WO 2018/121787 | 7/2018 |
| WO | WO 2018/177440 | 10/2018 |
| WO | WO 2018/177441 | 10/2018 |
| WO | WO 2021195574 A1 | 9/2021 |

OTHER PUBLICATIONS

Brehm MA, Shultz LD. Lack of acute xenogeneic graft-versus-host disease, but retention of T-cell function following engraftment of human peripheral blood mononuclear cells in NSG mice deficient in MHC class I and II expression. FASEB J. Mar. 2019;33(3):3137-3151. (Year: 2019).*

Viuff D, Antunes F, Howard KA. Generation of a double transgenic humanized neonatal Fc receptor (FcRn)/albumin mouse to study the pharmacokinetics of albumin-linked drugs. J Control Release. Feb. 10, 2016;223:22-30. (Year: 2016).*

Auerbach et al., "Establishment and chimera analysis of 129/SvEv- and C57BL/6-derived mouse embryonic stem cell lines," Biotechniques, Nov. 2000, 29(5):1024-1032.

Avery et al., "Utility of a human FcRn transgenic mouse model in drug discovery for early assessment and prediction of human pharmacokinetics of monoclonal antibodies," InMAbs, Aug. 17, 2016, 8(6): 16 pages.

Feng et al., "Design, expression and characterization of a soluble single-chain functional human neonatal Fc receptor," Protein expression and purification, Sep. 1, 2011, 79(1): 14 pages.

Festing et al., "Revised nomenclature for strain 129 mice," Mammalian Genome, Aug. 1, 1999, 10(8):836.

GenBank Accession No., NC_000073.6, "Mus musculus strain C57BL/6J chromosome 7, GRCm38.p4 C57BL/6J," Jun. 22, 2016, 2 pages.

GenBank Accession No. NC_000068.7, "Mus musculus strain C57BL/6J chromosome 2, GRCm38.p4 C57BL/6J," Jun. 22, 2016, 2pages.

GenBank Accession No. NM_009735.3, "Mus musculus beta-2 microglobulin (B2m), mRNA," May 28, 2019, 3 pages.

GenBank Accession No. NM_010189.3, "Mus musculus Fc receptor, IgG, alpha chain transporter (Fcgrt), transcript variant 1, mRNA," Jun. 4, 2019, 5 pages.

GenBank Accession No. NP_033865.2, "beta-2-microglobulin precursor [Mus musculus], " May 28, 2019, 3 pages.

GenBank Accession No. NP_034319.2, "IgG receptor FcRn large subunit p51 isoform 1 precursor [Mus musculus]," Jun. 4, 2019, 4 pages.

International Preliminary Report on Patentability in International Appln. No. PCT/CN2021/100958, mailed on Dec. 29, 2022, 7 pages.

International Search Report and Written Opinion in International Appln. No. PCT/CN2021/100958, mailed on Sep. 22, 2021, 12 pages.

Ishikawa et al., "Development of functional human blood and immune systems in NOD/SCID/IL2 receptor γ chainnull mice," Blood, Sep. 1, 2005, 106(5):1565-1573.

Ito et al., "Current advances in humanized mouse models," Cellular & molecular immunology, May 2012, 9(3):208-214.

Katano et al., "NOD-Rag2null IL-2Rγnull mice: an alternative to NOG mice for generation of humanized mice," Experimental animals, 2014, 63(3):321-330.

Li et al., "The implication and significance of beta 2 microglobulin: a conservative multifunctional regulator," Chinese medical journal, Feb. 20, 2016, 129(04):448-455.

Proetzel et al., "Humanized FcRn mouse models for evaluating pharmacokinetics of human IgG antibodies," Methods, Jan. 1, 2014, 65(1): 15 pages.

Pyzik et al., "FcRn: the architect behind the immune and nonimmune functions of IgG and albumin," The Journal of Immunology, May 15, 2015, 194(10): 10 pages.

Pyzik et al., "The neonatal Fc receptor (FcRn): a misnomer?" Frontiers in immunology, 2019, 10(1540): 24 pages.

UniProt Accession No. Q61559, "IgG receptor FcRn large subunit p51," Jun. 5, 2019.

Wang et al., "Targeted disruption of the β 2-microglobulin gene minimizes the immunogenicity of human embryonic stem cells," Stem cells translational medicine, Oct. 2015, 4(10): 13 pages.

Yin et al., "Delivery technologies for genome editing," Nature reviews Drug discovery, Jun. 2017, 16(6):387-399.

GenBank Accession No. NC_000019.10, "*Homo sapiens* chromosome 19, GRCh38.p13 Primary Assembly," Dec. 9, 2019, 3 pages.

GenBank Accession No. NM_004107.5, "*Homo sapiens* Fc gamma receptor and transporter (FCGRT), transcript variant 2, mRNA," Nov. 5, 2019, 5 pages.

GenBank Accession No. NP_004098.1, "IgG receptor FcRn large subunit p51 isoform 1 precursor [*Homo sapiens*]," Nov. 5, 2019, 4 pages.

International Preliminary Report on Patentability in International Appln. No. PCT/CN2022/075057, mailed on Aug. 3, 2023, 5 pages.

International Search Report and Written Opinion in International Appln. No. PCT/CN2022/075057, mailed on Apr. 27, 2022, 10 pages.

Ito et al., "NOD/SCID/ γcnull mouse: an excellent recipient mouse model for engraftment of human cells," Blood, 2002, 100(9):3175-3182.

Kuo et al., "Neonatal Fc receptor and IgG-based therapeutics," mAbs, 2011,3(5):422-430.

Liu et al., "An Omalizumab biobetter antibody with improved stability and efficacy for the treatment of allergic diseases," Frontiers in Immunology, Nov. 2020, 11(596908):1-15.

Martins et al., "A comprehensive review of the neonatal Fc receptor and its application in drug delivery," Pharmacology & Therapeutics, 2016, 161:22-39.

Petkova et al., "Enhanced half-life of genetically engineered human IgG1 antibodies in a humanized FcRn mouse model: potential application in humorally mediated autoimmune disease," International Immunology, 2006, 18(12):1759-1769.

UniProt Accession No. P55899, "IgG receptor FcRn large subunit p51," Dec. 11, 2019, 7 pages.

Extended European Search Report in European Appln. No. 22749179.2, mailed on Dec. 16, 2024, 9 pages.

Viuff et al., "Generation of a double transgenic humanized neonatal Fc receptor (FcRn)/albumin mouse to study the pharmacokinetics of albumin-linked drugs," J Control Release, Feb. 10, 2016, available online Dec. 14, 2015, 223:22-30.

Chaudhury et al., "The Major Histocompatibility Complex-Related Fc Receptor for IgG (FcRn) Binds Albumin and Prolongs Its Lifespan," J Exp Med., Feb. 3, 2003, 197(3):315-322.

Mikulska et al., "Cloning and Analysis of the Gene Encoding the Human Neonatal Fc Receptor," Eur J Immunogenet., Aug. 2000, 27(4):231-240 (28 pages in total).

R&D Systems, Inc. (Bio-Techne Corporation), "Recombinant Mouse FcRn Protein, CF (Catalog No. 6775-FC) Product Data Sheet / Background Information," R&D Systems, 2018, 1 page.

* cited by examiner

SEQUENCE LISTING

```
<160> NUMBER OF SEQ ID NOS: 47

<210> SEQ ID NO 1
<211> LENGTH: 858
<212> TYPE: DNA
<213> ORGANISM: Mus musculus

<400> SEQUENCE: 1

tttcagtggc tgctactcgg cgcttcagtc gcggtcgctt cagtcgtcag catggctcgc     60

tcggtgaccc tggtctttct ggtgcttgtc tcactgaccg gcctgtatgc tatccagaaa    120

acccctcaaa ttcaagtata ctcacgccac ccaccggaga atgggaagcc gaacatactg    180

aactgctacg taacacagtt ccacccgcct cacattgaaa tccaaatgct gaagaacggg    240

aaaaaaattc ctaaagtaga gatgtcagat atgtccttca gcaaggactg gtctttctat    300

atcctggctc acactgaatt caccccact gagactgata catacgcctg cagagttaag     360

catgccagta tggccgagcc caagaccgtc tactgggatc gagacatgtg atcaagcatc    420

atgatgctct gaagattcat ttgaacctgc ttaattacaa atccagtttc taatatgcta    480

tacaatttat gcacgcagaa agaaatagca atgtacacat caccttcttt atatcttact    540

ttaaatattt tatgcatgtt ttcaaaaaat tggaaatatc ctagatagct gagcaataaa    600

tcttcaataa gtattttgat cagaataata aatataattt taagaacaat agttgatcat    660

atgccaaacc ctctgtactt ctcattactt ggatgcagtt actcatcttt ggtctatcac    720

aacataagtg acatactttc cttttggtaa agcaaagagg cctaattgaa gtctgtcact    780

gtgcccaatg cttagcaatt ctcaccccca accctgtggc tacttctgct tttgttactt    840

ttactaaaaa taaaaaac                                                   858


<210> SEQ ID NO 2
<211> LENGTH: 119
<212> TYPE: PRT
<213> ORGANISM: Mus musculus

<400> SEQUENCE: 2

Met Ala Arg Ser Val Thr Leu Val Phe Leu Val Leu Val Ser Leu Thr
1               5                   10                  15

Gly Leu Tyr Ala Ile Gln Lys Thr Pro Gln Ile Gln Val Tyr Ser Arg
            20                  25                  30

His Pro Pro Glu Asn Gly Lys Pro Asn Ile Leu Asn Cys Tyr Val Thr
        35                  40                  45

Gln Phe His Pro Pro His Ile Glu Ile Gln Met Leu Lys Asn Gly Lys
    50                  55                  60

Lys Ile Pro Lys Val Glu Met Ser Asp Met Ser Phe Ser Lys Asp Trp
65                  70                  75                  80
```

```
Ser Phe Tyr Ile Leu Ala His Thr Glu Phe Thr Pro Thr Glu Thr Asp
                85                  90                  95

Thr Tyr Ala Cys Arg Val Lys His Ala Ser Met Ala Glu Pro Lys Thr
            100                 105                 110

Val Tyr Trp Asp Arg Asp Met
        115


<210> SEQ ID NO 3
<211> LENGTH: 1738
<212> TYPE: DNA
<213> ORGANISM: Mus musculus

<400> SEQUENCE: 3

aggagctagt gggtggagtt ggatgccctc agagttctcc agtcctaact gtgtacagac     60

aggatgtaag agaagaactg gaggctctaa gcagaggatc catcggctgc aggcagaggg    120

aagagggcct ctgtgaggaa caggctgagc gtcagaggag gaggcccagg cctggttctc    180

tagctctgta attaattaac taaagtggat caaatgagaa ggtgaaagtt cacagaggaa    240

cactcctgtc tgtcgtcttg gactgggtct ccatccccacc atccagcgtc ctggtctacg    300

aagagtccac agggaccttg tgaagaatca acaaggcggg gtccagagga gtcacgtgtc    360

ccttccactc cgggtcaccc tgtcggaatg gggatgccac tgccctgggc cctcagcctc    420

ttgttggtcc tcctgcctca gacctggggc tcagagaccc gcccccccact gatgtatcat    480

ctcacggctg tgtcaaaccc atctacgggg cttccctctt tctgggctac aggctggttg    540

ggtcctcagc agtatctgac ctacaacagc ctgcggcagg aagctgaccc ctgtggggcc    600

tggatgtggg aaaatcaggt gtcttggtat tgggagaagg agaccacaga cctcaaaagc    660

aaagaacagc tcttcttgga ggccctcaag accctggaga agatattaaa tgggacctac    720

acactgcagg gcctgctggg ctgtgaactg gcctcggata attcctcagt gcccacggct    780

gtgtttgccc tcaatggtga ggagtttatg aaattcaacc caagaatcgg caattggact    840

ggggagtggc ctgagacgga aatcgttgct aatctgtgga tgaagcagcc tgatgcggcc    900

aggaaggaga gcgagttcct gctaaactct tgtccggagc gactgctagg ccacctggag    960

aggggccgac ggaacctgga gtggaaggag ccgccgtcta tgcgcctgaa ggcccgtcct   1020

ggcaactctg gctcctccgt gctgacctgt gctgctttct ccttctaccc accggagctc   1080

aagttccgat tcctgcgcaa tgggctagcc tcaggctccg ggaattgcag cactggtccc   1140

aatggagatg gctctttcca cgcatggtca ttgctggagg tcaaacgtgg agatgagcac   1200

cattatcaat gtcaagtgga gcatgagggg ctggcacagc ctctcactgt ggacctagat   1260

tcatcagcca gatcttctgt gcctgtggtt ggaatcgttc ttggtttatt gctggtggta   1320

gtggccatcg caggcggtgt gctgttgtgg ggcaggatgc gcagcggtct gccagcccca   1380

tggctttctc tcagcggcga tgactctggt gacctgttgc ctggtgggaa cttgcccccca   1440

gaagctgaac ctcaaggtgc aaatgccttt ccagccactt cctgatgcag actcgggccc   1500

cctgcccact gcagcctttc gggctgtgtg acctcctgaa ctgtctccga gcctcctgag   1560

ggagcctggg cccgatgtcc tcccatggat ccctgctttt gtggcctgct tcagtttccc   1620

ttcttaatgt acatggttgt tttccatctc cacataaatt tggccccaaa tctgtgtgtg   1680

catcgttatt ctcaagtttc aagcagctgg aataaattga acgcgtctgg gaaagatc      1738


<210> SEQ ID NO 4
<211> LENGTH: 365
```

<212> TYPE: PRT
<213> ORGANISM: Mus musculus

<400> SEQUENCE: 4

```
Met Gly Met Pro Leu Pro Trp Ala Leu Ser Leu Leu Leu Val Leu Leu
1               5                   10                  15

Pro Gln Thr Trp Gly Ser Glu Thr Arg Pro Pro Leu Met Tyr His Leu
            20                  25                  30

Thr Ala Val Ser Asn Pro Ser Thr Gly Leu Pro Ser Phe Trp Ala Thr
        35                  40                  45

Gly Trp Leu Gly Pro Gln Gln Tyr Leu Thr Tyr Asn Ser Leu Arg Gln
    50                  55                  60

Glu Ala Asp Pro Cys Gly Ala Trp Met Trp Glu Asn Gln Val Ser Trp
65                  70                  75                  80

Tyr Trp Glu Lys Glu Thr Thr Asp Leu Lys Ser Lys Glu Gln Leu Phe
                85                  90                  95

Leu Glu Ala Leu Lys Thr Leu Glu Lys Ile Leu Asn Gly Thr Tyr Thr
            100                 105                 110

Leu Gln Gly Leu Leu Gly Cys Glu Leu Ala Ser Asp Asn Ser Ser Val
        115                 120                 125

Pro Thr Ala Val Phe Ala Leu Asn Gly Glu Glu Phe Met Lys Phe Asn
    130                 135                 140

Pro Arg Ile Gly Asn Trp Thr Gly Glu Trp Pro Glu Thr Glu Ile Val
145                 150                 155                 160

Ala Asn Leu Trp Met Lys Gln Pro Asp Ala Ala Arg Lys Glu Ser Glu
                165                 170                 175

Phe Leu Leu Asn Ser Cys Pro Glu Arg Leu Leu Gly His Leu Glu Arg
            180                 185                 190

Gly Arg Arg Asn Leu Glu Trp Lys Glu Pro Pro Ser Met Arg Leu Lys
        195                 200                 205

Ala Arg Pro Gly Asn Ser Gly Ser Ser Val Leu Thr Cys Ala Ala Phe
    210                 215                 220

Ser Phe Tyr Pro Pro Glu Leu Lys Phe Arg Phe Leu Arg Asn Gly Leu
225                 230                 235                 240

Ala Ser Gly Ser Gly Asn Cys Ser Thr Gly Pro Asn Gly Asp Gly Ser
                245                 250                 255

Phe His Ala Trp Ser Leu Leu Glu Val Lys Arg Gly Asp Glu His His
            260                 265                 270

Tyr Gln Cys Gln Val Glu His Glu Gly Leu Ala Gln Pro Leu Thr Val
        275                 280                 285

Asp Leu Asp Ser Ser Ala Arg Ser Ser Val Pro Val Val Gly Ile Val
    290                 295                 300

Leu Gly Leu Leu Leu Val Val Val Ala Ile Ala Gly Gly Val Leu Leu
305                 310                 315                 320

Trp Gly Arg Met Arg Ser Gly Leu Pro Ala Pro Trp Leu Ser Leu Ser
                325                 330                 335

Gly Asp Asp Ser Gly Asp Leu Leu Pro Gly Gly Asn Leu Pro Pro Glu
            340                 345                 350

Ala Glu Pro Gln Gly Ala Asn Ala Phe Pro Ala Thr Ser
        355                 360                 365
```

<210> SEQ ID NO 5
<211> LENGTH: 2080
<212> TYPE: DNA
<213> ORGANISM: Artificial Sequence -continued
<220> FEATURE:
<223> OTHER INFORMATION: modified FcRn mRNA

<400> SEQUENCE: 5
aggagctagt gggtggagtt ggatgccctc agagttctcc agtcctaact gtgtacagac 60
aggatgtaag agaagaactg gaggctctaa gcagaggatc catcggctgc aggcagaggg 120
aagagggcct ctgtgaggaa caggctgagc gtcagaggag gaggcccagg cctggttctc 180
tagctctgta attaattaac taaagtggat caaatgagaa ggtgaaagtt cacagaggaa 240
cactcctgtc tgtcgtcttg gactgggtct ccatcccacc atccagcgtc ctggtctacg 300
aagagtccac agggaccttg tgaagaatca acaaggcggg gtccagagga gtcacgtgtc 360
ccttccactc cgggtcaccc tgtcggaatg gggatgccac tgccctgggc cctcagcctc 420
ttgttggtcc tcctgcctca gacctggggc atccagaaaa cccctcaaat tcaagtatac 480
tcacgccacc caccggagaa tgggaagccg aacatactga actgctacgt aacacagttc 540
cacccgcctc acattgaaat ccaaatgctg aagaacggga aaaaaattcc taaagtagag 600
atgtcagata tgtccttcag caaggactgg tctttctata tcctggctca cactgaattc 660
acccccactg agactgatac atacgcctgc agagttaagc atgccagtat ggccgagccc 720
aagaccgtct actgggatcg agacatggga ggtggcggat ccggcggagg cggctcgggt 780
ggcggcggct cttcagagac ccgcccccca ctgatgtatc atctcacggc tgtgtcaaac 840
ccatctacgg ggcttccctc tttctgggct acaggctggt tgggtcctca gcagtatctg 900
acctacaaca gcctgcggca ggaagctgac ccctgtgggg cctggatgtg ggaaaatcag 960
gtgtcttggt attgggagaa ggagaccaca gacctcaaaa gcaaagaaca gctcttcttg 1020
gaggccctca agaccctgga gaagatatta aatgggacct acacactgca gggcctgctg 1080
ggctgtgaac tggcctcgga taattcctca gtgcccacgg ctgtgtttgc cctcaatggt 1140
gaggagttta tgaaattcaa cccaagaatc ggcaattgga ctggggagtg gcctgagacg 1200
gaaatcgttg ctaatctgtg gatgaagcag cctgatgcgg ccaggaagga gagcgagttc 1260
ctgctaaact cttgtccgga gcgactgcta ggccacctgg agaggggccg acggaacctg 1320
gagtggaagg agccgccgtc tatgcgcctg aaggcccgtc ctggcaactc tggctcctcc 1380
gtgctgacct gtgctgcttt ctccttctac ccaccggagc tcaagttccg attcctgcgc 1440
aatgggctag cctcaggctc cgggaattgc agcactggtc ccaatggaga tggctctttc 1500
cacgcatggt cattgctgga ggtcaaacgt ggagatgagc accattatca atgtcaagtg 1560
gagcatgagg ggctggcaca gcctctcact gtggacctag attcatcagc cagatcttct 1620
gtgcctgtgg ttggaatcgt tcttggttta ttgctggtgg tagtggccat cgcaggcggt 1680
gtgctgttgt ggggcaggat gcgcagcggt ctgccagccc catggctttc tctcagcggc 1740
gatgactctg gtgacctgtt gcctggtggg aacttgcccc cagaagctga acctcaaggt 1800
gcaaatgcct ttccagccac ttcctgatgc agactcgggc cccctgccca ctgcagcctt 1860
tcgggctgtg tgacctcctg aactgtctcc gagcctcctg agggagcctg ggcccgatgt 1920
cctcccatgg atccctgctt ttgtggcctg cttcagtttc ccttcttaat gtacatggtt 1980
gttttccatc tccacataaa tttggcccca aatctgtgtg tgcatcgtta ttctcaagtt 2040
tcaagcagct ggaataaatt gaacgcgtct gggaaagatc 2080

<210> SEQ ID NO 6
<211> LENGTH: 479
<212> TYPE: PRT

```
<213> ORGANISM: Artificial Sequence
<220> FEATURE:
<223> OTHER INFORMATION: modified FcRn protein

<400> SEQUENCE: 6

Met Gly Met Pro Leu Pro Trp Ala Leu Ser Leu Leu Leu Val Leu Leu
1               5                   10                  15

Pro Gln Thr Trp Gly Ile Gln Lys Thr Pro Gln Ile Gln Val Tyr Ser
            20                  25                  30

Arg His Pro Pro Glu Asn Gly Lys Pro Asn Ile Leu Asn Cys Tyr Val
        35                  40                  45

Thr Gln Phe His Pro Pro His Ile Glu Ile Gln Met Leu Lys Asn Gly
    50                  55                  60

Lys Lys Ile Pro Lys Val Glu Met Ser Asp Met Ser Phe Ser Lys Asp
65                  70                  75                  80

Trp Ser Phe Tyr Ile Leu Ala His Thr Glu Phe Thr Pro Thr Glu Thr
                85                  90                  95

Asp Thr Tyr Ala Cys Arg Val Lys His Ala Ser Met Ala Glu Pro Lys
            100                 105                 110

Thr Val Tyr Trp Asp Arg Asp Met Gly Gly Gly Gly Ser Gly Gly Gly
        115                 120                 125

Gly Ser Gly Gly Gly Gly Ser Ser Glu Thr Arg Pro Pro Leu Met Tyr
    130                 135                 140

His Leu Thr Ala Val Ser Asn Pro Ser Thr Gly Leu Pro Ser Phe Trp
145                 150                 155                 160

Ala Thr Gly Trp Leu Gly Pro Gln Gln Tyr Leu Thr Tyr Asn Ser Leu
                165                 170                 175

Arg Gln Glu Ala Asp Pro Cys Gly Ala Trp Met Trp Glu Asn Gln Val
            180                 185                 190

Ser Trp Tyr Trp Glu Lys Glu Thr Thr Asp Leu Lys Ser Lys Glu Gln
        195                 200                 205

Leu Phe Leu Glu Ala Leu Lys Thr Leu Glu Lys Ile Leu Asn Gly Thr
    210                 215                 220

Tyr Thr Leu Gln Gly Leu Leu Gly Cys Glu Leu Ala Ser Asp Asn Ser
225                 230                 235                 240

Ser Val Pro Thr Ala Val Phe Ala Leu Asn Gly Glu Glu Phe Met Lys
                245                 250                 255

Phe Asn Pro Arg Ile Gly Asn Trp Thr Gly Glu Trp Pro Glu Thr Glu
            260                 265                 270

Ile Val Ala Asn Leu Trp Met Lys Gln Pro Asp Ala Ala Arg Lys Glu
        275                 280                 285

Ser Glu Phe Leu Leu Asn Ser Cys Pro Glu Arg Leu Leu Gly His Leu
    290                 295                 300

Glu Arg Gly Arg Arg Asn Leu Glu Trp Lys Glu Pro Pro Ser Met Arg
305                 310                 315                 320

Leu Lys Ala Arg Pro Gly Asn Ser Gly Ser Ser Val Leu Thr Cys Ala
                325                 330                 335

Ala Phe Ser Phe Tyr Pro Pro Glu Leu Lys Phe Arg Phe Leu Arg Asn
            340                 345                 350

Gly Leu Ala Ser Gly Ser Gly Asn Cys Ser Thr Gly Pro Asn Gly Asp
        355                 360                 365

Gly Ser Phe His Ala Trp Ser Leu Leu Glu Val Lys Arg Gly Asp Glu
    370                 375                 380

His His Tyr Gln Cys Gln Val Glu His Glu Gly Leu Ala Gln Pro Leu
```

-continued

```
385                 390                 395                 400

Thr Val Asp Leu Asp Ser Ser Ala Arg Ser Ser Val Pro Val Val Gly
                405                 410                 415

Ile Val Leu Gly Leu Leu Leu Val Val Val Ala Ile Ala Gly Gly Val
            420                 425                 430

Leu Leu Trp Gly Arg Met Arg Ser Gly Leu Pro Ala Pro Trp Leu Ser
        435                 440                 445

Leu Ser Gly Asp Asp Ser Gly Asp Leu Leu Pro Gly Gly Asn Leu Pro
    450                 455                 460

Pro Glu Ala Glu Pro Gln Gly Ala Asn Ala Phe Pro Ala Thr Ser
465                 470                 475
```

```
<210> SEQ ID NO 7
<211> LENGTH: 1480
<212> TYPE: DNA
<213> ORGANISM: Artificial Sequence
<220> FEATURE:
<223> OTHER INFORMATION: 5 homologous arm

<400> SEQUENCE: 7

ggttttgccc atctacttca gcctgttggt ccatctgctg accaccagtc gaccactcac     60
ggctctgtca gtctccctct ctcggctgtt tatattccct gccgcccagg ccggccatga    120
acccctggcc tcccggcctc catccttagt gctggaatta caggcatgtg ctgccgccca    180
ccccctttct tctttgctgt ctatctaccc tgtcaaccta cctgtctgtc agtgtctctc    240
tgtgtgtctg tgtgtttttt ctggcaagat cttggggtgg gcagcagggt gggagacagg    300
ggccaaaggc aaaggctctc atcacagagt gtgtaggcag ggttggggcc acctcaagtg    360
ctggcacatg gaagaaatca gagcaggctt acagctggga gtgggctgct gccaaacctt    420
gtgtgttagg caaccatgcc atgaccaagc cacacccaca gcccacaaat cctggggtgt    480
cttaaagtca cattcagcgt gcaggccttt ccagggctgc gagtctactc caaaaatgct    540
ccaaacgagt aaacatagaa gctgttttgg gaggcaggcc taatgacgtt tgccccggga    600
ggcttccaac cagatacagc aggaacttca agagaggctg gacagaggcc caaggggtgt    660
gcttaggagc tagtgggtgg agttggatgc cctcagagtt ctccagtcct aactgtgtac    720
agacaggatg taagagaaga actggaggct ctaagcagag gatccatcgg ctgcaggcag    780
agggaagagg gcctctgtga ggaacaggct gagcgtcaga ggaggaggcc caggcctggt    840
tctctaggta tgagggacca gcaccccaag aggaaagagg gttggggcct ggagctccag    900
gtctgaggga ggagtgttat gacctgaggg ggagagagga ggctggggtc tgaggaagga    960
gagcaggacc ccgggcacct gagtctgagg gatgaagccg gagcctaggg ttttgggttt   1020
gaggaaagat cttggaactg gactcctgga tctgagggag gtggaactgg actcctggct   1080
tgggtttgag ggctcctgag gctgaaatct gagcccctgg gaatgaggga ggaggagaag   1140
gcctggatcc tctggtctga gggaggagaa aaaggaaata acagaagtct gagacaaatt   1200
ttggtctgtc tagctctgta attaattaac taaagtggat caaatgagaa ggtgaaagtt   1260
cacagaggaa cactcctgtc tgtcgtcttg gactgggtct ccatcccacc atccagcgtc   1320
ctggtctacg aagagtccac agggaccttg tgaagaatca acaaggcggg gtccagagga   1380
gtcacgtgtc ccttccactc cgggtcaccc tgtcggaatg gggatgccac tgccatgggc   1440
gctcagcctc ttgttggtcc tcctgcctca gacctggggc                         1480

<210> SEQ ID NO 8
```

<211> LENGTH: 1445
<212> TYPE: DNA
<213> ORGANISM: Artificial Sequence
<220> FEATURE:
<223> OTHER INFORMATION: 3 homologous arm

<400> SEQUENCE: 8
tcaggtaaga ggccaccagg acctggagtg tgtcaggaag gggacaggaa gaagagccaa 60
agagtggaag agggacaata agtccacttt ttccatgatg tcctagcctt catggaaatc 120
tcactgtggg taacttctct gtgcatctga gtcaaataca cttgacaatc tcaggctcgt 180
ctctgtgtcc gtctgtccgt cttgcttcct ttctgggtgt ctgtcccctt ctctctggag 240
gatcatggca cttcagatcg ggtccagttt tcattctgca cctctgtggg gcacggtgca 300
gtccgtgacc cgagactctc ctgtttgctc tgcagagacc cgccccccac tgatgtatca 360
tctcacggct gtgtcaaacc catctacggg gcttccctct ttctgggcta caggctggtt 420
gggtcctcag cagtatctga cctacaacag cctgcggcag gaagctgacc cctgtggggc 480
ctggatgtgg gaaaatcagg tgtcttggta ttgggagaag gagaccacag acctcaaaag 540
caaagaacag ctcttcttgg aggccctcaa gaccctggag aagatattaa atggtcagaa 600
gaggggtgag cttcagtagg ctgggtttga ggaaggataa tgggtctgga ttcctgggtc 660
aaggaaggag gctggagccc taggcctgaa gtgggaggat taggtctgaa ccctaggaat 720
aagggggaag gttgggatct ggacctcaag gtccgaggga ggagaagaga ggaaggctgg 780
cccttgctcc tgagtctgct tgcctgcgtg ttggcatcta gggacctaca cactgcaggg 840
cctgctgggc tgtgaactgg cctcggataa ttcctcagtg cccacggctg tgtttgccct 900
caatggtgag gagtttatga aattcaaccc aagaatcggc aattggactg gggagtggcc 960
tgagacggaa atcgttgcta atctgtggat gaagcagcct gatgcggcca ggaaggagag 1020
cgagttcctg ctaaactctt gtccggagcg actgctaggc cacctggaga ggggccgacg 1080
gaacctggag tggaagggtg agcccatctc ctgtccctcc tctagatctc cacagccatg 1140
ctcaaagccc acccagcatc agtacaaccc ctctcgccta tcccagtgga tcttctttaa 1200
gataaggtct catgtagccc aggctagctc tcacgtagct caagctagcc atgagctcat 1260
cgtgtagctg aggatggtct tggattcctg atcctcttag cccattccaa gtgctgattt 1320
gacttaagtg tgttgccaca cccagctaat tgttcttgtt tgtgagacag ggtctcaggc 1380
tgactttgaa ctcagagaga tctcttgagt gctgggacaa aaggagtgtg ctgctgtacc 1440
aggct 1445

<210> SEQ ID NO 9
<211> LENGTH: 297
<212> TYPE: DNA
<213> ORGANISM: Artificial Sequence
<220> FEATURE:
<223> OTHER INFORMATION: B2M sequence in A fragment

<400> SEQUENCE: 9
atccagaaaa cccctcaaat tcaagtatac tcacgccacc caccggagaa tgggaagccg 60
aacatactga actgctacgt aacacagttc cacccgcctc acattgaaat ccaaatgctg 120
aagaacggga aaaaaattcc taaagtagag atgtcagata tgtccttcag caaggactgg 180
tctttctata tcctggctca cactgaattc acccccactg agactgatac atatgcctgc 240
agagttaagc atgccagtat ggccgagccc aagaccgtct actgggatcg agacatg 297

<210> SEQ ID NO 10
<211> LENGTH: 45
<212> TYPE: DNA
<213> ORGANISM: Artificial Sequence
<220> FEATURE:
<223> OTHER INFORMATION: linker

<400> SEQUENCE: 10
ggaggtggcg gatccggcgg aggcggctcg ggtggcggcg gctct 45

<210> SEQ ID NO 11
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 11
cgggtcaccc tgtcggaatg ggg 23

<210> SEQ ID NO 12
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 12
cccattccga cagggtgacc cgg 23

<210> SEQ ID NO 13
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 13
agtggcatcc ccattccgac agg 23

<210> SEQ ID NO 14
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 14
ccatgatgtc ctagccttca tgg 23

<210> SEQ ID NO 15
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 15
ctgagcccca ggtctgaggc agg 23

<210> SEQ ID NO 16
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 16
ggaggaccaa caagaggctg agg 23

<210> SEQ ID NO 17
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 17
gagtgtgtca ggaaggggac agg 23

<210> SEQ ID NO 18
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 18
ttacctgagc cccaggtctg agg 23

<210> SEQ ID NO 19
<211> LENGTH: 25
<212> TYPE: DNA
<213> ORGANISM: Artificial Sequence
<220> FEATURE:
<223> OTHER INFORMATION: primer sequence

<400> SEQUENCE: 19
gtttgaggaa ggataatggg tctgg 25

<210> SEQ ID NO 20
<211> LENGTH: 20
<212> TYPE: DNA
<213> ORGANISM: Artificial Sequence
<220> FEATURE:
<223> OTHER INFORMATION: sgRNA sequence

<400> SEQUENCE: 20
ggaggaccaa caagaggctg 20

<210> SEQ ID NO 21
<211> LENGTH: 24
<212> TYPE: DNA
<213> ORGANISM: Artificial Sequence
<220> FEATURE:
<223> OTHER INFORMATION: sgRNA sequence

<400> SEQUENCE: 21
taggggagga ccaacaagag gctg 24

<210> SEQ ID NO 22
<211> LENGTH: 20
<212> TYPE: DNA
<213> ORGANISM: Artificial Sequence
<220> FEATURE:
<223> OTHER INFORMATION: sgRNA sequence

<400> SEQUENCE: 22
cagcctcttg ttggtcctcc 20

<210> SEQ ID NO 23
<211> LENGTH: 24

<212> TYPE: DNA
<213> ORGANISM: Artificial Sequence
<220> FEATURE:
<223> OTHER INFORMATION: sgRNA sequence

<400> SEQUENCE: 23
aaaccagcct cttgttggtc ctcc 24

<210> SEQ ID NO 24
<211> LENGTH: 132
<212> TYPE: DNA
<213> ORGANISM: Artificial Sequence
<220> FEATURE:
<223> OTHER INFORMATION: pT7-sgRNA vector

<400> SEQUENCE: 24
gaattctaat acgactcact atagggggtc ttcgagaaga cctgttttag agctagaaat 60
agcaagttaa aataaggcta gtccgttatc aacttgaaaa agtggcaccg agtcggtgct 120
tttaaaggat cc 132

<210> SEQ ID NO 25
<211> LENGTH: 25
<212> TYPE: DNA
<213> ORGANISM: Artificial Sequence
<220> FEATURE:
<223> OTHER INFORMATION: primer sequence

<400> SEQUENCE: 25
gtagctgtct tcagacactc cagaa 25

<210> SEQ ID NO 26
<211> LENGTH: 25
<212> TYPE: DNA
<213> ORGANISM: Artificial Sequence
<220> FEATURE:
<223> OTHER INFORMATION: primer sequence

<400> SEQUENCE: 26
tgcaggcata tgtatcagtc tcagt 25

<210> SEQ ID NO 27
<211> LENGTH: 25
<212> TYPE: DNA
<213> ORGANISM: Artificial Sequence
<220> FEATURE:
<223> OTHER INFORMATION: primer sequence

<400> SEQUENCE: 27
aattcaagta tactcacgcc accca 25

<210> SEQ ID NO 28
<211> LENGTH: 25
<212> TYPE: DNA
<213> ORGANISM: Artificial Sequence
<220> FEATURE:
<223> OTHER INFORMATION: primer sequence

<400> SEQUENCE: 28
taagttcaag tcccagcaac cacat 25

<210> SEQ ID NO 29
<211> LENGTH: 26
<212> TYPE: DNA
<213> ORGANISM: Artificial Sequence
<220> FEATURE:

<223> OTHER INFORMATION: primer sequence

<400> SEQUENCE: 29
ttgcttctgt ctttcaagtg tgtggg 26

<210> SEQ ID NO 30
<211> LENGTH: 26
<212> TYPE: DNA
<213> ORGANISM: Artificial Sequence
<220> FEATURE:
<223> OTHER INFORMATION: primer sequence

<400> SEQUENCE: 30
attcaagtat actcacgcca cccacc 26

<210> SEQ ID NO 31
<211> LENGTH: 25
<212> TYPE: DNA
<213> ORGANISM: Artificial Sequence
<220> FEATURE:
<223> OTHER INFORMATION: primer sequence

<400> SEQUENCE: 31
aggctgagac caagaggatg acaag 25

<210> SEQ ID NO 32
<211> LENGTH: 25
<212> TYPE: DNA
<213> ORGANISM: Artificial Sequence
<220> FEATURE:
<223> OTHER INFORMATION: primer sequence

<400> SEQUENCE: 32
ctgcttccct ctttcctgag cttcc 25

<210> SEQ ID NO 33
<211> LENGTH: 25
<212> TYPE: DNA
<213> ORGANISM: Artificial Sequence
<220> FEATURE:
<223> OTHER INFORMATION: primer sequence

<400> SEQUENCE: 33
aaacccatgc aggctgtgta actga 25

<210> SEQ ID NO 34
<211> LENGTH: 25
<212> TYPE: DNA
<213> ORGANISM: Artificial Sequence
<220> FEATURE:
<223> OTHER INFORMATION: primer sequence

<400> SEQUENCE: 34
gaataaatga aggcggtccc aggct 25

<210> SEQ ID NO 35
<211> LENGTH: 25
<212> TYPE: DNA
<213> ORGANISM: Artificial Sequence
<220> FEATURE:
<223> OTHER INFORMATION: primer sequence

<400> SEQUENCE: 35
acgagcctga gattgtcaag tgtat 25

<210> SEQ ID NO 36
<211> LENGTH: 25
<212> TYPE: DNA
<213> ORGANISM: Artificial Sequence
<220> FEATURE:
<223> OTHER INFORMATION: primer sequence

<400> SEQUENCE: 36
gtgaaagttc acagaggaac actcc 25

<210> SEQ ID NO 37
<211> LENGTH: 25
<212> TYPE: DNA
<213> ORGANISM: Artificial Sequence
<220> FEATURE:
<223> OTHER INFORMATION: primer sequence

<400> SEQUENCE: 37
catccacaga ttagcaacga tttcc 25

<210> SEQ ID NO 38
<211> LENGTH: 25
<212> TYPE: DNA
<213> ORGANISM: Artificial Sequence
<220> FEATURE:
<223> OTHER INFORMATION: primer sequence

<400> SEQUENCE: 38
gctagcatca gaagatcagg actca 25

<210> SEQ ID NO 39
<211> LENGTH: 25
<212> TYPE: DNA
<213> ORGANISM: Artificial Sequence
<220> FEATURE:
<223> OTHER INFORMATION: primer sequence

<400> SEQUENCE: 39
tagaaagtca accactccta cctgc 25

<210> SEQ ID NO 40
<211> LENGTH: 99
<212> TYPE: PRT
<213> ORGANISM: Artificial Sequence
<220> FEATURE:
<223> OTHER INFORMATION: B2M protein (without signal peptide)

<400> SEQUENCE: 40

```
Ile Gln Lys Thr Pro Gln Ile Gln Val Tyr Ser Arg His Pro Pro Glu
1               5                   10                  15

Asn Gly Lys Pro Asn Ile Leu Asn Cys Tyr Val Thr Gln Phe His Pro
            20                  25                  30

Pro His Ile Glu Ile Gln Met Leu Lys Asn Gly Lys Lys Ile Pro Lys
        35                  40                  45

Val Glu Met Ser Asp Met Ser Phe Ser Lys Asp Trp Ser Phe Tyr Ile
    50                  55                  60

Leu Ala His Thr Glu Phe Thr Pro Thr Glu Thr Asp Thr Tyr Ala Cys
65                  70                  75                  80

Arg Val Lys His Ala Ser Met Ala Glu Pro Lys Thr Val Tyr Trp Asp
                85                  90                  95

Arg Asp Met
```

<210> SEQ ID NO 41

<211> LENGTH: 344
<212> TYPE: PRT
<213> ORGANISM: Artificial Sequence
<220> FEATURE:
<223> OTHER INFORMATION: FcRn protein (without signal peptide)

<400> SEQUENCE: 41

```
Ser Glu Thr Arg Pro Pro Leu Met Tyr His Leu Thr Ala Val Ser Asn
1               5                   10                  15

Pro Ser Thr Gly Leu Pro Ser Phe Trp Ala Thr Gly Trp Leu Gly Pro
            20                  25                  30

Gln Gln Tyr Leu Thr Tyr Asn Ser Leu Arg Gln Glu Ala Asp Pro Cys
        35                  40                  45

Gly Ala Trp Met Trp Glu Asn Gln Val Ser Trp Tyr Trp Glu Lys Glu
    50                  55                  60

Thr Thr Asp Leu Lys Ser Lys Glu Gln Leu Phe Leu Glu Ala Leu Lys
65                  70                  75                  80

Thr Leu Glu Lys Ile Leu Asn Gly Thr Tyr Thr Leu Gln Gly Leu Leu
                85                  90                  95

Gly Cys Glu Leu Ala Ser Asp Asn Ser Ser Val Pro Thr Ala Val Phe
            100                 105                 110

Ala Leu Asn Gly Glu Glu Phe Met Lys Phe Asn Pro Arg Ile Gly Asn
        115                 120                 125

Trp Thr Gly Glu Trp Pro Glu Thr Glu Ile Val Ala Asn Leu Trp Met
    130                 135                 140

Lys Gln Pro Asp Ala Ala Arg Lys Glu Ser Glu Phe Leu Leu Asn Ser
145                 150                 155                 160

Cys Pro Glu Arg Leu Leu Gly His Leu Glu Arg Gly Arg Arg Asn Leu
                165                 170                 175

Glu Trp Lys Glu Pro Pro Ser Met Arg Leu Lys Ala Arg Pro Gly Asn
            180                 185                 190

Ser Gly Ser Ser Val Leu Thr Cys Ala Ala Phe Ser Phe Tyr Pro Pro
        195                 200                 205

Glu Leu Lys Phe Arg Phe Leu Arg Asn Gly Leu Ala Ser Gly Ser Gly
    210                 215                 220

Asn Cys Ser Thr Gly Pro Asn Gly Asp Gly Ser Phe His Ala Trp Ser
225                 230                 235                 240

Leu Leu Glu Val Lys Arg Gly Asp Glu His His Tyr Gln Cys Gln Val
                245                 250                 255

Glu His Glu Gly Leu Ala Gln Pro Leu Thr Val Asp Leu Asp Ser Ser
            260                 265                 270

Ala Arg Ser Ser Val Pro Val Val Gly Ile Val Leu Gly Leu Leu Leu
        275                 280                 285

Val Val Val Ala Ile Ala Gly Gly Val Leu Leu Trp Gly Arg Met Arg
    290                 295                 300

Ser Gly Leu Pro Ala Pro Trp Leu Ser Leu Ser Gly Asp Asp Ser Gly
305                 310                 315                 320

Asp Leu Leu Pro Gly Gly Asn Leu Pro Pro Glu Ala Glu Pro Gln Gly
                325                 330                 335

Ala Asn Ala Phe Pro Ala Thr Ser
            340
```

<210> SEQ ID NO 42
<211> LENGTH: 21
<212> TYPE: PRT
<213> ORGANISM: Artificial Sequence
<220> FEATURE:
<223> OTHER INFORMATION: FcRn signal peptide

<400> SEQUENCE: 42

```
Met Gly Met Pro Leu Pro Trp Ala Leu Ser Leu Leu Leu Val Leu Leu
1               5                   10                  15

Pro Gln Thr Trp Gly
            20
```

<210> SEQ ID NO 43
<211> LENGTH: 1288
<212> TYPE: DNA
<213> ORGANISM: Artificial Sequence
<220> FEATURE:
<223> OTHER INFORMATION: FcRn mRNA (without signal peptide)

<400> SEQUENCE: 43

```
tcagagaccc gccccccact gatgtatcat ctcacggctg tgtcaaaccc atctacgggg     60
cttccctctt tctgggctac aggctggttg ggtcctcagc agtatctgac ctacaacagc    120
ctgcggcagg aagctgaccc ctgtggggcc tggatgtggg aaaatcaggt gtcttggtat    180
tgggagaagg agaccacaga cctcaaaagc aaagaacagc tcttcttgga ggccctcaag    240
accctggaga agatattaaa tggacctac acactgcagg gcctgctggg ctgtgaactg     300
gcctcggata attcctcagt gcccacggct gtgtttgccc tcaatggtga ggagtttatg    360
aaattcaacc caagaatcgg caattggact ggggagtggc ctgagacgga aatcgttgct    420
aatctgtgga tgaagcagcc tgatgcggcc aggaaggaga gcgagttcct gctaaactct    480
tgtccggagc gactgctagg ccacctggag aggggccgac ggaacctgga gtggaaggag    540
ccgccgtcta tgcgcctgaa ggcccgtcct ggcaactctg gctcctccgt gctgacctgt    600
gctgctttct ccttctaccc accggagctc aagttccgat tcctgcgcaa tgggctagcc    660
tcaggctccg ggaattgcag cactggtccc aatggagatg gctctttcca cgcatggtca    720
ttgctggagg tcaaacgtgg agatgagcac cattatcaat gtcaagtgga gcatgagggg    780
ctggcacagc ctctcactgt ggacctagat tcatcagcca gatcttctgt gcctgtggtt    840
ggaatcgttc ttggtttatt gctggtggta gtggccatcg caggcggtgt gctgttgtgg    900
ggcaggatgc gcagcggtct gccagcccca tggctttctc tcagcggcga tgactctggt    960
gacctgttgc ctggtgggaa cttgcccccca gaagctgaac ctcaaggtgc aaatgccttt   1020
ccagccactt cctgatgcag actcgggccc cctgcccact gcagcctttc gggctgtgtg   1080
acctcctgaa ctgtctccga gcctcctgag ggagcctggg cccgatgtcc tcccatggat   1140
ccctgctttt gtggcctgct tcagtttccc ttcttaatgt acatggttgt tttccatctc   1200
cacataaatt tggccccaaa tctgtgtgtg catcgttatt ctcaagtttc aagcagctgg   1260
aataaattga acgcgtctgg gaaagatc                                       1288
```

<210> SEQ ID NO 44
<211> LENGTH: 450
<212> TYPE: DNA
<213> ORGANISM: Artificial Sequence
<220> FEATURE:
<223> OTHER INFORMATION: FcRn signal peptide mRNA

<400> SEQUENCE: 44

```
aggagctagt gggtggagtt ggatgccctc agagttctcc agtcctaact gtgtacagac     60
aggatgtaag agaagaactg gaggctctaa gcagaggatc catcggctgc aggcagaggg    120
```

aagagggcct ctgtgaggaa caggctgagc gtcagaggag gaggcccagg cctggttctc 180
tagctctgta attaattaac taaagtggat caaatgagaa ggtgaaagtt cacagaggaa 240
cactcctgtc tgtcgtcttg gactgggtct ccatcccacc atccagcgtc ctggtctacg 300
aagagtccac agggaccttg tgaagaatca acaaggcggg gtccagagga gtcacgtgtc 360
ccttccactc cgggtcaccc tgtcggaatg gggatgccac tgccctgggc cctcagcctc 420
ttgttggtcc tcctgcctca gacctggggc 450

<210> SEQ ID NO 45
<211> LENGTH: 11197
<212> TYPE: DNA
<213> ORGANISM: Artificial Sequence
<220> FEATURE:
<223> OTHER INFORMATION: modified FcRn gene

<400> SEQUENCE: 45
gacagaggcc caaggggtgt gcttaggagc tagtgggtgg agttggatgc cctcagagtt 60
ctccagtcct aactgtgtac agacaggatg taagagaaga actggaggct ctaagcagag 120
gatccatcgg ctgcaggcag agggaagagg gcctctgtga ggaacaggct gagcgtcaga 180
ggaggaggcc caggcctggt tctctaggta tgagggacca gcacccccaag aggaaagagg 240 gttggggcct ggagctccag gtctgaggga ggagtgttat gacctgaggg ggagagagga 300
ggctggggtc tgaggaagga gagcaggacc ccgggcacct gagtctgagg gatgaagccg 360
gagcctaggg ttttgggttt gaggaaagat cttggaactg gactcctgga tctgagggag 420
gtggaactgg actcctggct tgggtttgag ggctcctgag gctgaaatct gagcccctgg 480
gaatgaggga ggaggagaag gcctggatcc tctggtctga gggaggagaa aaaggaaata 540
acagaagtct gagacaaatt ttggtctgtc tagctctgta attaattaac taaagtggat 600
caaatgagaa ggtgaaagtt cacagaggaa cactcctgtc tgtcgtcttg gactgggtct 660
ccatcccacc atccagcgtc ctggtctacg aagagtccac agggaccttg tgaagaatca 720
acaaggcggg gtccagagga gtcacgtgtc ccttccactc cgggtcaccc tgtcggaatg 780
gggatgccac tgccatgggc gctcagcctc ttgttggtcc tcctgcctca gacctggggc 840
atccagaaaa cccctcaaat tcaagtatac tcacgccacc caccggagaa tgggaagccg 900
aacatactga actgctacgt aacacagttc cacccgcctc acattgaaat ccaaatgctg 960
aagaacggga aaaaaattcc taaagtagag atgtcagata tgtccttcag caaggactgg 1020
tctttctata tcctggctca cactgaattc acccccactg agactgatac atatgcctgc 1080
agagttaagc atgccagtat ggccgagccc aagaccgtct actgggatcg agacatggga 1140
ggtggcggat ccggcggagg cggctcgggt ggcggcggct cttcaggtaa gaggccacca 1200
ggacctggag tgtgtcagga aggggacagg aagaagagcc aaagagtgga agagggacaa 1260
taagtccact ttttccatga tgtcctagcc ttcatggaaa tctcactgtg ggtaacttct 1320
ctgtgcatct gagtcaaata cacttgacaa tctcaggctc gtctctgtgt ccgtctgtcc 1380
gtcttgcttc ctttctgggt gtctgtcccc ttctctctgg aggatcatgg cacttcagat 1440
cgggtccagt tttcattctg cacctctgtg gggcacggtg cagtccgtga cccgagactc 1500
tcctgtttgc tctgcagaga cccgcccccc actgatgtat catctcacgg ctgtgtcaaa 1560
cccatctacg gggcttccct ctttctgggc tacaggctgg ttgggtcctc agcagtatct 1620
gacctacaac agcctgcggc aggaagctga cccctgtggg gcctggatgt gggaaaatca 1680
ggtgtcttgg tattgggaga aggagaccac agacctcaaa agcaaagaac agctcttctt 1740

```
ggaggccctc aagaccctgg agaagatatt aaatggtcag aagaggggtg agcttcagta   1800
ggctgggttt gaggaaggat aatgggtctg gattcctggg tcaaggaagg aggctggagc   1860
cctaggcctg aagtgggagg attaggtctg aaccctagga ataaggggga aggttgggat   1920
ctggacctca aggtccgagg gaggagaaga gaggaaggct ggcccttgct cctgagtctg   1980
cttgcctgcg tgttggcatc tagggaccta cacactgcag ggcctgctgg gctgtgaact   2040
ggcctcggat aattcctcag tgcccacggc tgtgtttgcc ctcaatggtg aggagtttat   2100
gaaattcaac ccaagaatcg gcaattggac tggggagtgg cctgagacgg aaatcgttgc   2160
taatctgtgg atgaagcagc ctgatgcggc caggaaggag agcgagttcc tgctaaactc   2220
ttgtccggag cgactgctag gccacctgga gaggggccga cggaacctgg agtggaaggg   2280
tgagcccatc tcctgtccct cctctagatc tccacagcca tgctcaaagc ccacccagca   2340
tcagtacaac ccctctcgcc tatcccagtg gatcttcttt aagataaggt ctcatgtagc   2400
ccaggctagc tctcacgtag ctcaagctag ccatgagctc atcgtgtagc tgaggatggt   2460
cttggattcc tgatcctctt agcccattcc aagtgctgat ttgacttaag tgtgttgcca   2520
cacccagcta attgttcttg tttgtgagac agggtctcag gctgactttg aactcagaga   2580
gatctcttga gtgctgggac aaaaggagtg tgctgctgta ccaggctgct ttttcttttt   2640
ctttttcttt ttttgttgtt gttatagtta gacagactct cccaatgtag accacgtgac   2700
ctcaaacttg tcatcctctt ggtctcagcc tcccaagtgc taggattttc catgtctttt   2760
tcttcttgtt aacgtctaag agttctttat atattgtgga cccaaatctt caccaaataa   2820
gtgtttcaaa cacactttcc ttgactgttt tcctttcatt cttttaaagt tatcttcaaa   2880
tctttttgtt ttgtttttttc gagacagggt ttctctgtgt agccctggct gtcctggaac   2940
tcactttgta gaccaggctg gcttcgaact cagaaatccg cctgcctctg cctcctgagt   3000
gctgggatta aaggtgtgtg ccaccacgcc cggctttttt tttttttttt tttaagatta   3060
tttagttttg tatataagtg ttcggattgc atgtatgcct gctgcacacc agaagagggc   3120
atcagatccc atttcaggtg cttgtaagat gccatgtggt tgctgggact tgaacttagg   3180
acctctaaaa gagcagccag tgctcttgac tgctaagcca tctctccagt ccccagtcct   3240
cttttgaggg ctgtgttttt gttagtatat cttgcttgga ggtcatgccc agcccaggat   3300
gacctaggtc tctgtgtgta tttggaggag ttttatagct ttccattcta tgtatagatc   3360
ctcttgcttt tctgtctaac aaattgtatg tgaagaaggt ctgtcatttc tccatccaag   3420
tttcagcctg tctggatctg agttgtgtgt gtgctcatgt gggtggagac cagagcacag   3480
cctcgagtgt tgtatttatg acatcttttt ctgaaaaaca aatcttcagg ctggactcag   3540
ctcagtggtt gagagcacac agggatttta tatgtgcaca tgtatatttg tatgtgcacg   3600
tgagtgtcag aagagggcgt tccatcccct gtagctggag ttacagttag ttataacatg   3660
cccagtgtgg gtgctggaac tgaatttgag gcatctttaa gtagcagcaa gcccttagtc   3720
cctgagccac ctctccagcc ccagcccctg tgagattttt actctgtccc tctcacttag   3780
ttggctcagt ttgggattgc actcaggtcc tttctcttgc caagtaagag ctctgccact   3840
gagcaatctt taaggttggt ttttgatttt ggtttttggt ttttcgagac agggtttctc   3900
tgtgttggaa ctcaatctgt agaccaggct ggccttgacc tcaaagaccc atccatctct   3960
gcctcctaag ctctggagat cagaggcatg cgtcaccgcc gaccggctgg ccatgtttta   4020
ggttttaaaa cttaccttta cttatttatc tgtgatttag cgtgtgtgag tggtggtggt   4080
```

```
ggaggtggtg tgtgtgtgtg tgtgtgtgtg tgtgtgtgtg tgtgtgtgtt tcatatgtga   4140
tatatacctg tgctgtgtat ggggtgagca tctgtccaca tgctcagaag ccagagaagg   4200
tggctcctct gtctctttcc atcgtatgtt cttcacccag attctcttga tgagcctgaa   4260
gctacgcagg caaccagcca ggcccctact ggtcctcttt cctctgcccc tatcctcagc   4320
gccagggtta cagttatgaa gatatgttta agttttgaca taagtgctaa gaatttgaac   4380
ttgggtcctc atgcttgtgt aataaacact ttttcatgct gagccattcc cctaattatg   4440
gctaaatagt actccattct agaagcctgc atgctatctt cctttatctg ctgagggtgt   4500
ctacattgtt tctgtagttt ggctgttttt ttgtttgtta gagatttatt tatttattat   4560
atgtaagtat gctgtcttca gacactccag aagaaggcat cagatctcat tacggatggt   4620
tgtgagccac catgtggttg ctaggatttg aactcaggac ctttggaaaa gacgtcaatg   4680
ctcttaacca ctgagccatc tcttcagtcc tgtttggctg ttttgatgtt tctacaatgc   4740
aggatagtgg ccagtgtttc cctgaaattt tgttttgctt ttactatatt tactttattt   4800
ttttattttt ggtttttttga gacagggttt ctctgaatag ctcaggctgt cctggaactc   4860
actctgtaga ccagtatggc cttgaactca gaaatctgtc tgcctctgcc tcccaagttc   4920
tgggattaaa ggcatgtgcc accactgccc atccctaaaa ttttgatacc aacttctgga   4980
taagtgtcca caaataggat agctaactcc attaaacaag aaaaaaaatt tttattatgt   5040
tttttgcttc catgtatgtc tgtgcaccat gtgcatgcag tactcacaga ggccagagga   5100
gggcgtcagg tcccctggtg ctggagttac agatggttag gagttgttca ccacatgggt   5160
gctctgactt gaacctgagt cctctggagg agctgccact cactacttga ctaattttac   5220
ccgctgagtc acttctctag ctctgagctc atttaccatg gaaaaccatg gtggcctgtg   5280
tggggataca tgtctttaat gctagcactc cggaggcagg gacaggtagt ctctgcacta   5340
cctgcactcc ccttgacaac cggtccaggt tccacgggta ctgactacag ttgctacatt   5400
gtgtctatgt gtgattttgt tcttcttaac aggcttctgg taccaggtgt taggttgtgt   5460
tactgtttcc ttccaaacat acaaacaagg caggggctct accactgagc cacgccccag   5520
cccttcactg gggaattcga ggctctaaca ttgagcatac cattgacgct catttgactt   5580
aaaatatttt taaggttaca cttattatta aggttactta cttgtgaatg agtgtgcata   5640
tgtgtgtgcg tgtgtgcgtg tgtgtgtgtg tgtgtgcgcg tgcgtgcgcg cgcgcgcgcg   5700
cgtgcgtgcg tgcgtgtgtg tgtgtgtgtg tgtgtgtgta gataggtcag agaacttggt   5760
gagttggatc tctccttttg ccatgtagat tctagggatg gaactcaggt catcaggctt   5820
gtccgcaggt gtctttacgt cacgtcacca gccctcttgt atttttctaa acctttttct   5880
gactatattt attttattgt taatttctgt ggatgtgtgt gtacatatat ggtgcaagtg   5940
accacagatg ccagaaggag gatcaggtcg tctgcagctg gagttagtta taggtggtta   6000
agtgtcgccc agttggtgct gagaattgag ctcagttctg tagagagaac agaaaacgct   6060
ctagcggcta agctgtgtct ctcgggcgct tcactggccc tcttttgact ttttcttttt   6120
tctttttctt tttcttttt ttttttttc tggagctgag gcccgaaccc agggccttgg   6180
gcttgctagg caagcactct accactgaac taaatcccca accccttgac tttttatttt   6240
gagacatggt ctcactaagt ttcccaagct aactcccagc tcaatctgtg gcttaactgg   6300
tgagcctgta gcacctctgc cttggccacc caggttacat ttctggggca aaggtgcttc   6360
cttttttttt tcttcttctt cttcttctgt taaacagaag ccaaggctgg gctgactctc   6420
cgaaccctca gggtcagaac tggaaaacag gagaaccgag ggtgtctctc agctacccac   6480
```

```
aggaagtcat cctcactgga aaacaatagc aagcacaagg caggacacag aagtgctgac   6540
tgaggtccgg tcctctgtgg cagagagccg gtgcctcagg tcttcctaga tgccagtgag   6600
gcccctcttt cggggaagct cgttagcttc ctcttcctaa gaagttgtca gcttattttc   6660
tgctgagaac cagagcagaa ccaagattgt gagacccacc ctagacagag ggaacgcctc   6720
tgccatgcac agcctttctg ggtctcaga tccccatgga cttcattttg tctaggggtt    6780
tattgctgtt gattcagggt cttgtgtagc ccaggctggc cccaaacttc ctatttcatc   6840
aaagtaacct tgaactcctg atcctctgac ctccagtctg gagtgctgag attacaggtg   6900
tacgccagca tgcatgacca atgtcagtgt gccggggatc aaacctagga acccaggact   6960
tcacaccgga aactgggcca catccccagc cataatatct ctctctctct ctctgtctct   7020
ctgtctctct gtctctctct ctctctgttt cttttttctg agacagggtt tctctgtata   7080
gccctggctg tcctggaact cactttgtag accaggctgg cctcgaactc agaaatccgc   7140
ctgcctctgc ctcccaagtg ctgggattaa aggcgtgcgc taccaccgcc cacttctttc   7200
tttctttctt tctttctttc tttctctctc tctctctctc tctctctctc tctctctctc   7260
tctctctctc tctctttctt cctttctttc tttccttggt ctcactatgt cactatgtag   7320
ccttggctag cctggaactg ctatgtagac caggttgccc tggtatccac agagatcaac   7380
ttgcctctgc tccctgaatg ctgggattca agatgtacta cacaccccac ccacaggtct   7440
cagtttttgc aagagcatcc aactcatttg gaactcatga ttttccggca acagttcctc   7500
aggtgctggg atcacttgtg tgggcatgca ccatcccacc cagctaggac agtcatgtct   7560
ctttgctcta tatatacact aatgtgttcc cagggccacg aataggtcac ggcactagag   7620
agatgtgcac taagtctccg tttagaaaca ggtagatgga ggagttgggg ctcagctggt   7680
agaaagcttg cttaaatggg ctccaccact ggcactgcat aaaccagtat ggcggcacac   7740
acctgctgtc tctcagcttt tagcaagtgg aagaaggaaa atcaggaatt caaagtcatc   7800
tgtatctata taataagttc aagactggtc tgggctgaga gtgaaacaaa caaatgtgcg   7860
cgagaagagg cgctgtgagc gccgagtttg ctgtgatgaa gacctgggtt ctggtcccca   7920
ggtccccttg caaaggctgg gcgtactgct gcgtgtctgt agctgcaggg atgggtctgg   7980
cagagacgga gcctcaccag ccactggcat ggctgaaagg gaggacccca ggttcatgga   8040
gaggctctgt ctcaaaaaat aagtgagccc ggcgtggtgg cgcacgcctt taatcccagc   8100
acttgggagg cagacacagg cagatttctg agttcgaggc cagcctggtc tacaaagtga   8160
gttcctggac agccagggct acacagagaa accctgtctc gaaaaaaacaa acaaacaaac  8220
aaacaaaacc ccaaaaaaca acaacaaaaa aaagtggatg tggggagaga tggctcagtg   8280
gttaggaaca ctccctgttc ttgcagagga ccaggattta attcctagct cccatagggt   8340
aactcaccac catctgtaac tccatttcca ggggctctga tgtcctcatc tggcctccac   8400
agacactgca tgcatgtggt gcagagacac acatgctaaa aagcacccag acacacagag   8460
tgaaaaatat ataaagggga aaaaatgcaa agagcgaaag aggaaggagc ctgcaattga   8520
cctgtggcct tgacccatgc acatgccaca cacaccaaaa taagggggtg cagtggtggg   8580
gtcagcaggg tggggtgtct gtcactctgg gaagccctcc aagtcagcac agtgctgata   8640
cagggaagtg gagtctgtcc atggcaagct tcacccaagc cttggtgggg gtggggtggg   8700
tgggtgaggt catagcctag cctaactgct ggcccatccc attgcctgtg tccctgcaga   8760
gccgccgtct atgcgcctga aggcccgtcc tggcaactct ggctcctccg tgctgacctg   8820
```

-continued

```
tgctgctttc tccttctacc caccggagct caagttccga ttcctgcgca atgggctagc   8880
ctcaggctcc gggaattgca gcactggtcc caatggagat ggctctttcc acgcatggtc   8940
attgctggag gtcaaacgtg gagatgagca ccattatcaa tgtcaagtgg agcatgaggg   9000
gctggcacag cctctcactg tggacctagg tgaggctgcc cctccagcct cagtgtcttc   9060
tttgtttttt tttgtttttt taaaagatgt atttatttat ttcatgtatg tgagtacact   9120
gtcgctgtct tcagacacac cagaagagag catcagatcc tattacagac agttgtgagc   9180
caccatgtgg ttgctgggaa ttgaattcag gacctctaga agagcaggcg gtgctcttaa   9240
ccgctgagcc atctctctct ccagccccat tgtcttcttt gtttctgctc ctggcttctg   9300
attctccatt agctctgtgg ccagttcccc ctgagtctga ccatgatgag tcttgctgct   9360
actggtcttc atggtgtttg accattcact tttgcctctg acagttcttg ccatggcttt   9420
ggtaaagcac caactttgtt gactgtcctg tgactgctcc gccttcctct gttgggttct   9480
cacctagttc tgtcacagtg tggctgtgtc ctctcagtat aggtctcctc ctcctcttcc   9540
tcctcctcct attccttttc tttctcctcc tccttccatc cctcctcctc cctcctactt   9600
cctccccctc tccccttcct cctcctcctc tccctccttc tcctcctcct cctccttctt   9660
cagatttata tctaagtgta tccatatgta tttaattttc ccactttctt tgtgtgagag   9720
gggagagcag aggtgagtct gtgccatggg atacttgtgg cgacagagga caacttgtgg   9780
ttgtcagcct tggggctcaa acttaggtca ccgggcttta tggcaaaggc aatgccttca   9840
ctccttgaac ctctgacagc ctagatttat ggagggtcgg gctcaggtct cctggaattc   9900
gacacgagtt ctgggaacca aactctggtc ctccggaaga gctgcaagcc gtctctccag   9960
cacagtggct gactcttttt ttctcttttt tctttctttt tgtttttgtt tttgagacag  10020
ggtttctctg tagagctctg gctgtcctgg aactcacaat gtagaggagt ctggcctcta  10080
acccatagat ctgtgtgcct ctgcctccca agtgctggga ttaagaggtg tgtcaccact  10140
gtgtggccgg ttcttatatt cagtgaggaa acacatgagg cccagggcct tttctccgca  10200
tacacccacc ctcaaataca tgcttccggg ggtctccgag aaatcatcaa ctcctttctt  10260
ccctgtcttc atgatacttt ctggctgcag attcatcagc cagatcttct gtgcctgtgg  10320
ttggaatcgt tcttggttta ttgctggtgg tagtggccat cgcaggcggt gtgctgttgt  10380
ggggcaggat gcgcagcggt ctgccaggta tatgcaggat gggggagggg cggggccgtg  10440
tgcaggattg ggtgggagtg gccttgtgca ggatgaggga ggggcggggc cgtgtgcagg  10500
attggggtgg ggcgtggccg tgtgcagaat gagggagggg cgtggccgtg tgcaggattg  10560
gggaggggag ggaaggggcc gtgtgcagga ttggggaggg gcgtagctgt gtgcaggatt  10620
ggggaaggga ggggccgtgt gcaggattgg gggtcgtggc aggaagtagc gactcagaaa  10680
gaaagagggg aggcagagag ataatagaga caaaagagtc cctgaccacc ctgggaaaag  10740
agatgggaac agagaccata gcgtgaccct gtcaggtgtg ttgggtgggt gagaccttag  10800
atacttgtgc tgacctctgt tcctctctct cagccccatg gctttctctc agcggcgatg  10860
actctggtga cctgttgcct ggtgggaact tgccccccaga agctgaacct caaggtgcaa  10920
atgcctttcc agccacttcc tgatgcagac tcgggccccc tgcccactgc agcctttcgg  10980
gctgtgtgac ctcctgaact gtctccgagc ctcctgaggg agcctgggcc cgatgtcctc  11040
ccatggatcc ctgcttttgt ggcctgcttc agtttccctt cttaatgtac atggttgttt  11100
tccatctcca cataaatttg gccccaaatc tgtgtgtgca tcgttattct caagtttcaa  11160
gcagctggaa taaattgaac gcgtctggga aagatca                           11197
```

```
<210> SEQ ID NO 46
<211> LENGTH: 15
<212> TYPE: PRT
<213> ORGANISM: Artificial Sequence
<220> FEATURE:
<223> OTHER INFORMATION: linker peptide

<400> SEQUENCE: 46

Gly Gly Gly Gly Ser Gly Gly Gly Gly Ser Gly Gly Gly Gly Ser
1               5                   10                  15


<210> SEQ ID NO 47
<211> LENGTH: 5
<212> TYPE: PRT
<213> ORGANISM: Artificial Sequence
<220> FEATURE:
<223> OTHER INFORMATION: linker peptide

<400> SEQUENCE: 47

Gly Gly Gly Gly Ser
1               5
```

GENETICALLY MODIFIED NON-HUMAN ANIMAL EXPRESSING A B2M/FCRN FUSION PROTEIN

CLAIM OF PRIORITY

This application is a National Stage Application under 35 U.S.C. § 371 and claims the benefit of International Application No. PCT/CN2021/100958, filed on Jun. 18, 2021, which claims the benefit of Chinese Patent Application App. No. 202010568508.7, filed on Jun. 19, 2020. The entire contents of the foregoing are incorporated herein by reference.

TECHNICAL FIELD

This disclosure relates to genetically modified animals which express a B2M/FcRn fusion protein, and methods of use thereof.

BACKGROUND

Immunodeficient animals are very important for disease modeling and drug developments. In recent years, immunodeficient mice are routinely used as model organisms for research of the immune system, cell transplantation strategies, and the effects of disease on mammalian systems. They have also been extensively used as hosts for normal and malignant tissue transplants, and are widely used to test the safety and efficacy of therapeutic agents.

However, the engraftment capacity of these immunodeficient animals can vary. More immunodeficient animals with different genetic makeup and better engraftment capacities are needed.

SUMMARY

This disclosure is related to genetically-modified animals that express B2M/FcRn fusion protein. In some embodiments, the animal is used as an immune-deficient animal model (e.g., having a CD132 gene knockout). In some embodiments, the animal has a disruption or deletion of endogenous B2M gene. As B2M is an essential component for both the MHC class I protein complex and FcRn protein complex, the animal does not express endogenous MHC class I protein complex, but has a functional FcRn protein complex. As such, the animal can be used as a better animal model with the reconstructed human immune system. The animal can also be used in FcRn-associated signal mechanism research, immune system research, and immune-related new drug research and development.

In one aspect, the disclosure is related to a genetically-modified non-human animal expressing a fusion protein comprising a β2 microglobulin (B2M) and a neonatal Fc receptor (FcRn).

In some embodiments, the genome of the animal comprises at least one chromosome comprising a sequence encoding the fusion protein.

In some embodiments, the sequence encoding the fusion protein is operably linked to an endogenous regulatory element (e.g., a promoter) at an endogenous FcRn gene locus or an endogenous B2M locus in the at least one chromosome.

In some embodiments, the animal is a mouse, and the sequence encoding the fusion protein is operably linked to a mouse regulatory element (e.g., a promoter) at a mouse FcRn gene locus or a mouse B2M gene locus in the at least one chromosome.

In some embodiments, the fusion protein comprises an endogenous B2M (with or without a signal peptide) and/or an endogenous FcRn (with or without a signal peptide).

In some embodiments, the B2M and FcRn are linked via a linker peptide.

In some embodiments, the fusion protein further comprises a signal peptide of endogenous FcRn (e.g., at the N-terminus of the fusion protein).

In some embodiments, the fusion protein comprises, preferably from N-terminus to C-terminus: (a) a signal peptide of an endogenous FcRn; (b) an endogenous B2M, preferably without a signal peptide thereof; (c) optionally a linker peptide; and (d) an endogenous FcRn, preferably without a signal peptide thereof.

In some embodiments, the B2M comprises or consists of an amino acid sequence that is at least 70%, 75%, 80%, 85%, 90%, 95%, 99%, or 100% identical to amino acids 21-119 of SEQ ID NO: 2.

In some embodiments, the FcRn comprises or consists of an amino acid sequence that is at least 70%, 75%, 80%, 85%, 90%, 95%, 99%, or 100% identical to amino acids 22-365 of SEQ ID NO: 4.

In some embodiments, the signal peptide comprises an amino acid sequence that is at least 70%, 75%, 80%, 85%, 90%, 95%, 99%, or 100% identical to amino acids 1-21 of SEQ ID NO: 4.

In some embodiments, the fusion protein comprises or consists of an amino acid sequence that is at least 70%, 75%, 80%, 85%, 90%, 95%, 99%, or 100% identical to SEQ ID NO: 6.

In some embodiments, the animal is heterozygous with respect to the sequence encoding the fusion protein. In some embodiments, the animal is homozygous with respect to the sequence encoding the fusion protein.

In some embodiments, the animal does not express endogenous B2M.

In some embodiments, the animal does not express endogenous FcRn.

In some embodiments, the B2M and FcRn can associate with each other, forming a functional FcRn protein complex, in some embodiments, the FcRn protein complex can bind to an immunoglobulin G (e.g., a human IgG or an endogenous IgG) at acidic pH (e.g., pH<6.5).

In some embodiments, the PK result of the animal's serum IgG is consistent with pharmacokinetic characteristics.

In some embodiments, the animal is a mammal, e.g., a monkey, a rodent, or a mouse.

In some embodiments, the animal is an immunodeficient mouse. In some embodiments, the animal is a B-NDG mouse, NOD/scid mouse, a NOD/scid nude mouse. In some embodiments, the genome of the animal comprises a disruption in the animal's endogenous CD132 gene. In some embodiments, the animal is a B-NDG mouse.

In some embodiments, the animal further comprises a sequence encoding an additional human or chimeric protein. In some embodiments, the additional human or chimeric protein is Colony Stimulating Factor (CSF1), Colony Stimulating Factor 2 (CSF2), IL3, IL15, programmed cell death protein 1 (PD-1), cytotoxic T-lymphocyte-associated protein 4 (CTLA-4), Lymphocyte Activating 3 (LAG-3), B And T Lymphocyte Associated (BTLA), Programmed Cell Death 1 Ligand 1 (PD-L1), CD27, CD28, CD47, THPO, CD137, CD154, T-Cell Immunoreceptor With Ig And ITIM Domains (TIGIT), T-cell Immunoglobulin and Mucin-Domain Containing-3 (TIM-3), Glucocorticoid-Induced TNFR-Related Protein (GITR), Signal regulatory protein α (SIRPα), or TNF Receptor Superfamily Member 4 (OX40).

In one aspect, the disclosure is related to a method for making a genetically-modified, non-human animal, comprising: inserting in at least one cell of the animal, a sequence encoding a region of endogenous B2M at an endogenous FcRn gene locus, thereby generating a B2M/FcRn fusion gene.

In some embodiments, the insertion site is located within exon 1, exon 2, exon 3, exon 4, exon 5, exon 6, and/or exon 7 of endogenous FcRn gene.

In some embodiments, the animal is a mouse, and the insertion site is within exon 2 of endogenous mouse FcRn gene.

In some embodiments, the animal is a mouse, and the sequence encoding the region of endogenous B2M comprises all or part of exon 1, exon 2, and/or exon 3 of mouse B2M gene.

In some embodiments, the region of endogenous B2M comprises a sequence that is at least 70%, 75%, 80%, 85%, 90%, 95%, 99%, or 100% identical to amino acids 21-119 of SEQ ID NO: 2.

In some embodiments, the B2M/FcRn fusion gene comprises the following elements, preferably from 5' end to 3' end: (a) all or part of exon 1, exon 2, and/or exon 3 of an endogenous B2M gene; (b) an optional sequence encoding a linker peptide; and (c) all or part of exon 2, exon 3, exon 4, exon 5, exon 6, and/or exon 7 of an endogenous FcRn gene.

In some embodiments, the B2M/FcRn fusion gene further comprises, preferably at its 5' end, all or part of exon 2 of the endogenous FcRn gene.

In some embodiments, the B2M/FcRn fusion gene encodes an amino acid sequence that is at least 70%, 75%, 80%, 85%, 90%, 95%, 99%, or 100% identical to SEQ ID NO: 6.

In one aspect, the disclosure is related to a method of producing a genetically-modified rodent, the method comprising (a) providing a plasmid comprising a 5' homologous arm and a 3' homologous arm; (b) providing a small guide RNA (sgRNA) that targets a sequence in exon 2 and/or intron 2 of the endogenous FcRn gene; (c) modifying genome of a fertilized egg or an embryonic stem cell by using the plasmid of step (a), the sgRNA of step (b), and Cas9; and (d) transferring the fertilized egg to a receipt rodent or transferring the embryonic stem cell to a blastocyst, which is then transferred to a receipt rodent, thereby producing a genetically-modified rodent.

In some embodiments, the sgRNA targets any one of SEQ ID NOs: 11-18. In some embodiments, the sgRNA targets SEQ ID NO: 16.

In some embodiments, the 5' homologous arm is at least 80% identical to SEQ ID NO: 7 and the 3' homologous arm is at least 80% identical to SEQ ID NO: 8.

In some embodiments, the rodent is a mouse.

In some embodiments, the method further comprises establishing a stable mouse line from progenies of the genetically-modified rodent.

In some embodiments, the fertilized egg or an embryonic stem cell has a NOD/scid background, a NOD/scid nude background, or a B-NDG background.

In some embodiments, the fertilized egg or an embryonic stem cell has a B-NDG background and the endogenous B2M gene is knocked out.

In one aspect, the disclosure is related to a method of determining effectiveness of an agent or a combination of agents for the treatment of cancer, comprising: (a) engrafting tumor cells to the animal as described herein, thereby forming one or more tumors in the animal; (b) administering the agent or the combination of agents to the animal; and (c) determining inhibitory effects on the tumors.

In some embodiments, before engrafting the tumor cells to the animal, human peripheral blood cells (hPBMC) or human hematopoietic stem cells are injected to the animal.

In some embodiments, the tumor cells are from cancer cell lines.

In some embodiments, the tumor cells are from a tumor sample obtained from a human patient.

In some embodiments, the inhibitory effects are determined by measuring the tumor volume in the animal.

In some embodiments, the tumor cells are colon cancer cells, lung cancer cells, melanoma cells, lung cancer cells, primary lung carcinoma cells, non-small cell lung carcinoma (NSCLC) cells, small cell lung cancer (SCLC) cells, primary gastric carcinoma cells, bladder cancer cells, breast cancer cells, and/or prostate cancer cells.

In some embodiments, the agent is an antibody or antigen-binding fragment thereof. In some embodiments, the antibody or antigen-binding fragment thereof is an anti-PD-1 antibody (e.g., pembrolizumab and/or ipilimumab).

In some embodiments, the agent is a CAR-T, a TCR-T, or an antigen-binding fragment thereof.

In some embodiments, the combination of agents comprises one or more agents selected from the group consisting of paclitaxel, cisplatin, carboplatin, pemetrexed, 5-FU, gemcitabine, oxaliplatin, docetaxel, and capecitabine.

In one aspect, the disclosure is related to a method of producing an animal comprising a human hemato-lymphoid system, the method comprising: engrafting a population of cells comprising human hematopoietic cells or human peripheral blood cells into the animal as described herein.

In some embodiments, the human hemato-lymphoid system comprises human cells selected from the group consisting of hematopoietic stem cells, myeloid precursor cells, myeloid cells, dendritic cells, monocytes, granulocytes, neutrophils, mast cells, lymphocytes, and platelets.

In one aspect, the disclosure is related to a fusion protein comprising an amino acid sequence that is at least 70%, 75%, 80%, 85%, 90%, 95%, 99%, or 100% identical to SEQ ID NO: 6.

In one aspect, the disclosure is related to a nucleic acid encoding the fusion protein as described herein.

In one aspect, the disclosure is related to a cell or an animal comprising the fusion protein and/or the nucleic acid as described herein.

In one aspect, the disclosure is related to a protein comprising an amino acid sequence, in some embodiments, the amino acid sequence is one of the following: (a) an amino acid sequence set forth in SEQ ID NO: 2, 4, 6, 40, 41, or 42; (b) an amino acid sequence that is at least 90% identical to SEQ ID NO: 2, 4, 6, 40, 41, or 42; (c) an amino acid sequence that is at least 91%, 92%, 93%, 94%, 95%, 96%, 97%, 98%, or 99% identical to SEQ ID NO: 2, 4, 6, 40, 41, or 42; (d) an amino acid sequence that is different from the amino acid sequence set forth in SEQ ID NO: 2, 4, 6, 40, 41, or 42 by no more than 10, 9, 8, 7, 6, 5, 4, 3, 2 or 1 amino acid; and (e) an amino acid sequence that comprises a substitution, a deletion and/or insertion of one, two, three, four, five or more amino acids to the amino acid sequence set forth in SEQ ID NO: 2, 4, 6, 40, 41, or 42.

In one aspect, the disclosure is related to a nucleic acid comprising a nucleotide sequence, in some embodiments, the nucleotide sequence is one of the following: (a) a sequence that encodes the protein as described herein; (b) SEQ ID NO: 1, 3, 5, 7, 8, 9, 43, 44, or 45; (c) a sequence that is at least 90% identical to SEQ ID NO: 1, 3, 5, 7, 8, 9, 43, 44, or 45; and (d) a sequence that is at least 91%, 92%, 93%, 94%, 95%, 96%, 97%, 98%, or 99% identical to SEQ ID NO: 1, 3, 5, 7, 8, 9, 43, 44, or 45.

In one aspect, the disclosure is related to a cell comprising the protein and/or the nucleic acid as described herein. In one aspect, the disclosure is related to an animal comprising the protein and/or the nucleic acid as described herein.

In one aspect, the disclosure relates to a genetically-modified, non-human animal whose genome comprise a disruption in the animal's endogenous Beta-2-Microglobulin (B2M) gene. In some embodiments, the disruption of the endogenous B2M gene comprises deletion of one or more exons or part of exons selected from the group consisting of exon 1, exon 2, exon 3, or exon 4 of the endogenous B2M gene.

In some embodiments, the disruption of the endogenous B2M gene comprises deletion of exon 2 of the endogenous B2M gene. In some embodiments, the disruption of the endogenous B2M gene comprises deletion of part of exon 1 of the endogenous B2M gene. In some embodiments, the disruption of the endogenous B2M gene further comprises deletion of part of exon 3 of the endogenous B2M gene.

In some embodiments, the disruption of the endogenous B2M gene comprises deletion of exons 1-4 of the endogenous B2M gene.

In some embodiments, the disruption of the endogenous B2M gene further comprises deletion of one or more introns or part of introns selected from the group consisting of intron 1, intron 2, and intron 3 of the endogenous B2M gene.

In some embodiments, the disruption consists of deletion of more than 10 nucleotides in exon 1, deletion of the entirety of intron 1, exon 2, intron 2, and deletion of more than 10 nucleotides in exon 3.

In some embodiments, the animal is homozygous with respect to the disruption of the endogenous B2M gene. In some embodiments, the animal is heterozygous with respect to the disruption of the endogenous B2M gene.

In some embodiments, the disruption prevents the expression of functional B2M protein.

In some embodiments, the length of the remaining exon sequences at the endogenous B2M gene locus is less than 65% (e.g., 60%) of the total length of all exon sequences of the endogenous B2M gene.

In some embodiments, the length of the remaining sequences at that the endogenous B2M gene locus is less than 50% (e.g., 30%) of the full sequence of the endogenous B2M gene.

In one aspect, the disclosure relates to a genetically-modified, non-human animal, wherein the genome of the animal does not have exon 2 of B2M gene at the animal's endogenous B2M gene locus.

In some embodiments, the genome of the animal does not have one or more exons or part of exons selected from the group consisting of exon 1, exon 3, and exon 4.

In some embodiments, the genome of the animal does not have one or more introns or part of introns selected from the group consisting of intron 1, intron 2, and intron 3.

In one aspect, the disclosure relates to a B2M knockout non-human animal, wherein the genome of the animal comprises from 5' to 3' at the endogenous B2M gene locus, (a) a first DNA sequence; optionally (b) a second DNA sequence comprising an exogenous sequence; (c) a third DNA sequence. In some embodiments, the first DNA sequence, the optional second DNA sequence, and the third DNA sequence are linked. In some embodiments, the first DNA sequence comprises an endogenous B2M gene sequence that is located upstream of intron 1, the second DNA sequence can have a length of 0 nucleotides to 1000 nucleotides (e.g., about or at least 50, 100, 150, 200, 250, 300, 350, 400, 450, 500, 550, 600, 650, 700, 750, 800, 850, 900, 950, or 1000), and the third DNA sequence comprises an endogenous B2M gene sequence that is located downstream of intron 2.

In some embodiments, the first DNA sequence comprises a sequence that has a length (5' to 3') of from 10 to 100 nucleotides (e.g., approximately 10, 20, 30, 40, 50, 60, 70, 80, 90, 100 nucleotides). In some embodiments, the length of the sequence refers to the length from the first nucleotide in exon 1 of the B2M gene to the last nucleotide of the first DNA sequence. In some embodiments, the first DNA sequence comprises at least 10 nucleotides from exon 1 of the endogenous B2M gene. In some embodiments, the first DNA sequence has at most 100 nucleotides from exon 1 of the endogenous B2M gene.

In some embodiments, the third DNA sequence comprises a sequence that has a length (5' to 3') of from 1 to 30 nucleotides (e.g., approximately 1, 2, 3, 4, 5, 6, 7, 8, 9, 10, 11, 12, 13, 14, 15, 16, 17, 18, 19, 20, 21, 22, 23, 24, 25, 26, 27, or 28 nucleotides). In some embodiments, the length of the sequence refers to the length from the first nucleotide in the third DNA sequence to the last nucleotide in exon 3 of the endogenous B2M gene. In some embodiments, the third DNA sequence comprises at least 1 nucleotides from exon 3 of the endogenous B2M gene.

In some embodiments, the third DNA sequence comprises a sequence that has a length (5' to 3') of from 1 to 432 nucleotides (e.g., approximately or at least 1, 2, 3, 4, 5, 6, 7, 8, 9, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 350, or 400 nucleotides). In some embodiments, the length of the sequence refers to the length from the first nucleotide in the third DNA sequence to the last nucleotide in exon 4 of the endogenous B2M gene.

In one aspect, the disclosure relates to a genetically-modified, non-human animal produced by a method comprising knocking out one or more exons of endogenous B2M gene by using (1) a first nuclease comprising a zinc finger protein, a TAL-effector domain, or a single guide RNA (sgRNA) DNA-binding domain that binds to a target sequence in exon 1 of the endogenous B2M gene or upstream of exon 1 of the endogenous B2M gene, and (2) a second nuclease comprising a zinc finger protein, a TAL-effector domain, or a single guide RNA (sgRNA) DNA-binding domain that binds to a sequence in exon 3 of the endogenous B2M gene.

In some embodiments, the nuclease is CRISPR associated protein 9 (Cas9).

In some embodiments, the animal does not express a functional B2M protein. In some embodiments, the animal does not express a functional interleukin-2 receptor.

In some embodiments, the animal has one or more of the following characteristics:

(a) the percentage of T cells (CD3+ cells) is less than 5%, 2%, 1.5%, 1%, 0.7%, or 0.5% of leukocytes in the animal;

(b) the percentage of B cells (e.g., CD3− CD19+ cells) is less than 1%, 0.1% or 0.05% of leukocytes in the animal;

(c) the percentage of NK cells (e.g., CD3− CD49b+ cells) is less than 5%, 2% or 1.5% of leukocytes in the animal;
(d) the percentage of CD4+ T cells is less than 1%, 0.5%, 0.3%, or 0.1% of T cells;
(e) the percentage of CD8+ T cells is less than 1%, 0.5%, 0.3%, or 0.1% of T cells;
(f) the percentage of CD3+CD4+ cells, CD3+CD8+ cells, CD3− CD19+ cells is less than 5%, 1% or 0.5% of leukocytes in the animal;
(g) the percentage of T cells, B cells, and NK cells is less than 5%, 4%, 3%, 2% or 1% of leukocytes in the animal.

In some embodiments, the animal after being engrafted with human hematopoietic stem cells to develop a human immune system has one or more of the following characteristics:
(a) the percentage of human CD45+ cells is about or at least 10%, 20%, 30%, 40%, or 50% of leukocytes of the animal;
(b) the percentage of human CD3+ cells about or at least 10%, 20%, 30%, 40%, or 50% of leukocytes in the animal;
(c) the percentage of human CD19+ cells is about or at least 10%, 20%, 30%, 40%, or 50% of leukocytes in the animal;
(d) the percentage of human CD45+ cells increased slower than the percentage of human CD45+ cells in a NOD-Prkdc$^{scid}$ IL-2rγ$^{null}$ mouse after being engrafted with human hematopoietic stem cells.

In some embodiments, the animal does not have graft-versus-host disease (GVHD), or exhibit less severe symptoms of GVHD as compared to a NOD-Prkdc$^{scid}$ IL-2rγ$^{null}$ mouse.

In some embodiments, the animal has one or more of the following characteristics:
(a) the animal has no functional T-cells and/or no functional B-cells;
(b) the animal exhibits reduced macrophage function relative to a NOD/scid mouse;
(c) the animal exhibits no NK cell activity;
(d) the animal exhibits reduced dendritic function relative to a NOD/scid mouse; and
(e) the animal does not have xenogeneic GVHD.

In some embodiments, the animal is a mammal, e.g., a monkey, a rodent, a rat, or a mouse. In some embodiments, the animal is a NOD/scid mouse, or a NOD/scid nude mouse, or a NOD-Prkdc$^{scid}$ IL-2rγ$^{null}$ mouse.

In some embodiments, the animal further comprises a sequence encoding a human or chimeric protein. In some embodiments, the human or chimeric protein is programmed cell death protein 1 (PD-1). In some embodiments, the animal further comprises a disruption in the animal's endogenous Forkhead Box N1 (Foxn1) gene.

In one aspect, the disclosure relates to methods of determining effectiveness of an agent or a combination of agents for the treatment of cancer, comprising: engrafting tumor cells to the animal described herein, thereby forming one or more tumors in the animal; administering the agent or the combination of agents to the animal; and determining the inhibitory effects on the tumors.

In some embodiments, before engrafting the tumor cells to the animal, human peripheral blood cells (hPBMC) or human hematopoietic stem cells are injected to the animal.

In some embodiments, the tumor cells are from cancer cell lines. In some embodiments, the tumor cells are from a tumor sample obtained from a human patient.

In some embodiments, the inhibitory effects are determined by measuring the tumor volume in the animal.

In some embodiments, the tumor cells are melanoma cells, lung cancer cells, primary lung carcinoma cells, non-small cell lung carcinoma (NSCLC) cells, small cell lung cancer (SCLC) cells, primary gastric carcinoma cells, bladder cancer cells, breast cancer cells, and/or prostate cancer cells.

In some embodiments, the agent is an anti-CD47 antibody. In some embodiments, the agent is an anti-PD-1 antibody.

In some embodiments, the combination of agents comprises one or more agents selected from the group consisting of paclitaxel, cisplatin, carboplatin, pemetrexed, 5-FU, gemcitabine, oxaliplatin, docetaxel, and capecitabine.

In one aspect, the disclosure relates to methods of producing an animal comprising a human hemato-lymphoid system. The methods involve engrafting a population of cells comprising human hematopoietic cells or human peripheral blood cells into the animal described herein.

In some embodiments, the human hemato-lymphoid system comprises human cells selected from the group consisting of hematopoietic stem cells, myeloid precursor cells, myeloid cells, dendritic cells, monocytes, granulocytes, neutrophils, mast cells, lymphocytes, and platelets.

In some embodiments, the methods further involve irradiating the animal prior to the engrafting.

In one aspect, the disclosure relates to methods of producing a B2M knockout mouse. The methods involve the steps of:
(a) transforming a mouse embryonic stem cell with a gene editing system that targets endogenous B2M gene, thereby producing a transformed embryonic stem cell;
(b) introducing the transformed embryonic stem cell into a mouse blastocyst;
(c) implanting the mouse blastocyst into a pseudopregnant female mouse; and
(d) allowing the blastocyst to undergo fetal development to term, thereby obtaining the B2M knockout mouse.

In one aspect, the disclosure relates to methods of producing a B2M knockout mouse. The methods involve the steps of:
(a) transforming a mouse embryonic stem cell with a gene editing system that targets endogenous B2M gene, thereby producing a transformed embryonic stem cell;
(b) implanting the transformed embryonic cell into a pseudopregnant female mouse; and
(c) allowing the transformed embryonic cell to undergo fetal development to term, thereby obtaining the B2M knockout mouse.

In some embodiments, the gene editing system comprises a first nuclease comprising a zinc finger protein, a TAL-effector domain, or a single guide RNA (sgRNA) DNA-binding domain that binds to a target sequence in exon 1 of the endogenous B2M gene or upstream of exon 1 of the endogenous B2M gene, and a second nuclease comprising a zinc finger protein, a TAL-effector domain, or a single guide RNA (sgRNA) DNA-binding domain that binds to a sequence in exon 3 of the endogenous B2M gene.

In some embodiments, the nuclease is CRISPR associated protein 9 (Cas9).

In some embodiments, the mouse embryonic stem cell has a NOD/scid background, a NOD/scid nude, or a NOD-Prkdc$^{scid}$ IL-2rγ$^{null}$ background.

In some embodiments, the mouse embryonic stem cell comprises a sequence encoding a human or chimeric protein.

In some embodiments, the human or chimeric protein is PD-1 or CD137.

In some embodiments, the mouse embryonic stem cell has a genome comprising a disruption in the animal's endogenous CD132 gene.

In another aspect, the disclosure relates to a non-human mammalian cell, comprising a disruption, a deletion, or a genetic modification as described herein.

In some embodiments, the cell includes Cas9 mRNA or an in vitro transcript thereof.

In some embodiments, the non-human mammalian cell is a mouse cell. In some embodiments, the cell is a fertilized egg cell. In some embodiments, the cell is a germ cell. In some embodiments, the cell is a blastocyst.

In another aspect, the disclosure relates to methods for establishing a B2M knockout animal model. The methods include the steps of:

(a) providing the cell with a disruption in the endogenous B2M gene, and preferably the cell is a fertilized egg cell;

(b) culturing the cell in a liquid culture medium;

(c) transplanting the cultured cell to the fallopian tube or uterus of the recipient female non-human mammal, allowing the cell to develop in the uterus of the female non-human mammal;

(d) identifying the germline transmission in the offspring of the pregnant female in step (c).

In some embodiments, the establishment of a B2M knockout animal involves a gene editing technique that is based on CRISPR/Cas9.

In some embodiments, the non-human mammal is a mouse. In some embodiments, the non-human mammal in step (c) is a female with false pregnancy.

In one aspect, provided herein is a genetically-modified non-human animal whose genome comprises at least one chromosome comprising a sequence expressing a fusion protein (e.g., a chimeric polypeptide). In some embodiments, the fusion protein comprises all or a part of endogenous B2M protein, and/or all or a part of endogenous FcRn protein. In some embodiments, the fusion protein is any one of the fusion protein described in the disclosure.

In some embodiments, the fusion protein comprises at least 50%, at least 60%, at least 70%, at least 80%, at least 90%, or 100% of the protein activity (e.g., binding to IgG) of a wild-type FcRn protein complex.

In some embodiments, the sequence encoding the fusion protein is operably linked to an endogenous regulatory element (e.g., a promoter) at the endogenous FcRn gene locus in the at least one chromosome. In some embodiments, the sequence encoding the fusion protein is operably linked to an endogenous regulatory element (e.g., a promoter) at the endogenous B2M gene locus in the at least one chromosome.

In another aspect, the disclosure relates to a non-human mammalian cell, comprising a disruption, a deletion, or a genetic modification as described herein.

In some embodiments, the cell includes Cas9 mRNA or an in vitro transcript thereof.

In some embodiments, the non-human mammalian cell is a mouse cell. In some embodiments, the cell is a fertilized egg cell. In some embodiments, the cell is a germ cell. In some embodiments, the cell is a blastocyst.

In another aspect, the disclosure relates to a tumor bearing non-human mammal model, characterized in that the non-human mammal model is obtained through the methods as described herein.

The disclosure also relates to a cell or cell line, or a primary cell culture thereof derived from the non-human mammal or an offspring thereof, or the tumor bearing non-human mammal.

The disclosure further relates to the tissue, organ or a culture thereof derived from the non-human mammal or an offspring thereof, or the tumor bearing non-human mammal.

In another aspect, the disclosure relates to a tumor tissue derived from the non-human mammal or an offspring thereof when it bears a tumor, or the tumor bearing non-human mammal.

The disclosure further relates to the use of the non-human mammal or an offspring thereof, or the tumor bearing non-human mammal, the animal model generated through the method as described herein in the development of a product related to an immunization processes of human cells, the manufacture of a human antibody, or the model system for a research in pharmacology, immunology, microbiology and medicine.

The disclosure also relates to the use of the non-human mammal or an offspring thereof, or the tumor bearing non-human mammal, the animal model generated through the method as described herein in the production and utilization of an animal experimental disease model of an immunization processes involving human cells, the study on a pathogen, or the development of a new diagnostic strategy and/or a therapeutic strategy.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 8B shows a flow cytometry detection result from spleen cells of BNDG-B2M/FcRn mice. The cells were stained with PE anti-mouse CD335 (NKp46) (mNKp46) and PerCP/Cy5.5 anti-mouse TCR β chain (mTCR-β).

FIG. 8C shows a flow cytometry detection result from blood cells of BNDG-B2M/FcRn mice. The cells were stained with Brilliant Violet 605™ anti-mouse CD19 (mCD19) and PerCP/Cy5.5 anti-mouse TCR β chain (mTCR-β).

FIG. 8D shows a flow cytometry detection result from blood cells of BNDG-B2M/FcRn mice. The cells were stained with PE anti-mouse CD335 (NKp46) (mNKp46) and PerCP/Cy5.5 anti-mouse TCR β chain (mTCR-β).

FIG. 8E shows a flow cytometry detection result from spleen cells of B-NDG mice. The cells were stained with Brilliant Violet 605™ anti-mouse CD19 (mCD19) and PerCP/Cy5.5 anti-mouse TCR β chain (mTCR-β).

FIG. 8F shows a flow cytometry detection result from spleen cells of B-NDG mice. The cells were stained with PE anti-mouse CD335 (NKp46) (mNKp46) and PerCP/Cy5.5 anti-mouse TCR β chain (mTCR-β).

FIG. 8G shows a flow cytometry detection result from blood cells of B-NDG mice. The cells were stained with Brilliant Violet 605™ anti-mouse CD19 (mCD19) and PerCP/Cy5.5 anti-mouse TCR β chain (mTCR-β).

FIG. 8H shows a flow cytometry detection result from blood cells of B-NDG mice. The cells were stained with PE anti-mouse CD335 (NKp46) (mNKp46) and PerCP/Cy5.5 anti-mouse TCR β chain (mTCR-β).

FIG. 8I shows a flow cytometry detection result from spleen cells of NOD/scid mice. The cells were stained with Brilliant Violet 605™ anti-mouse CD19 (mCD19) and PerCP/Cy5.5 anti-mouse TCR β chain (mTCR-β).

FIG. 8J shows a flow cytometry detection result from spleen cells of NOD/scid mice. The cells were stained with PE anti-mouse CD335 (NKp46) (mNKp46) and PerCP/Cy5.5 anti-mouse TCR β chain (mTCR-β).

FIG. 8K shows a flow cytometry detection result from blood cells of NOD/scid mice. The cells were stained with Brilliant Violet 605™ anti-mouse CD19 (mCD19) and PerCP/Cy5.5 anti-mouse TCR β chain (mTCR-β).

FIG. 8L shows a flow cytometry detection result from blood cells of NOD/scid mice. The cells were stained with PE anti-mouse CD335 (NKp46) (mNKp46) and PerCP/Cy5.5 anti-mouse TCR β chain (mTCR-β).

FIG. 8M shows a flow cytometry detection result from spleen cells of C57BL/6 mice. The cells were stained with Brilliant Violet 605™ anti-mouse CD19 (mCD19) and PerCP/Cy5.5 anti-mouse TCR β chain (mTCR-β).

FIG. 8N shows a flow cytometry detection result from spleen cells of C57BL/6 mice. The cells were stained with PE anti-mouse CD335 (NKp46) (mNKp46) and PerCP/Cy5.5 anti-mouse TCR β chain (mTCR-β).

FIG. 8O shows a flow cytometry detection result from blood cells of C57BL/6 mice. The cells were stained with Brilliant Violet 605™ anti-mouse CD19 (mCD19) and PerCP/Cy5.5 anti-mouse TCR β chain (mTCR-β).

FIG. 12G shows H&E stain result of thymic lobes (in spleen) of B-NDG mice.

FIG. 12H shows H&E stain result of thymic lobes (in spleen) of BNDG-B2M/FcRn mice.

DETAILED DESCRIPTION

Figure 1:
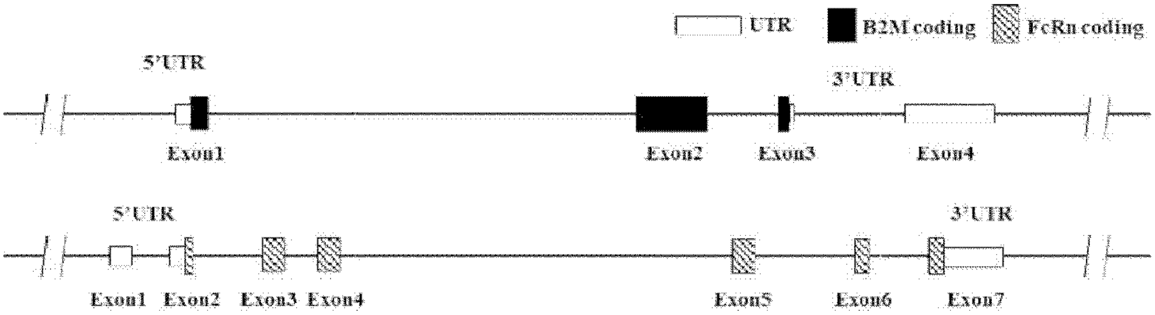
FIG. 1 shows schematic diagrams of mouse B2M gene locus (upper panel) and mouse FcRn gene locus (lower panel).

Immunodeficient animals are an indispensable research tool for studying the mechanism of diseases, and methods of treating such diseases. They can easily accept xenogeneic cells or tissues due to their immunodeficiency, and have been widely used in the research. The commonly used immunodeficient animals include e.g., NOD-Prkdc$^{scid}$ IL-2r$\gamma^{null}$ mice, NOD-Rag 1$^{-/-}$-IL2rg$^{-/-}$ (NRG), Rag 2$^{-/-}$-IL2rg$^{-/-}$ (RG), NOD/scid (NOD-Prkdc$^{scid}$), and NOD/scid nude mice. Among them, NOD-Prkdc$^{scid}$ IL-2r$\gamma^{null}$ mice may be the best recipient mice for transplantation. Some of these mice are described in detail e.g., in Ito et al. "Current advances in humanized mouse models." Cellular & molecular immunology 9.3 (2012): 208; and US20190320631A1, each of which is incorporated herein by reference in its entirety.

The NOD-Prkdc$^{scid}$ IL-2r$\gamma^{null}$ mice (also known as NOD/SCID IL-2r$\gamma^{null}$ mice) have several advantages. In these mice, there is almost no rejection of human cells and tissues, and it is particularly suitable for human cell or tissue transplantation. However, during the reconstruction of the immune system, the NOD-Prkdc$^{scid}$ IL-2r$\gamma^{null}$ mice develop graft-versus-host disease (X-GVHD) over time because of the transplantation of mature T cells into these mice. It has been shown that after 1×10$^6$ to 2×10$^7$ human PBMC are injected into the mouse, xenogeneic graft-versus-host disease (X-GVHD) can be developed within 4 weeks, eventually leading to the death of these mice within about 20-50 days after transplantation. This greatly limits the time period of experiments and can have a negative impact on the results of functional studies.

This disclosure relates to genetically-modified animals which express B2M/FcRn fusion protein, and methods of use thereof. In some embodiments, the animal is an immunodeficient animal (e.g., with NOD-Prkdc$^{scid}$ IL-2r$\gamma^{null}$, NOD-Rag 1$^{-/-}$-IL2rg$^{-/-}$ (NRG), Rag 2$^{-/-}$-IL2rg$^{-/-}$ (RG), NOD/scid (NOD-Prkdc$^{scid}$), or B-NDG background). In some embodiments, the animal has a disruption or deletion of endogenous B2M gene. Experiments described herein show that the animal has a higher survival rate (e.g., than an animal not expressing the B2M/FcRn fusion protein) after human immune cell engraftment, as well as a functional FcRn protein complex to maintain IgG hemostasis, therefore providing a longer time window for determining the efficacy of various therapies (e.g., IgG-based therapies) for human.

In some embodiments, the animal has a disruption or deletion of endogenous B2M gene, therefore does not express endogenous MHC class I protein complex. The major histocompatibility complex (MHC) is essential for the acquired immune system to recognize foreign molecules and is involved in the rejection of foreign tissues and cells. There are two types of major histocompatibility complexes, commonly referred to as MHC class I and MHC class II, which present the polypeptide to the surface of CD8+ T cells or CD4+ T cells, respectively. Human peripheral blood mononuclear cells (PBMC) are often used for immune system reconstruction in NOD-Prkdc$^{scid}$ IL-2r$\gamma^{null}$ mice. More than 99% of peripheral blood cells are T cells. MHC class I molecules may have been involved in the production and development of X-GVHD. B2M is an essential component of the MHC class I protein complex. Because the disruption or deletion of endogenous B2M gene, the animal is less likely to develop X-GVHD and have a better defined genetic background (e.g., less genetic variations among individuals). Furthermore, because these animals have less genetic variation, the results are more reliable.

Because B2M is also an essential component of an FcRn protein complex, lack of B2M expression can lead to in vivo IgG clearance, e.g., clearance of IgG-based therapies. Thus, genetically-modified animals expressing a B2M/FcRn fusion protein described herein and having a disruption or deletion of endogenous B2M gene can be generated to restore IgG homeostasis.

β2 Microglobulin (B2M)

B2M (also known as β2M, β2 microglobulin or beta-2 microglobulin) is a small protein (about 11,800 Dalton), presenting in nearly all nucleated cells and most biological fluids, including serum, urine, and synovial fluid. The human β2M shows 70% amino acid sequence similarity to the murine protein and both of them are located on the syntenic chromosomes. The secondary structure of B2M consists of seven β-strands which are organized into two β-sheets linked by a single disulfide bridge, presenting a classical β-sandwich typical of the immunoglobulin (Ig) domain. B2M has no transmembrane region and contains a distinctive molecular structure called a constant-1 Ig superfamily domain, sharing with other adaptive immune molecules including major histocompatibility complex (MHC) class I and class II. Two evolutionary conserved tryptophan (Trp) residues are important for correct structural fold and function of B2M. Trp60 is exposed to the solvent at the apex of a protein loop and is critical for promoting the association of B2M in MHC I.

Normally, B2M is noncovalently linked with the other polypeptide chain (α chain) to form MHC I or like structures, including MHC I, neonatal Fc receptor (FcRn), a cluster of differentiation 1 (CD1), human hemochromatosis protein (HFE), Qa, and so on. B2M makes extensive contacts with all three domains of the α chain. Thus, the conformation of α chain is highly dependent on the presence of B2M. Although α1 and α2 domains differ among molecules, α3 domain and B2M are relatively conserved, where the intermolecular interaction occurs. A number of residues at the points of contact with B2M are shared among MHC I or like molecules. Furthermore, interactions with α1 and α2 domains are important for the paired association of α3 domain and B2M in the presence of native antigens. B2M can dissociate from such molecules and shed into the serum, where it is transported to the kidneys to be degraded and excreted. An 88-kD protein (calnexin) associates rapidly and quantitatively with newly synthesized murine MHC I molecules within the endoplasmic reticulum. Both B2M and peptide are required for efficient calnexin dissociation and subsequent MHC I transport.

B2M can stabilize the tertiary structure of the MHC I or like molecules. It is also extensively involved in the functional regulation of survival, proliferation, apoptosis, and even metastasis in cancer cells.

A detailed description of B2M and its function can be found, e.g., in Li et al., "The implication and significance of beta 2 microglobulin: A conservative multifunctional regulator." *Chinese Medical Journal* 129.4 (2016): 448; Wang et al., "Targeted Disruption of the β2-Microglobulin Gene Minimizes the Immunogenicity of Human Embryonic Stem Cells," *Stem Cells Translational Medicine* 4.10 (2015): 1234-1245; each of which is incorporated herein by reference in its entirety.

In mice, B2M gene locus has four exons, exon 1, exon 2, exon 3, and exon 4 (FIG. 1). The mouse B2M protein also has a signal peptide. The nucleotide sequence for mouse B2M mRNA is NM_009735.3 (SEQ ID NO: 1), the amino acid sequence for mouse B2M is NP_033865.2 (SEQ ID NO: 2). The location for each exon and each region in the mouse B2M nucleotide sequence and amino acid sequence is listed below:

TABLE 1

| Mouse B2M (approximate location) | NM_009735.3 858 bp (SEQ ID NO: 1) | NP_033865.2 119 aa (SEQ ID NO: 2) |
|---|---|---|
| Exon 1 | 1-118 | 1-22 |
| Exon 2 | 119-397 | 23-115 |
| Exon 3 | 398-426 | 116-119 |
| Exon 4 | 427-858 | Non-coding |
| Signal peptide | 52-111 | 1-20 |
| Chain (mature protein) | 112-408 | 21-119 |
| Donor region in Example | 112-408 | 21-119 |

The mouse B2M gene (Gene ID: 12010) is located in Chromosome 2 of the mouse genome, which is located from 122,147,687 to 122,153,082 of NC_000068.7 (GRCm38.p6 (GCF_000001635.26)). The 5'-UTR is from 122,147,686 to 122,147,736, exon 1 is from 122,147,686 to 122,147,804, the first intron is from 122,147,805 to 122,150,872, exon 2 is from 122,150,873 to 122,151,151, the second intron is from 122,151,152 to 122,151,646, exon 3 is from 122,151,647 to 122,151,675, the third intron is from 122,151,676 to 122,152,650, exon 4 is from 122,152,651 to 122,153,083, and the 3'-UTR is from 122,151,661 to 122,153,083, based on transcript NM_009735.3. All relevant information for mouse B2M locus can be found in the NCBI website with Gene ID: 12010, which is incorporated by reference herein in its entirety.

B2M genes, proteins, and locus of the other species are also known in the art. For example, the gene ID for B2M in *Rattus norvegicus* (rat) is 24223, the gene ID for B2M in *Macaca mulatta* (Rhesus monkey) is 712428, the gene ID for B2M in *Equus caballus* (horse) is 100034203, and the gene ID for B2M in *Sus scrofa* (pig) is 397033. The relevant information for these genes (e.g., intron sequences, exon sequences, amino acid residues of these proteins) can be found, e.g., in NCBI database, which is incorporated by reference herein in its entirety.

The present disclosure provides mouse B2M nucleotide sequences and/or amino acid sequences. In some embodiments, the entire sequence of mouse exon 1, exon 2, exon 3, and/or exon 4, is inserted at an endogenous (e.g., mouse) FcRn gene locus. In some embodiments, a "region" or "portion" of mouse exon 1, exon 2, exon 3, and/or exon 4, is inserted into an endogenous (e.g., mouse) FcRn gene locus. In some embodiments, the entire sequence of mouse B2M signal peptide and/or mature protein is fused to (e.g., inserted between any two amino acids of) an endogenous (e.g., mouse) FcRn protein. In some embodiments, a "region" or "portion" of mouse B2M signal peptide and/or mature protein is fused to (e.g., inserted between any two amino acids of) an endogenous (e.g., mouse) FcRn protein. The term "region" or "portion" can refer to at least 1, 2, 3, 4, 5, 6, 7, 8, 9, 10, 20, 30, 40, 50, 60, 70, 80, 90, 100, 110, 120, 130, 140, 150, 160, 170, 180, 190, 200, 250, or 300 nucleotides, or at least 1, 2, 3, 4, 5, 6, 7, 8, 9, 10, 20, 30, 40, 50, 60, 70, 80, 90, or 100 amino acid residues. In some embodiments, the "region" or "portion" can be at least 50%, 55%, 60%, 65%, 70%, 75%, 80%, 85%, 90%, 95%, or 99% identical to exon 1, exon 2, exon 3, exon 4, signal peptide, or mature protein. In some embodiments, a region, a portion, or the entire sequence of mouse exon 1, exon 2, exon 3, and/or exon 4 are inserted at an endogenous (e.g., mouse) FcRn gene locus. In some embodiments, the inserted sequence does not include introns (e.g., intron 1, intron 2, and/or intron 3). In some embodiments, the inserted sequence is a cDNA sequence that is identical to or derived from nucleic acids 112-408 of NM_009735.3 (SEQ ID NO: 1).

In some embodiments, the present disclosure is related to a genetically-modified, non-human animal whose genome comprises a B2M/FcRn fusion gene sequence. In some embodiments, the B2M/FcRn fusion gene sequence encodes a fusion protein including an endogenous B2M polypeptide (or endogenous B2M). In some embodiments, the endogenous B2M polypeptide does not include a signal peptide (e.g., a signal peptide that is at least 80%, 85%, 90%, 95%, or 100% identical to, or corresponds to, amino acids 1-20 of SEQ ID NO: 2). In some embodiments, the endogenous B2M polypeptide has a sequence that is at least 80%, 85%, 90%, 95%, or 100% identical to amino acids 21-119 of SEQ ID NO: 2.

In some embodiments, the present disclosure also provides an endogenous B2M nucleotide sequence and/or amino acid sequences, wherein in some embodiments, at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% of the sequence are identical to or derived from mouse B2M mRNA sequence (e.g., SEQ ID NO: 1), mouse B2M amino acid sequence (e.g., SEQ ID NO: 2), or a portion thereof (amino acids 21-119 of SEQ ID NO: 2).

In some embodiments, the B2M/FcRn fusion gene sequence as described herein is operably linked to a promotor or regulatory element, e.g., an endogenous mouse B2M promotor, an inducible promoter, an enhancer, and/or mouse or human regulatory elements.

In some embodiments, the B2M/FcRn fusion gene sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is different from part of or the entire mouse B2M nucleotide sequence (e.g., exon 1, exon 2, exon 3, exon 4, or NM_009735.3 (SEQ ID NO: 1)).

In some embodiments, the B2M/FcRn fusion gene sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is the same as part of or the entire mouse B2M nucleotide sequence (e.g., exon 1, exon 2, exon 3, exon 4, or NM_009735.3 (SEQ ID NO: 1)).

In some embodiments, the amino acid sequence encoded by the B2M/FcRn fusion gene sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is different from part of or the entire mouse B2M amino acid sequence (e.g., amino acids encoded by exon 1, exon 2, exon 3, and/or exon 4 of NM_009735.3 (SEQ ID NO: 1); or NP_033865.2 (SEQ ID NO: 2)).

In some embodiments, the amino acid sequence encoded by the B2M/FcRn fusion gene sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is the same as part of or the entire mouse B2M amino acid sequence (e.g., amino acids encoded by exon 1, exon 2, exon 3, and/or exon 4 of NM_009735.3 (SEQ ID NO: 1); or NP_033865.2 (SEQ ID NO: 2)).

Neonatal Fc Receptor (FcRn)

The neonatal Fc receptor (also known as FcRn, IgG receptor FcRn large subunit p51, or Brambell receptor) is a protein that in humans is encoded by the FCGRT gene. It is an Fc receptor which is similar in structure to the MHC class I molecule and also associates with beta-2-microglobulin. Further studies revealed a similar receptor in humans, leading to the naming as a neonatal Fc receptor. In humans, however, it is found in the placenta to help facilitate transport of mother's IgG to the growing fetus. It has also been shown to play a role in monitoring IgG and serum albumin turnover. Neonatal Fc receptor expression is up-regulated by the proinflammatory cytokine, TNF-α, and down-regulated by IFN-γ.

FcRn has been shown to interact with Human serum albumin. FcRn-mediated transcytosis of IgG across epithelial cells is possible because FcRn binds IgG at acidic pH (<6.5) but not at neutral or higher pH. Therefore, FcRn can bind IgG from the slightly acidic intestinal lumen and ensure efficient, unidirectional transport to the basolateral side where the pH is neutral to slightly basic.

FcRn extends the half-life of IgG and serum albumin by reducing lysosomal degradation in endothelial cells[8] and bone-marrow derived cells. IgG, serum albumin and other serum proteins are continuously internalized through pinocytosis. Generally, serum proteins are transported from the endosomes to the lysosome, where they are degraded. The two most abundant serum proteins, IgG and serum albumin are bound by FcRn at the slightly acidic pH (<6.5), and recycled to the cell surface where they are released at the neutral pH (>7.0) of blood. In this way IgG and serum albumin avoids lysosomal degradation. This mechanism provides an explanation for the greater serum circulation half-life of IgG and serum albumin.

FcRn is expressed on antigen-presenting leukocytes like dendritic cells and is also expressed in neutrophils to help clear opsonized bacteria. In the kidneys, FcRn is expressed on epithelial cells called podocytes to prevent IgG and albumin from clogging the glomerular filtration barrier. Current studies are investigating FcRn in the liver because there are relatively low concentrations of both IgG and albumin in liver bile despite high concentrations in the blood. Studies have shown that FcRn-mediated transcytosis is involved with the trafficking of the HIV-1 virus across genital tract epithelium.

A detailed description of FcRn and its function can be found, e.g., in Pyzik, M. et al., "FcRn: the architect behind the immune and nonimmune functions of IgG and albumin." *The Journal of Immunology* 194.10 (2015): 4595-4603; Pyzik, M., et al. "The neonatal Fc receptor (FcRn): a misnomer?." *Frontiers in Immunology* 10 (2019): 1540; each of which is incorporated herein by reference in its entirety.

In mice, the FcRn (or Fcgrt) gene locus has seven exons, exon 1, exon 2, exon 3, exon 4, exon 5, exon 6, and exon 7 (FIG. 1). The mouse FcRn protein also has a signal peptide, an extracellular region, a transmembrane region, and a cytoplasmic region. Specifically, the extracellular region includes an α1 domain, an α2 domain, an α3 domain, and a connecting peptide. The nucleotide sequence for mouse FcRn mRNA is NM_010189.3 (SEQ ID NO: 3), the amino acid sequence for mouse FcRn is NP_034319.2 (SEQ ID NO: 4). The location for each exon and each region in the mouse FcRn nucleotide sequence and amino acid sequence is listed below:

TABLE 2

| Mouse FcRn (approximate location) | NM_010189.3 1738 bp (SEQ ID NO: 3) | NP_034319.2 365 aa (SEQ ID NO: 4) |
|---|---|---|
| Exon 1 | 1-183 | Non-coding |
| Exon 2 | 184-454 | 1-22 |
| Exon 3 | 455-712 | 23-108 |
| Exon 4 | 713-988 | 109-200 |
| Exon 5 | 989-1258 | 201-290 |
| Exon 6 | 1259-1375 | 291-329 |
| Exon 7 | 1376-1738 | 330-365 |
| Signal peptide | 388-450 | 1-21 |
| Extracellular | 451-1278 | 22-297 |
| Transmembrane | 1279-1350 | 298-321 |
| Cytoplasmic | 1351-1482 | 322-365 |
| Insert site in Example | Between 450 and 451 bp | Between 21 and 22 aa |

The mouse FcRn gene (Gene ID: 14132) is located in Chromosome 7 of the mouse genome, which is located from 45,092,993 to 45,103,822, of NC_000073.6 (GRCm38.p6 (GCF_000001635.26)). The 5'-UTR is from 45,103,851 to 45,103,070, exon 1 is from 45,103,851 to 45,103,640, the first intron is from 45,103,851 to 45,103,274, exon 2 is from 45,103,273 to 45,103,003, the second intron is from 45,103,002 to 45,102,672, exon 3 is from 45,102,671 to 45,102,414, the third intron is from 45,102,413 to 45,102,186, exon 4 is from 45,102,185 to 45,101,910, the fourth intron is from 45,101,909 to 45,095,430, exon 5 is from 45,095,429 to 45,095,160, the fifth intron is from 45,095,159 to 45,093,899, exon 6 is from 45,093,898 to 45,093,782, the sixth intron is from 45,093,781 to 45,093,356, exon 7 is from 45,093,355 to 45,092,990, and the 3'-UTR is from 45,093,245 to 45,092,990, based on transcript NM_010189.3. All relevant information for mouse FcRn locus can be found in the NCBI website with Gene ID: 14132, which is incorporated by reference herein in its entirety.

According to the UniProt Database (UniProt ID: Q61559), the extracellular region (not including signal peptide) of mouse FcRn corresponds to amino acids 22-297 of SEQ ID NO: 4; the transmembrane region of mouse FcRn corresponds to amino acids 298-321 of SEQ ID NO: 4; the cytoplasmic region of mouse FcRn corresponds to amino acids 322-365 of SEQ ID NO: 4; the signal peptide of mouse FcRn corresponds to amino acids 1-21 of SEQ ID NO: 4. Specifically, there is an Ig-like Cl-type domain within the extracellular region of mouse FcRn, which corresponds to amino acids 202-289 of SEQ ID NO: 4. In addition, the extracellular region includes, from N-terminus to C-terminus, an alpha-1 (α1) domain, an alpha-2 (α2) domain, an alpha-3 (α3) domain, and a connecting peptide. The alpha-1 domain corresponds to amino acids 22-110 of SEQ ID NO: 4; the alpha-2 domain corresponds to amino acids 111-200 of SEQ ID NO: 4; the alpha-3 domain corresponds to amino acids 201-290 of SEQ ID NO: 4; and the connecting peptide corresponds to amino acids 291-297 of SEQ ID NO: 4.

FcRn (or Fcgrt) molecule genes, proteins, and locus of the other species are also known in the art. For example, the gene ID for B2M in *Rattus norvegicus* (rat) is 29558, the gene ID for B2M in *Macaca fascicularis* (crab-eating macaque) is 102128913, the gene ID for B2M in *Equus caballus* (horse) is 100147583, and the gene ID for B2M in *Sus scrofa* (pig) is 397399. The relevant information for these genes (e.g., intron sequences, exon sequences, amino acid residues of these proteins) can be found, e.g., in NCBI database, which is incorporated by reference herein in its entirety.

The present disclosure provides mouse FcRn nucleotide sequence and/or amino acid sequences. This disclosure also relates to genetically-modified animals which express a fusion protein including a B2M polypeptide (e.g., an endogenous B2M polypeptide) and an FcRn polypeptide (e.g., an endogenous FcRn polypeptide). In some embodiments, the B2M polypeptide and the FcRn polypeptide can interact with each other, forming a functional FcRn complex. As used herein, the term "FcRn complex" or "FcRn protein complex" refers to the complex formed by the B2M polypeptide and the FcRn polypeptide. In some embodiments, the B2M polypeptide and the FcRn polypeptide are fused together, optionally via a linker peptide. In some embodiments, a nucleotide sequence encoding all or part of a B2M protein (e.g., an endogenous B2M protein) is inserted between any two nucleotides (e.g., corresponding to positions 450 and 451 of NM_010189.3 (SEQ ID NO: 3)) of an endogenous FcRn gene locus, thereby generating a B2M/FcRn fusion gene sequence. In some embodiments, the insertion site is located within exon 1, exon 2, exon 3, exon 4, exon 5, exon 6, and/or exon 7 of mouse FcRn gene. In some embodiments, the insertion site is located within exon 2 of mouse FcRn gene. In some embodiments, the B2M/FcRn fusion gene sequence encodes a fusion protein including an endogenous FcRn polypeptide (or endogenous FcRn). In some embodiments, the fusion protein includes an endogenous B2M polypeptide that is inserted between any two amino acid residues (e.g., corresponding to amino acids 21 and 22 of NP_034319.2 (SEQ ID NO: 4)) of the endogenous FcRn polypeptide. In some embodiments, the endogenous FcRn polypeptide includes the entire sequence, a "portion", or a "region" thereof, of signal peptide, extracellular region (e.g., α1 domain, α2 domain, α3 domain, and/or connecting peptide), transmembrane region, and/or cytoplasmic region of mouse FcRn protein. The term "region" or "portion" can refer to at least 1, 2, 3, 4, 5, 6, 7, 8, 9, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, or 360 amino acid residues. In some embodiments, the "region" or "portion" can be at least 50%, 55%, 60%, 65%, 70%, 75%, 80%, 85%, 90%, 95%, or 99% identical to signal peptide, extracellular region (e.g., α1 domain, α2 domain, α3 domain, and/or connecting peptide), transmembrane region, and/or cytoplasmic region. In some embodiments, the endogenous FcRn polypeptide includes a signal peptide (e.g., a signal peptide that is at least 80%, 85%, 90%, 95%, or 100% identical to, or corresponds to, amino acids 1-21 of SEQ ID NO: 4). In some embodiments, the endogenous FcRn polypeptide does not include a signal peptide (e.g., a signal peptide that is at least 80%, 85%, 90%, 95%, or 100% identical to, or corresponds to, amino acids 1-21 of SEQ ID NO: 4). In some embodiments, the endogenous FcRn polypeptide includes a sequence that is at least 80%, 85%, 90%, 95%, or 100% identical to amino acids 22-365 of SEQ ID NO: 4.

In some embodiments, the present disclosure also provides a B2M/FcRn fusion gene sequence. In some embodiments, at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% of the sequence is identical to or derived from SEQ ID NO: 5, or a portion thereof. In some embodiments, the present disclosure also provides a corresponding fusion protein sequence. In some embodiments, at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% of the sequence is identical to or derived from SEQ ID NO: 6, or a portion thereof.

In some embodiments, the B2M/FcRn fusion gene sequence as described herein are operably linked to a promotor or regulatory element, e.g., an endogenous mouse FcRn promotor, an inducible promoter, an enhancer, and/or mouse or human regulatory elements.

In some embodiments, the B2M/FcRn fusion gene sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is different from part of or the entire mouse FcRn nucleotide sequence (e.g., exon 1, exon 2, exon 3, exon 4, exon 5, exon 6, exon 7, or NM_010189.3 (SEQ ID NO: 3)).

In some embodiments, the B2M/FcRn fusion gene sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is the same as part of or the entire mouse FcRn nucleotide sequence (e.g., exon 1, exon 2, exon 3, exon 4, exon 5, exon 6, exon 7, or NM_010189.3 (SEQ ID NO: 3)).

In some embodiments, the amino acid sequence encoded by the B2M/FcRn fusion gene sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is different from part of or the entire mouse FcRn amino acid sequence (e.g., amino acids encoded by exon 1, exon 2, exon 3, exon 4, exon 5, exon 6, and/or exon 7, of NM_010189.3 (SEQ ID NO: 3); or NP_034319.2 (SEQ ID NO: 4)).

In some embodiments, the amino acid sequence encoded by the B2M/FcRn fusion gene sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is the same as part of or the entire mouse FcRn amino acid sequence (e.g., amino acids encoded by exon 1, exon 2, exon 3, exon 4, exon 5, exon 6, and/or exon 7 of NM_010189.3 (SEQ ID NO: 3); or NP_034319.2 (SEQ ID NO: 4)).

The disclosure also provides an amino acid sequence that has a homology of at least 90% with, or at least 90% identical to the sequence shown in SEQ ID NO: 2, 4, 6, 40, or 41, and has protein activity. In some embodiments, the homology with the sequence shown in SEQ ID NO: 2, 4, 6, 40, 41, or 42 is at least about 90%, 91%, 92%, 93%, 94%, 95%, 96%, 97%, 98%, or at least 99%. In some embodiments, the foregoing homology is at least about 60%, 61%, 62%, 63%, 64%, 65%, 66%, 67%, 68%, 69%, 70%, 71%, 72%, 73%, 74%, 75%, 80%, or 85%.

In some embodiments, the percentage identity with the sequence shown in SEQ ID NO: 2, 4, 6, 40, 41, or 42 is at least about 90%, 91%, 92%, 93%, 94%, 95%, 96%, 97%, 98%, or at least 99%. In some embodiments, the foregoing percentage identity is at least about 60%, 61%, 62%, 63%, 64%, 65%, 66%, 67%, 68%, 69%, 70%, 71%, 72%, 73%, 74%, 75%, 80%, or 85%.

The disclosure also provides a nucleotide sequence that has a homology of at least 90%, or at least 90% identical to the sequence shown in SEQ ID NO: 1, 3, 5, 9, 43, or 45, and encodes a polypeptide that has protein activity. In some embodiments, the homology with the sequence shown in SEQ ID NO: 1, 3, 5, 7, 8, 9, 43, 44, or 45 is at least about 90%, 91%, 92%, 93%, 94%, 95%, 96%, 97%, 98%, or at least 99%. In some embodiments, the foregoing homology is at least about 50%, 55%, 60%, 65%, 66%, 67%, 68%, 69%, 70%, 71%, 72%, 73%, 74%, 75%, 80%, or 85%.

In some embodiments, the percentage identity with the sequence shown in SEQ ID NO: 1, 3, 5, 7, 8, 9, 43, 44, or 45 is at least about 90%, 91%, 92%, 93%, 94%, 95%, 96%, 97%, 98%, or at least 99%. In some embodiments, the foregoing percentage identity is at least about 50%, 55%, 60%, 65%, 66%, 67%, 68%, 69%, 70%, 71%, 72%, 73%, 74%, 75%, 80%, or 85%.

The disclosure also provides a nucleic acid sequence that is at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% identical to any nucleotide sequence as described herein, and an amino acid sequence that is at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% identical to any amino acid sequence as described herein. In some embodiments, the disclosure relates to nucleotide sequences encoding any peptides that are described herein, or any amino acid sequences that are encoded by any nucleotide sequences as described herein. In some embodiments, the nucleic acid sequence is less than 10, 20, 30, 40, 50, 60, 70, 80, 90, 100, 110, 120, 130, 150, 200, 250, 300, 350, 400, 500, or 600 nucleotides. In some embodiments, the amino acid sequence is less than 5, 6, 7, 8, 9, 10, 20, 30, 40, 50, 60, 70, 80, 90, 100, 110, 120, 130, 140, 150, 160, 170, 180, 190, or 200 amino acid residues.

In some embodiments, the amino acid sequence (i) comprises an amino acid sequence; or (ii) consists of an amino acid sequence, wherein the amino acid sequence is any one of the sequences as described herein.

In some embodiments, the nucleic acid sequence (i) comprises a nucleic acid sequence; or (ii) consists of a nucleic acid sequence, wherein the nucleic acid sequence is any one of the sequences as described herein.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences. For example, the comparison of sequences and determination of percent identity between two sequences can be accomplished using a Blossum 62 scoring matrix with a gap penalty of 12, a gap extend penalty of 4, and a frameshift gap penalty of 5.

The percentage of residues conserved with similar physicochemical properties (percent homology), e.g. leucine and isoleucine, can also be used to measure sequence similarity. Families of amino acid residues having similar physicochemical properties have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). The homology percentage, in many cases, is higher than the identity percentage.

Cells, tissues, and animals (e.g., mouse) are also provided that comprise the nucleotide sequences as described herein, as well as cells, tissues, and animals (e.g., mouse) that express the fusion protein described herein from an endogenous non-human FcRn gene locus.

Genetically Modified Animals

As used herein, the term "genetically-modified non-human animal" refers to a non-human animal having a modified sequence (e.g., insertion of endogenous B2M gene into an endogenous FcRn gene locus as described herein) in at least one chromosome of the animal's genome. In some embodiments, at least one or more cells, e.g., at least 1%, 2%, 3%, 4%, 5%, 10%, 20%, 30%, 40%, 50% of cells of the genetically-modified non-human animal have the modified sequence in its genome. The cell having the modified sequence can be various kinds of cells, e.g., an endogenous cell, a somatic cell, an immune cell, a T cell, a B cell, a germ cell, a blastocyst, or an endogenous tumor cell. In some embodiments, genetically-modified non-human animals are provided that comprise an inserted B2M gene sequence at the endogenous FcRn gene locus. The animals are generally able to pass the modification to progeny, i.e., through germline transmission.

In some embodiments, the genetically-modified non-human animal does not express an endogenous B2M (e.g., mouse B2M). In some embodiments, the genetically-modified non-human animal does not express a functional endogenous B2M (e.g., mouse B2M). In some embodiments, the genetically-modified non-human animal does not express an endogenous FcRn molecule (e.g., mouse FcRn). In some embodiments, the genetically-modified non-human animal does not express a functional endogenous FcRn molecule (e.g., mouse FcRn). In some embodiments, the genetically-modified non-human animal does not express a functional endogenous MHC protein complex (e.g., endogenous MHC class I protein complex). In some embodiments, the genetically-modified non-human animal does not express a functional endogenous FcRn protein complex.

In some embodiments, the genetically-modified non-human animal described herein is immunodeficient. In some embodiments, the animal has a NOD-Prkdc$^{scid}$ IL-2r$\gamma^{null}$, NOD-Rag $1^{-/-}$-IL2rg$^{-/-}$ (NRG), Rag $2^{-/-}$-IL2rg$^{-/-}$ (RG), or NOD/scid (NOD-Prkdc$^{scid}$) background.

In some embodiments, the genetically-modified non-human animal described herein (e.g., mouse) have a disrupted endogenous B2M gene. In some embodiments, the genetically-modified non-human animal described herein (e.g., mouse) expresses a dysfunctional endogenous B2M protein (e.g., mouse B2M). In some embodiments, the genetically-modified non-human animal described herein (e.g., mouse) expresses a dysfunctional endogenous MHC protein complex.

As used herein, the term "leukocytes" or "white blood cells" include T cells (CD3+; mCD19−/mTCR-β+; and/or mNKp46−/mTCR-β+ cells), B cells (mCD19+/mTCR-β− cells), NK cells (mNKp46+/mTCR-β− cells), microphages (mF4-80+ cells), dendritic cells (mCD11c+/mLy6c− cells), and monocytes (mCD11c−/mLy6c+ cells). All leukocytes have nuclei, which distinguishes them from the anucleated red blood cells (RBCs) and platelets. CD45, also known as leukocyte common antigen (LCA), is a cell surface marker for leukocytes. Lymphocyte is a subtype of leukocyte.

In some embodiments, the genetically-modified non-human animal described herein has one or more of the following characteristics:

(a) the percentage of T cells is less than 2%, less than 1.5%, less than 1%, or less than 0.5% of spleen or blood cells (e.g., CD45+ cells) in the animal;

(b) the percentage of B cells is less than 0.2%, less than 0.15%, less than 0.1%, less than 0.05%, or less than 0.02% of spleen or blood cells (e.g., CD45+ cells) in the animal;

(c) the percentage of NK cells is less than 1%, or less than 0.5% of spleen or blood cells (e.g., CD45+ cells) in the animal;

(d) the percentage of macrophages is less than 45%, less than 40%, or less than 35% of bone marrow (BM) cells (e.g., CD45+ cells); less than 25%, less than 20%, or less than 17% of blood cells (e.g., CD45+ cells); and/or less than 5%, less than 4%, or less than 3% of spleen cells (e.g., CD45+ cells) in the animal; and (e) the percentage of DC cells is less than 15%, less than 13%, or less than 11% of spleen cells (e.g., CD45+ cells); less than 2.3%, less than 2.1%, or less than 1.9% of blood cells (e.g., CD45+ cells); and/or less than 1%, less than 0.8%, or less than 0.6% of bone marrow (BW) cells (e.g., CD45+ cells) in the animal; and (f) the percentage of monocytes is less than 25%, less than 23%, or less than 21% of spleen cells (e.g., CD45+ cells); less than 20%, less than 16%, or less than 14% of blood cells (e.g., CD45+ cells); and/or less than 10%, less than 8%, or less than 6% of bone marrow (BW) cells (e.g., CD45+ cells) in the animal.

In some embodiments, genetically-modified non-human animal described herein has one or more developmental defects of immune organs, e.g., in thymus.

In some embodiments, the genetically-modified non-human animal is a mouse. In some embodiments, the genetically-modified non-human animal is a B-NDG mouse or has a B-NDG background. Details of B-NDG mice can be found, e.g., in PCT/CN2018/079365; U.S. Ser. No. 10/820,580B2, each of which is incorporated herein by reference in its entirety. In some embodiments, the genetically modified animal is a NSG mouse or NOG mouse. A detailed description of the NSG mice and NOD mice can be found, e.g., in Ishikawa et al. "Development of functional human blood and immune systems in NOD/scid/IL2 receptor γ chainnull mice." Blood 106.5 (2005): 1565-1573; Katano et al. "NOD-Rag2null IL-2Rγnull mice: an alternative to NOG mice for generation of humanized mice." Experimental animals 63.3 (2014): 321-330, both of which are incorporated herein by reference in the entirety.

In one aspect, the genetically-modified non-human animal (e.g., mouse) is engrafted with human hematopoietic stem cells to develop a human immune system.

In some embodiments, the average percentage of human leukocytes (or CD45+ cells) in the animal is at least or about 10%, 15%, 20%, 25%, 30%, 35%, 40%, 45%, 50%, 55%, or 60% of the total live cells (e.g., from blood after lysis of red blood cells) in the animal. In some embodiments, the average percentage of human leukocytes (or CD45+ cells) in the animal is at least 50%, at least 60%, at least 70%, at least 80%, at least 90%, at least 100%, at least 110%, at least 120%, at least 130%, at least 140%, or at least 150% as compared to that of an animal with B-NDG background (e.g., a B-NDG mouse) engrafted with human hematopoietic stem cells to develop a human immune system. In some embodiments, the average percentage of human leukocytes (or CD45+ cells) is determined at about 2 weeks, about 3 weeks, about 4 weeks, about 5 weeks, about 6 weeks, about 7 weeks, about 8 weeks, about 9 weeks, about 10 weeks, about 11 weeks, about 12 weeks, or about 13 weeks after being engrafted.

In some embodiments, the average percentage of human T cells (or CD45+CD3+ cells) in the animal is at least or about 50%, 55%, 60%, 65%, 70%, 75%, 80%, 85%, 90%, or 95% of the human leukocytes (or CD45+ cells) in the animal. In some embodiments, the average percentage of human T cells (or CD45+CD3+ cells) in the animal is at least 50%, at least 60%, at least 70%, at least 80%, at least 90%, at least 100%, at least 110%, at least 120%, at least 130%, at least 140%, or at least 150% as compared to that of an animal with B-NDG background (e.g., a B-NDG mouse) engrafted with human hematopoietic stem cells to develop a human immune system. In some embodiments, the average percentage of human leukocytes (or CD45+CD3+ cells) is determined at about 2 weeks, about 3 weeks, about 4 weeks, about 5 weeks, about 6 weeks, about 7 weeks, about 8 weeks, about 9 weeks, about 10 weeks, about 11 weeks, about 12 weeks, or about 13 weeks after being engrafted.

In some embodiments, the average body weight of the animal is at least or about 18 g, 19 g, 20 g, 21 g, 22 g, 23 g, 24 g, 25 g, 26 g, or 27 g after about 2 weeks, about 3 weeks, about 4 weeks, about 5 weeks, about 6 weeks, about 7 weeks, about 8 weeks, about 9 weeks, about 10 weeks, about 11 weeks, about 12 weeks, or about 13 weeks of engraftment. In some embodiments, the average body weight of the animal is at least 50%, at least 60%, at least 70%, at least 80%, at least 90%, at least 100%, at least 110%, at least 120%, at least 130%, at least 140%, or at least 150% as compared to that of an animal with B-NDG background (e.g., a B-NDG mouse) engrafted with human hematopoietic stem cells to develop a human immune system.

In some embodiments, the survival rate of the genetically-modified animal (e.g., mouse) is at least or about 20%, 25%, 30%, 35%, 40%, 45%, 50%, 55%, 60%, 65%, 70%, 75%, 80%, 85%, 90%, 95%, or 100% after about 50 days, about 55 days, about 60 days, about 65 days, about 70 days, about 75 days, or about 80 days of the engraftment. In some embodiments, the survival rate of the genetically-modified animal (e.g., mouse) is at least or about 10%, 20%, 30%, 40%, 50%, 60%, 70%, 80%, 90%, 1-fold, 2-fold, 3-fold, 5-fold, or 10-fold higher than that of an animal with B-NDG background (e.g., a B-NDG mouse) after about 50 days, about 55 days, about 60 days, about 65 days, about 70 days, about 75 days, or about 80 days of the engraftment.

The genetically modified non-human animal can also be various other animals, e.g., a rat, rabbit, pig, bovine (e.g., cow, bull, buffalo), deer, sheep, goat, chicken, cat, dog, ferret, primate (e.g., marmoset, rhesus monkey). For the non-human animals where suitable genetically modifiable ES cells are not readily available, other methods are employed to make a non-human animal comprising the genetic modification. Such methods include, e.g., modifying a non-ES cell genome (e.g., a fibroblast or an induced pluripotent cell) and employing nuclear transfer to transfer the modified genome to a suitable cell, e.g., an oocyte, and gestating the modified cell (e.g., the modified oocyte) in a non-human animal under suitable conditions to form an embryo. These methods are known in the art, and are described, e.g., in A. Nagy, et al., "Manipulating the Mouse Embryo: A Laboratory Manual (Third Edition)," Cold Spring Harbor Laboratory Press, 2003, which is incorporated by reference herein in its entirety.

In one aspect, the animal is a mammal, e.g., of the superfamily Dipodoidea or Muroidea. In some embodiments, the genetically modified animal is a rodent. The rodent can be selected from a mouse, a rat, and a hamster. In some embodiment, the rodent is selected from the superfamily Muroidea. In some embodiments, the genetically modified animal is from a family selected from Calomyscidae (e.g., mouse-like hamsters), Cricetidae (e.g., hamster, New World rats and mice, voles), Muridae (true mice and rats, gerbils, spiny mice, crested rats), Nesomyidae (climbing mice, rock mice, with-tailed rats, *malagasy* rats and mice), Platacanthomyidae (e.g., spiny dormice), and Spalacidae (e.g., mole rates, bamboo rats, and zokors). In some embodiments, the genetically modified rodent is selected from a true mouse or rat (family Muridae), a gerbil, a spiny mouse, and a crested rat. In one embodiment, the non-human animal is a mouse.

In some embodiments, the animal is a mouse of a strain selected from BALB/c, A, A/He, A/J, A/WySN, AKR, AKR/A, AKR/J, AKR/N, TA1, TA2, RF, SWR, C3H, C57BR, SJL, C57L, DBA/2, KM, NIH, ICR, CFW, FACA, C57BL/A, C57BL/An, C57BL/GrFa, C57BL/KaLwN, C57BL/6, C57BL/6J, C57BL/6ByJ, C57BL/6NJ, C57BL/10, C57BL/10ScSn, C57BL/10Cr, C57BL/Ola, C57BL, C58, CBA/Br, CBA/Ca, CBA/J, CBA/st, and CBA/H. In some embodiments, the mouse is a 129 strain selected from the group consisting of a strain that is 129P1, 129P2, 129P3, 129X1, 129S1 (e.g., 12951/SV, 12951/SvIm), 129S2, 129S4, 129S5, 12959/SvEvH, 129S6 (129/SvEvTac), 129S7, 129S8, 129T1, 129T2. These mice are described, e.g., in Festing et al., Revised nomenclature for strain 129 mice, Mammalian Genome 10:836 (1999); Auerbach et al., Establishment and Chimera Analysis of 129/SvEv- and C57BL/6-Derived Mouse Embryonic Stem Cell Lines (2000), both of which are incorporated herein by reference in the entirety. In some embodiments, the genetically modified mouse is a mix of the 129 strain and the C57BL/6 strain. In some embodiments, the mouse is a mix of the 129 strains, or a mix of the BL/6 strains. In some embodiment, the mouse is a BALB strain, e.g., BALB/c strain. In some embodiments, the mouse is a mix of a BALB strain and another strain. In some embodiments, the mouse is from a hybrid line (e.g., 50% BALB/c-50% 12954/Sv; or 50% C57BL/6-50% 129).

In some embodiments, the animal is a rat. The rat can be selected from a Wistar rat, an LEA strain, a Sprague Dawley strain, a Fischer strain, F344, F6, and Dark Agouti. In some embodiments, the rat strain is a mix of two or more strains selected from the group consisting of Wistar, LEA, Sprague Dawley, Fischer, F344, F6, and Dark Agouti.

The animal can have one or more other genetic modifications, and/or other modifications, that are suitable for the particular purpose for which the animal expressing the B2M/FcRn fusion protein as described herein is made or used. For example, suitable mice for maintaining a xenograft (e.g., a human cancer or tumor), can have one or more modifications that compromise, inactivate, or destroy the immune system of the non-human animal in whole or in part. Compromise, inactivation, or destruction of the immune system of the non-human animal can include, for example, destruction of hematopoietic cells and/or immune cells by chemical means (e.g., administering a toxin), physical means (e.g., irradiating the animal), and/or genetic modification (e.g., knocking out one or more genes).

Non-limiting examples of such mice include, e.g., NOD mice, SCID mice, NOD/scid mice, nude mice, NOD/scid nude mice, NOD-Rag $1^{-/-}$-IL2rg$^{-/-}$ (NRG) mice, Rag $2^{-/-}$-IL2rg$^{-/-}$ (RG) mice, B-NDG (NOD-Prkdc$^{scid}$IL-2rγ$^{null}$) mice B2M knockout mice, and Rag1 and/or Rag2, knockout mice. In some embodiments, these mice can optionally be irradiated, or otherwise treated to destroy one or more immune cell types. Thus, in various embodiments, a genetically modified mouse is provided that can include one or more mutations at the endogenous non-human B2M or RcRn gene locus, and further comprises a modification that compromises, inactivates, or destroys the immune system (or one or more cell types of the immune system) of the non-human animal in whole or in part. In some embodiments, modification is, e.g., selected from the group consisting of a modification that results in NOD mice, SCID mice, NOD/scid mice, B-NDG (NOD-Prkdc$^{scid}$ IL-2rγ$^{null}$) mice, nude mice, B2M knockout mice, Rag1 and/or Rag2 knockout mice, and a combination thereof. These genetically modified animals are described, e.g., in US20150106961, PCT/CN2019/072406, and PCT/CN2018/079365; each of which is incorporated herein by reference in its entirety.

Although genetically modified cells are also provided that can comprise the modifications (e.g., disruption, mutations) described herein (e.g., ES cells, somatic cells), in many embodiments, the genetically modified non-human animals comprise the modification of the endogenous B2M and/or FcRn gene locus in the germline of the animal.

Furthermore, the genetically modified animal can be homozygous with respect to the modifications (e.g., insertion of an endogenous B2M gene sequence at an endogenous FcRn gene locus). In some embodiments, the animal can be heterozygous with respect to the modification (e.g., insertion of an endogenous B2M gene sequence at an endogenous FcRn gene locus).

(a) Genetically-Modified Non-Human Animals with B-NDG Background

In one aspect, the disclosure relates to a genetically-modified, non-human animal whose genome comprise a disruption in the animal's endogenous CD132 gene, wherein the disruption of the endogenous CD132 gene comprises deletion of exon 2 of the endogenous CD132 gene.

In some embodiments, the disruption of the endogenous CD132 gene further comprises deletion of exon 1 of the endogenous CD132 gene. In some embodiments, the disruption of the endogenous CD132 gene comprises deletion of part of exon 1 of the endogenous CD132 gene.

In some embodiments, the disruption of the endogenous CD132 gene further comprises deletion of one or more exons or part of exons selected from the group consisting of exon 3, exon 4, exon 5, exon 6, exon 7, and exon 8 of the endogenous CD132 gene. In some embodiments, the disruption of the endogenous CD132 gene comprises deletion of exons 1-8 of the endogenous CD132 gene.

In some embodiments, the disruption of the endogenous CD132 gene further comprises deletion of one or more introns or part of introns selected from the group consisting of intron 1, intron 2, intron 3, intron 4, intron 5, intron 6, and intron 7 of the endogenous CD132 gene.

In some embodiments, the disruption consists of deletion of more than 150 nucleotides in exon 1; deletion of the entirety of intron 1, exon 2, intron 2, exon 3, intron 3, exon 4, intron 4, exon 5, intron 5, exon 6, intron 6, exon 7, intron 7; and deletion of more than 250 nucleotides in exon 8.

In some embodiments, the animal is homozygous with respect to the disruption of the endogenous CD132 gene. In some embodiments, the animal is heterozygous with respect to the disruption of the endogenous CD132 gene.

In some embodiments, the disruption prevents the expression of functional CD132 protein.

In some embodiments, the length of the remaining exon sequences at the endogenous CD132 gene locus is less than 30% of the total length of all exon sequences of the endogenous CD132 gene. In some embodiments, the length of the remaining sequences at that the endogenous CD132 gene locus is less than 15% of the full sequence of the endogenous CD132 gene.

In another aspect, the disclosure relates to a genetically-modified, non-human animal, wherein the genome of the animal does not have exon 2 of CD132 gene at the animal's endogenous CD132 gene locus.

In some embodiments, the genome of the animal does not have one or more exons or part of exons selected from the group consisting of exon 1, exon 3, exon 4, exon 5, exon 6, exon 7, and exon 8. In some embodiments, the genome of the animal does not have one or more introns or part of introns selected from the group consisting of intron 1, intron 2, intron 3, intron 4, intron 5, intron 6, and intron 7.

In one aspect, the disclosure also provides a CD132 knockout non-human animal, wherein the genome of the animal comprises from 5' to 3' at the endogenous CD132 gene locus, (a) a first DNA sequence; optionally (b) a second DNA sequence comprising an exogenous sequence; (c) a third DNA sequence, wherein the first DNA sequence, the optional second DNA sequence, and the third DNA sequence are linked, wherein the first DNA sequence comprises an endogenous CD132 gene sequence that is located upstream of intron 1, the second DNA sequence can have a length of 0 nucleotides to 300 nucleotides, and the third DNA sequence comprises an endogenous CD132 gene sequence that is located downstream of intron 7.

In some embodiments, the first DNA sequence comprises a sequence that has a length (5' to 3') of from 10 to 100 nucleotides (e.g., approximately 10, 20, 30, 40, 50, 60, 70, 80, 90, 100 nucleotides), wherein the length of the sequence refers to the length from the first nucleotide in exon 1 of the CD132 gene to the last nucleotide of the first DNA sequence.

In some embodiments, the first DNA sequence comprises at least 10 nucleotides from exon 1 of the endogenous CD132 gene. In some embodiments, the first DNA sequence has at most 100 nucleotides from exon 1 of the endogenous CD132 gene.

In some embodiments, the third DNA sequence comprises a sequence that has a length (5' to 3') of from 200 to 600 nucleotides (e.g., approximately 200, 250, 300, 350, 400, 450, 500, 550, 600 nucleotides), wherein the length of the sequence refers to the length from the first nucleotide in the third DNA sequence to the last nucleotide in exon 8 of the endogenous CD132 gene.

In some embodiments, the third DNA sequence comprises at least 300 nucleotides from exon 8 of the endogenous CD132 gene. In some embodiments, the third DNA sequence has at most 400 nucleotides from exon 8 of the endogenous CD132 gene.

In one aspect, the disclosure also relates to a genetically-modified, non-human animal produced by a method comprising knocking out one or more exons of endogenous CD132 gene by using (1) a first nuclease comprising a zinc finger protein, a TAL-effector domain, or a single guide RNA (sgRNA) DNA-binding domain that binds to a target sequence in exon 1 of the endogenous CD132 gene or upstream of exon 1 of the endogenous CD132 gene, and (2) a second nuclease comprising a zinc finger protein, a TAL-effector domain, or a single guide RNA (sgRNA) DNA-binding domain that binds to a sequence in exon 8 of the endogenous CD132 gene. In some embodiments, the nuclease is CRISPR associated protein 9 (Cas9). In some embodiments, the animal does not express a functional CD132 protein. In some embodiments, the animal does not express a functional interleukin-2 receptor.

In one aspect, the disclosure relates to a genetically-modified mouse or a progeny thereof, whose genome comprises a disruption in the mouse's endogenous CD132 gene, wherein the disruption of the endogenous CD132 gene comprises deletion of more than 150 nucleotides in exon 1; deletion of the entirety of intron 1, exon 2, intron 2, exon 3, intron 3, exon 4, intron 4, exon 5, intron 5, exon 6, intron 6, exon 7, intron 7; and deletion of more than 250 nucleotides in exon 8. In some embodiments, the animal has an enhanced engraftment capacity of exogenous cells relative to a NSG mouse, a NOG mouse, or a NOD/scid mouse.

(b) Genetically-Modified Non-Human Animals Having a Disruption of Endogenous B2M Gene In some embodiments, genetically-modified non-human animals are provided that comprise a disruption or a deletion at the endogenous B2M locus. The animals are generally able to pass the modification to progeny, i.e., through germline transmission. Details of such animals can be found, e.g., in PCT/CN2019/072406, which is incorporated herein by reference in its entirety.

In some embodiments, the genetically-modified non-human animal does not express B2M (e.g., intact or functional B2M protein). Because B2M is a subunit of MHC I, the genetically-modified non-human animal does not have functional MHC I class molecules, and/or cannot present peptides to T cells (e.g., CD8+ cells).

In some embodiments, the genetically-modified non-human animal does not express MHC class I molecules, or expresses dysfunctional MHC class I molecules.

The present disclosure further relates to a non-human mammal generated through the methods as described herein. In some embodiments, the genome thereof contains human gene(s).

In addition, the present disclosure also relates to a tumor bearing non-human mammal model, characterized in that the non-human mammal model is obtained through the methods as described herein. In some embodiments, the non-human mammal is a rodent (e.g., a mouse).

The present disclosure further relates to a cell or cell line, or a primary cell culture thereof derived from the non-human mammal or an offspring thereof, or the tumor bearing non-human mammal; the tissue, organ or a culture thereof derived from the non-human mammal or an offspring thereof, or the tumor bearing non-human mammal; and the tumor tissue derived from the non-human mammal or an offspring thereof when it bears a tumor, or the tumor bearing non-human mammal.

The present disclosure also provides non-human mammals produced by any of the methods described herein. In some embodiments, a non-human mammal is provided; and the genetically modified animal contains a modification (e.g., replacement and/or disruption) of the B2M and/or FcRn gene in the genome of the animal.

Genetic, molecular and behavioral analyses for the non-human mammals described above can be performed. The present disclosure also relates to the progeny produced by the non-human mammal provided by the present disclosure mated with the same or other genotypes.

The present disclosure also provides a cell line or primary cell culture derived from the non-human mammal or a progeny thereof. A model based on cell culture can be prepared, for example, by the following methods. Cell cultures can be obtained by way of isolation from a non-human mammal, alternatively cell can be obtained from the cell culture established using the same constructs and the cell transfection techniques. The modification of B2M and/or FcRn gene can be detected by a variety of methods.

There are also many analytical methods that can be used to detect DNA expression, including methods at the level of RNA (including the mRNA quantification approaches using reverse transcriptase polymerase chain reaction (RT-PCR) or Southern Blotting, and in situ hybridization) and methods at the protein level (including histochemistry, immunoblot analysis and in vitro binding studies). Analysis methods can be used to complete quantitative measurements. For example, transcription levels of wild-type genes and the modified sequences can be measured using RT-PCR and hybridization methods including RNase protection, Southern blot analysis, RNA dot analysis (RNAdot) analysis. Immunohistochemical staining, flow cytometry, Western blot analysis can also be used to assess the presence of human proteins.

In some embodiments, the expression of the fusion protein in a genetically modified animal is controllable, as by the addition of a specific inducer or repressor substance. In some embodiments, the specific inducer is selected from Tet-Off System/Tet-On System, or Tamoxifen System.

Fusion Protein

In one aspect, the disclosure is related to a genetically-modified non-human animal expressing a fusion protein comprising, preferably from N-terminus to C-terminus:

(a) an endogenous B2M polypeptide (with or without a signal peptide);
(b) an optional linker peptide; and
(c) an endogenous FcRn polypeptide (with or without a signal peptide).

In some embodiments, the endogenous B2M polypeptide does not have a signal peptide (e.g., an amino acid sequence that is at least 80%, 85%, 90%, 95%, or 100% identical to, or corresponds to, amino acids 1-20 of SEQ ID NO: 2). In some embodiments, the endogenous B2M polypeptide comprises or consists of an amino acid sequence that is at least 70%, 75%, 80%, 85%, 90%, 95%, 99%, or 100% identical to amino acids 21-119 of SEQ ID NO: 2. In some embodiments, the endogenous B2M polypeptide comprises or consists of the mature protein (not including the signal peptide) of endogenous B2M protein.

In some embodiments, the endogenous FcRn polypeptide does not have a signal peptide (e.g., an amino acid sequence that is at least 80%, 85%, 90%, 95%, or 100% identical to, or corresponds to, amino acids 1-21 of SEQ ID NO: 4). In some embodiments, the endogenous FcRn polypeptide comprises or consists of an amino acid sequence that is at least 70%, 75%, 80%, 85%, 90%, 95%, 99%, or 100% identical to amino acids 22-365 of SEQ ID NO: 4. In some embodiments, the endogenous FcRn polypeptide comprises or consists of the extracellular region (not including the signal peptide), the transmembrane region, and the cytoplasmic region of endogenous FcRn protein.

In some embodiments, the endogenous B2M polypeptide is encoded by a nucleotide sequence. In some embodiments, the nucleotide sequence includes a sequence that is at least 70%, 75%, 80%, 85%, 90%, 95%, 99%, or 100% identical to SEQ ID NO: 9. In some embodiments, at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% of the nucleotide sequence is identical to or derived from mouse B2M mRNA sequence (e.g., NM_009735.3 (SEQ ID NO: 1)), or a portion thereof (e.g., a portion of exon 1, exon 2, and exon 3). In some embodiments, the nucleotide sequence is a cDNA sequence. In some embodiments, the nucleotide sequence does not include introns (e.g., intron 1, intron 2, and/or intron 3 of the endogenous B2M gene). In some embodiments, at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% of the amino acid sequence of endogenous B2M polypeptide is identical or derived from mouse B2M amino acid sequence (e.g., NP_033865.2 (SEQ ID NO: 2)), or a portion thereof (e.g., amino acids 21-119 of SEQ ID NO: 2; or SEQ ID NO: 40). In some embodiments, the endogenous B2M polypeptide is identical or derived from a mature protein of endogenous B2M.

In some embodiments, the endogenous FcRn polypeptide is encoded by a nucleotide sequence. In some embodiments, the nucleotide sequence includes a sequence that is at least 70%, 75%, 80%, 85%, 90%, 95%, 99%, or 100% identical to SEQ ID NO: 43. In some embodiments, at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% of the nucleotide sequence is identical to or derived from mouse FcRn mRNA sequence (e.g., NM_010189.3 (SEQ ID NO: 3)), or a portion thereof (e.g., a portion of exon 2, and exons 3-7). In some embodiments, the nucleotide sequence is a genomic DNA sequence. In some embodiments, the nucleotide sequence includes introns (e.g., all or part of intron 1, intron 2, intron 3, intron 4, intron 5, and/or intron 6 of the endogenous FcRn gene). In some embodiments, at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% of the amino acid sequence of endogenous FcRn polypeptide is identical or derived from mouse FcRn amino acid sequence (e.g., NP_034319.2 (SEQ ID NO: 4)), or a portion thereof (e.g., amino acids 22-365 of SEQ ID NO: 4; or SEQ ID NO: 41). In some embodiments, the endogenous FcRn polypeptide is identical or derived from a mature protein of endogenous FcRn.

In some embodiments, the endogenous B2M is fused to the endogenous FcRn with or without a linker peptide. In some embodiments, the linker peptide is optional, i.e., the two regions that are linked together can be directly linked by a peptide bond. In some embodiments, the linker peptide comprises at least or about 5, 6, 7, 8, 9, 10, 11, 12, 13, 14, 15, 16, 17, 18, 19, 20, 30, 40, or 50 amino acid residues. In some embodiments, the linker peptide comprises at least or about 4, 5, 6, 7, 8, 9, 10, 11, 12, 13, 14, 15, 16, 20, 25, 30, or 40 glycine residues. In some embodiments, the linker peptide comprises at least or about 1, 2, 3, 4, 5, 6, 7, or 8 serine residues. In some embodiments, the linker peptide comprises or consists of both glycine and serine residues. In some embodiments, the linker peptide comprises or consists of a sequence that is at least or about 70%, at least or about 75%, at least or about 80%, at least or about 85%, at least or about 90%, at least or about 95%, at least or about 99%, or 100% identical to SEQ ID NO: 46. In some embodiments, the linker peptide comprises at least 1, 2, 3, 4, 5, 6, 7, or 8 repeats of GGGGS (SEQ ID NO: 47). In some embodiments, the linker peptide has no more than 10, 11, 12, 13, 14, 15, 16, 17, 18, 19, 20, 30, 40, or 50 amino acid residues. In some embodiments, the linker peptide is encoded by a sequence that is at least 70%, 75%, 80%, 85%, 90%, 95%, 99%, or 100% identical to SEQ ID NO: 10.

In some embodiments, the fusion protein further includes a signal peptide of endogenous FcRn, e.g., at the N-terminus of the fusion protein. In some embodiments, the signal peptide of endogenous FcRn comprises or consists of an amino acid sequence that is at least 70%, 75%, 80%, 85%, 90%, 95%, 99%, or 100% identical to amino acids 1-21 of SEQ ID NO: 4 or SEQ ID NO: 42. In some embodiments, the signal peptide is encoded by a nucleotide sequence. In some embodiments, the nucleotide sequence includes a sequence that is at least 70%, 75%, 80%, 85%, 90%, 95%, 99%, or 100% identical to SEQ ID NO: 44.

In some embodiments, the fusion protein described herein is encoded by a nucleotide sequence. In some embodiments, the nucleotide sequence includes a sequence that is at least 70%, 75%, 80%, 85%, 90%, 95%, 99%, or 100% identical to SEQ ID NO: 5 or 45. In some embodiments, the fusion protein described herein comprises an amino acid sequence. In some embodiments, the amino acid sequence includes a sequence that is at least 70%, 75%, 80%, 85%, 90%, 95%, 99%, or 100% identical to SEQ ID NO: 6.

In some embodiments, the fusion protein described herein is encoded by a nucleotide sequence. In some embodiments, the nucleotide sequence which further comprises a 5' UTR of the endogenous FcRn mRNA sequence (e.g., 5'UTR of mouse FcRn mRNA sequence NM_010189.3 (SEQ ID NO: 3)), preferably at the 5' end of the nucleotide sequence. In some embodiments, the nucleotide sequence which further comprises a 3' UTR of the endogenous FcRn mRNA sequence (e.g., 3'UTR of mouse FcRn mRNA sequence NM_010189.3 (SEQ ID NO: 3)), preferably at the 3' end of the nucleotide sequence.

In some embodiments, the genome of the animal comprises at least one chromosome comprising a sequence encoding the fusion protein. In some embodiments, the sequence encoding the fusion protein is operably linked to a promotor or regulatory element, e.g., an endogenous B2M (e.g., mouse B2M) promotor, an inducible promoter, an enhancer, and/or mouse or human regulatory elements. In some embodiments, the sequence encoding the fusion protein is operably linked to a promotor or regulatory element, e.g., an endogenous mouse FcRn promotor, an inducible promoter, an enhancer, and/or mouse or human regulatory elements.

In some embodiments, all or a part of endogenous B2M gene is knocked out. In some embodiments, all or a part of endogenous FcRn gene (e.g., mouse FcRn gene) is knocked out.

In some embodiments, a recombinant sequence encoding the fusion protein described herein is inserted within the endogenous B2M or FcRn gene locus. In some embodiments, the endogenous B2M or FcRn gene coding region are not transcribed or translated, due to the presence of a stop codon and the polyA signal after the inserted recombinant sequence.

In some embodiments, both the endogenous B2M gene and endogenous FcRn gene are knocked out in an animal, and a recombinant sequence encoding the fusion protein described herein is inserted to the genome of the animal.

In some embodiments, the nucleotide sequence encoding the fusion protein described herein has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that are different from part of or the entire mouse B2M nucleotide sequence (e.g., exon 1, exon 2, exon 3, exon 4, or NM_009735.3 (SEQ ID NO: 1)).

In some embodiments, the nucleotide sequence encoding the fusion protein described herein has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is the same as part of or the entire mouse B2M nucleotide sequence (e.g., exon 1, exon 2, exon 3, exon 4, or NM_009735.3 (SEQ ID NO: 1)).

In some embodiments, the nucleotide sequence encoding the fusion protein described herein has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that are different from part of or the entire mouse FcRn nucleotide sequence (e.g., exon 1, exon 2, exon 3, exon 4, exon 5, exon 6, exon 7, or NM_010189.3 (SEQ ID NO: 3)).

In some embodiments, the nucleotide sequence encoding the fusion protein described herein has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is different from part of or the entire mouse FcRn amino acid sequence (e.g., amino acids encoded by exon 1, exon 2, exon 3, exon 4, exon 5, exon 6, and/or exon 7, of NM_010189.3 (SEQ ID NO: 3); or NP_034319.2 (SEQ ID NO: 4)).

In some embodiments, the amino acid sequence of the fusion protein described herein has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is different from part of or the entire mouse B2M amino acid sequence (e.g., amino acids encoded by exon 1, exon 2, exon 3, and/or exon 4 of NM_009735.3 (SEQ ID NO: 1); or NP_033865.2 (SEQ ID NO: 2)).

In some embodiments, the amino acid sequence of the fusion protein described herein has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is the same as part of or the entire mouse B2M amino acid sequence (e.g., amino acids encoded by exon 1, exon 2, exon 3, and/or exon 4 of NM_009735.3 (SEQ ID NO: 1); or NP_033865.2 (SEQ ID NO: 2)).

In some embodiments, the amino acid sequence of the fusion protein described herein has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is different from part of or the entire mouse FcRn amino acid sequence (e.g., amino acids encoded by exon 1, exon 2, exon 3, exon 4, exon 5, exon 6, and/or exon 7, of NM_010189.3 (SEQ ID NO: 3); or NP_034319.2 (SEQ ID NO: 4)).

In some embodiments, the amino acid sequence of the fusion protein described herein has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is the same as part of or the entire mouse FcRn amino acid sequence (e.g., amino acids encoded by exon 1, exon 2, exon 3, exon 4, exon 5, exon 6, and/or exon 7 of NM_010189.3 (SEQ ID NO: 3); or NP_034319.2 (SEQ ID NO: 4)).

In some embodiments, the fusion protein described herein comprises or consists of an amino acid sequence, wherein the amino acid sequence is selected from the group consisting of:

a) an amino acid sequence shown in SEQ ID NO: 2, 4, 6, 40, 41, 42, or 46;
b) an amino acid sequence having a homology of at least 90% with or at least 90% identical to the amino acid sequence shown in SEQ ID NO: 2, 4, 6, 40, 41, 42, or 46;
c) an amino acid sequence encoded by a nucleic acid sequence, wherein the nucleic acid sequence is able to hybridize to a nucleotide sequence encoding the amino acid shown in SEQ ID NO: 2, 4, 6, 40, 41, 42, or 46 under a low stringency condition or a strict stringency condition;
d) an amino acid sequence having a homology of at least 90%, 91%, 92%, 93%, 94%, 95%, 96%, 97%, 98%, or 99%, or at least 90%, 91%, 92%, 93%, 94%, 95%, 96%, 97%, 98%, or 99% identical to the amino acid sequence shown in SEQ ID NO: 2, 4, 6, 40, 41, 42, or 46;
e) an amino acid sequence that is different from the amino acid sequence shown in SEQ ID NO: 2, 4, 6, 40, 41, 42, or 46 by no more than 10, 9, 8, 7, 6, 5, 4, 3, 2 or no more than 1 amino acid; or
f) an amino acid sequence that comprises a substitution, a deletion and/or insertion of one or more amino acids to the amino acid sequence shown in SEQ ID NO: 2, 4, 6, 40, 41, 42, or 46.

The present disclosure also relates to a nucleic acid (e.g., DNA or RNA) sequence encoding all or part of the fusion protein described herein, wherein the nucleic acid sequence can be selected from the group consisting of:

a) a nucleic acid sequence as shown in SEQ ID NO: 1, 3, 5, 7, 8, 9, 43, 44, or 45, or a nucleic acid sequence encoding a homologous B2M or FcRn amino acid sequence of an endogenous mouse B2M or FcRn;
b) a nucleic acid sequence that is able to hybridize to the nucleotide sequence as shown in SEQ ID NO: 1, 3, 5, 7, 8, 9, 43, 44, or 45 under a low stringency condition or a strict stringency condition;
c) a nucleic acid sequence that has a homology of at least 90%, 91%, 92%, 93%, 94%, 95%, 96%, 97%, 98%, or 99%, or at least 90%, 91%, 92%, 93%, 94%, 95%, 96%, 97%, 98%, or 99% identical to the nucleotide sequence as shown in SEQ ID NO: 1, 3, 5, 7, 8, 9, 43, 44, or 45;
d) a nucleic acid sequence that encodes an amino acid sequence, wherein the amino acid sequence has a homology of at least 90% with or at least 90% identical to the amino acid sequence shown in SEQ ID NO: 2, 4, 6, 40, 41, 42, or 46;
e) a nucleic acid sequence that encodes an amino acid sequence, wherein the amino acid sequence has a homology of at least 90%, 91%, 92%, 93%, 94%, 95%, 96%, 97%, 98%, or 99% with, or at least 90%, 91%, 92%, 93%, 94%, 95%, 96%, 97%, 98%, or 99% identical to the amino acid sequence shown in SEQ ID NO: 2, 4, 6, 40, 41, 42, or 46;
f) a nucleic acid sequence that encodes an amino acid sequence, wherein the amino acid sequence is different from the amino acid sequence shown in SEQ ID NO: 2, 4, 6, 40, 41, 42, or 46 by no more than 10, 9, 8, 7, 6, 5, 4, 3, 2 or no more than 1 amino acid; and/or
g) a nucleic acid sequence that encodes an amino acid sequence, wherein the amino acid sequence comprises a substitution, a deletion and/or insertion of one or more amino acids to the amino acid sequence shown in SEQ ID NO: 2, 4, 6, 40, 41, 42, or 46.

In some embodiments, the genetically-modified non-human animal expressing the fusion protein described herein expresses a normal level of endogenous B2M (e.g., mouse B2M). In some embodiments, the genetically-modified non-human animal expressing a the fusion protein described herein expressed a decreased level (e.g., less than 90%, less than 80%, less than 70%, less than 60%, or less than 50% as compared to that of an animal without the genetic modification) of endogenous B2M (e.g., mouse B2M). In some embodiments, the genetically-modified non-human animal expressing the fusion protein described herein does not express endogenous B2M (e.g., mouse B2M).

Vectors

The disclosure also provides vectors for constructing an animal model expressing the B2M/FcRn fusion protein described herein. In some embodiments, the vectors comprise a sgRNA sequence. In some embodiments, the sgRNA sequence targets FcRn gene (e.g., of the non-human animal described herein), and the sgRNA is unique on the target sequence of the FcRn gene to be altered, and meets the sequence arrangement rule of 5'-NNN (20)-NGG3' or 5'-CCN—N(20)-3'. In some embodiments, the targeting site of the sgRNA in the mouse FcRn gene is located on exon 1, exon 2, exon 3, exon 4, exon 5, exon 6, exon 7, intron 1, intron 2, intron 3, intron 4, intron 5, intron 6, upstream of exon 1, or downstream of exon 7 of the mouse FcRn gene. In some embodiments, the targeting site of the sgRNA in the mouse B2M gene is located on exon 2 or intron 2.

In some embodiments, the sgRNA sequence recognizes a targeting site within exon 2 or intron 2 of mouse FcRn gene. In some embodiments, the targeting sites within exon 2 or intron 2 are set forth in SEQ ID NOS: 11-18. In some embodiments, the targeting site within exon 2 or intron 2 is set forth in SEQ ID NO: 16. In some embodiments, the sgRNA sequences are encoded by double-strand DNA molecules with sequences set forth in SEQ ID NO: 20 and SEQ ID NO: 22; or SEQ ID NO: 21 and SEQ ID NO: 23.

In some embodiments, the disclosure relates to a plasmid construct (e.g., pT7-sgRNA) including the sgRNA sequence, and/or a cell including the construct.

In some embodiments, the disclosure relates to a targeting vector including a 5' homologous arm and a 3' homologous arm. In some embodiments, the 5' homologous arm comprises a sequence spanning the entire or part of upstream of exon 1, exon 1, intron 1, and exon 2 of mouse FcRn gene. In some embodiments, the 3' homologous arm comprises a sequence spanning the entire or part of exon 2, intron 2, exon 3, intron 3, exon 4, and intron 4.

In some embodiments, the 5' homologous arm comprises a sequence that is at least 80%, 85%, 90%, 95%, or 100% identical to SEQ ID NO: 7. In some embodiments, the 3' homologous arm comprises a sequence that is at least 80%, 85%, 90%, 95%, or 100% identical to SEQ ID NO: 8. In some embodiments, the 5' homologous arm comprises a sequence that is at least 80%, 85%, 90%, 95%, 99%, or 100% identical to 45103007-45104486 of the NCBI Reference Sequence NC_000073.6. In some embodiments, the 5' homologous arm comprises a C to G mutation at position 45103046, and a C to A mutation at position 45103052 of NCBI Reference Sequence NC_000073.6. In some embodiments, the 3' homologous arm comprises a sequence that is at least 80%, 85%, 90%, 95%, 99%, or 100% identical to 45101562-45103006 of the NCBI Reference Sequence NC_000073.6.

In some embodiments, the targeting vector further comprises a nucleotide sequence between the 5' and 3' homologous arms. In some embodiments, the nucleotide sequence comprises a sequence (e.g., a cDNA sequence) encoding the entire or a part of the endogenous B2M polypeptide and the linker peptide described herein. In some embodiments, the nucleotide sequence comprises or consists, preferably from 5' end to 3' end: a sequence encoding the endogenous B2M polypeptide described herein, and a sequence encoding the linker peptide described herein.

In addition, the present disclosure further relates to a non-human mammalian cell, having any one of the foregoing targeting vectors, and one or more in vitro transcripts of the sgRNA construct as described herein. In some embodiments, the cell includes Cas9 mRNA or an in vitro transcript thereof.

In some embodiments, the genes in the cell are heterozygous. In some embodiments, the genes in the cell are homozygous.

In some embodiments, the non-human mammalian cell is a mouse cell. In some embodiments, the cell is a fertilized egg cell.

In some embodiments, provided herein is a method for preparing a vector comprising an sgRNA sequence, the method includes the following steps: (a) providing the sgRNA sequence, which is obtained using a forward oligonucleotide sequence and a reverse oligonucleotide sequence, wherein the sgRNA sequence targets the non-human animal FcRn gene described herein, wherein the sgRNA is unique on the target FcRn gene to be altered, and meets the sequence arrangement rule of 5'-NNN(20)-NGG3' or 5'-CCN—N(20)-3'; (b) synthesizing a DNA fragment containing the T7 promoter and an sgRNA scaffold (e.g., at least 80% identical to SEQ ID NO: 24), then ligating the DNA fragment to the backbone vector after EcoRI and BamHI digestion, and obtaining a pT7-sgRNA vector after verification by sequencing; (c) denaturing and annealing the forward oligonucleotide and the reverse oligonucleotide obtained in step (a) to form a double strand that can be ligated to the pT7-sgRNA vector described in step (b); (d) ligating the double-stranded sgRNA oligonucleotides annealed in step (c) with the pT7-sgRNA vector, and screening to obtain the sgRNA vector.

Methods of Making Genetically Modified Animals

Genetically modified animals can be made by several techniques that are known in the art, including, e.g., non-homologous end-joining (NHEJ), homologous recombination (HR), zinc finger nucleases (ZFNs), transcription activator-like effector-based nucleases (TALEN), and the clustered regularly interspaced short palindromic repeats (CRISPR)-Cas system. In some embodiments, homologous recombination is used. In some embodiments, CRISPR-Cas9 genome editing is used to generate genetically modified animals. Many of these genome editing techniques are known in the art, and is described, e.g., in Yin et al., "Delivery technologies for genome editing," Nature Reviews Drug Discovery 16.6 (2017): 387-399, which is incorporated by reference in its entirety. Many other methods are also provided and can be used in genome editing, e.g., micro-injecting a genetically modified nucleus into an enucleated oocyte, and fusing an enucleated oocyte with another genetically modified cell.

Thus, in some embodiments, the disclosure provides inserting in at least one cell of the animal a sequence encoding a region of an endogenous B2M gene sequence, at an endogenous FcRn gene locus. In some embodiments, the insertion occurs in a germ cell, a somatic cell, a blastocyst, or a fibroblast, etc. The nucleus of a somatic cell or the fibroblast can be inserted into an enucleated oocyte.

Figure 3:
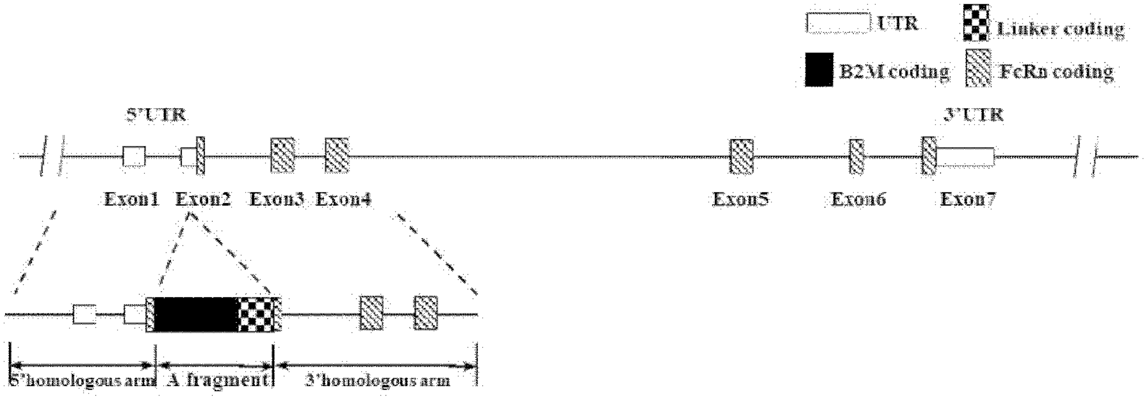
FIG. 3 shows a schematic diagram of FcRn locus targeting strategy and targeting vector design.

FIG. 3 shows a targeting strategy for at mouse FcRn gene locus. In FIG. 3, the targeting strategy involves a vector comprising the 5' homologous arm, a sequence encoding an endogenous B2M polypeptide and a linker peptide, and the 3' homologous arm. The process can involve inserting an endogenous B2M gene sequence at an endogenous FcRn gene locus by homologous recombination, thereby generating a B2M/FcRn fusion gene. In some embodiments, the cleavage at the targeting site (e.g., by zinc finger nucleases, TALEN or CRISPR) can result in DNA double strands break, and the homologous recombination is used to insert an endogenous B2M gene sequence at the DNA break site.

Thus, in some embodiments, the methods for making a genetically modified animal, can include the step of inserting at an endogenous FcRn locus (or site), a nucleic acid encoding a sequence encoding a region of endogenous B2M, thereby generating a B2M/FcRn fusion gene. In some embodiments, the animal expresses a fusion protein encoded by the B2M/FcRn fusion gene sequence. In some embodiments, the B2M/FcRn fusion gene includes a region (e.g., a part or the entire region) of exon 1, exon 2, exon 3, exon 4 of an endogenous B2M gene, and one or more regions (e.g., a part or the entire region) of exon 1, exon 2, exon 3, exon 4, exon 5, exon 6, and/or exon 7, of an endogenous FcRn gene. In some embodiments, the endogenous B2M gene is a portion of exon 1, exon 2, and exon 3 of mouse B2M gene (e.g., a sequence encoding amino acids 21-119 of SEQ ID NO: 2). In some embodiments, the B2M/FcRn fusion gene includes a first endogenous FcRn gene fragment including a portion of exon 2 of mouse FcRn gene (a sequence encoding amino acids 1-21 of SEQ ID NO: 4); and a second endogenous FcRn gene fragment including a portion of exon 2 and exons 3-7 of SEQ ID NO: 4 (a sequence encoding amino acids 22-365 of SEQ ID NO: 4). In some embodiments, the sequence encoding a region of endogenous B2M is inserted between the first and the second endogenous FcRn gene fragments.

In some embodiments, the methods of modifying a FcRn gene locus of a mouse to express the fusion protein described herein can include the steps of inserting at the endogenous mouse FcRn gene locus a nucleotide sequence encoding a mouse B2M, thereby generating a sequence encoding a fusion protein comprising an endogenous B2M (e.g., amino acids 21-119 of SEQ ID NO: 2) and an endogenous FcRn (e.g., amino acids 22-365 of SEQ ID NO: 4).

In some embodiments, the nucleotide sequences as described herein do not overlap with each other (e.g., the 5' homologous arm, the A fragment, and/or the 3' homologous arm do not overlap). In some embodiments, the amino acid sequences as described herein do not overlap with each other.

Zinc finger proteins, TAL-effector domains, or single guide RNA (sgRNA) DNA-binding domains can be designed to target regions within exon 1, exon 2, exon 3, exon 4, exon 5, exon 6, exon 7, intron 1, intron 2, intron 3, intron 4, intron 5, and/or intron 6 of endogenous (e.g., mouse) FcRn gene locus. For example, targeting sequences of SEQ ID NOs: 11-18 are located in exon 2 or intron 2 of the endogenous (e.g., mouse) FcRn gene locus. After the zinc finger proteins, TAL-effector domains, or single guide RNA (sgRNA) DNA-binding domains bind to the target sequences, the nuclease cleaves the genomic DNA. In some embodiments, the nuclease is CRISPR associated protein 9 (Cas9).

Thus, the methods of producing a mouse expressing a B2M/FcRn fusion protein can involve one or more of the following steps: transforming a mouse embryonic stem cell with a gene editing system that targets endogenous FcRn gene, thereby producing a transformed embryonic stem cell; introducing the transformed embryonic stem cell into a mouse blastocyst; implanting the mouse blastocyst into a pseudopregnant female mouse; and allowing the blastocyst to undergo fetal development to term.

In some embodiments, the transformed embryonic cell is directly implanted into a pseudopregnant female mouse instead, and the embryonic cell undergoes fetal development.

In some embodiments, the gene editing system can involve Zinc finger proteins, TAL-effector domains, or single guide RNA (sgRNA) DNA-binding domains.

The present disclosure further provides a method for establishing an animal model expressing a B2M/FcRn fusion protein, involving the following steps:

(a) providing the cell (e.g. a fertilized egg cell) with the genetic modification based on the methods described herein;
(b) culturing the cell in a liquid culture medium;
(c) transplanting the cultured cell to the fallopian tube or uterus of the recipient female non-human mammal, allowing the cell to develop in the uterus of the female non-human mammal;
(d) identifying the germline transmission in the offspring genetically modified humanized non-human mammal of the pregnant female in step (c).

In some embodiments, an embryonic stem cell is modified. The modified embryonic stem cell is then transferred to a blastocyst, and is then transferred to the uterus of the female non-human mammal.

In some embodiments, the non-human mammal in the foregoing method is a mouse (e.g., a C57BL/6 mouse, a NOD/scid mouse, a NOD/scid nude mouse, a B-NDG mouse, or a BNDG-B2M-KO mouse). In some embodiments, the non-human mammal is a B-NDG (NOD-Prkdc$^{scid}$ IL-2rγ$^{null}$) mouse. In some embodiments, the non-human mammal is a NOD/scid mouse. In some embodiments, the non-human mammal is a BNDG-B2M-KO mouse.

In the B-NDG mouse, the Prkdc$^{scid}$ (commonly known as "SCID" or "severe combined immunodeficiency") mutation has been transferred onto a non-obese diabetic (NOD) background. Animals homozygous for the SCID mutation have impaired T and B cell lymphocyte development. The NOD background additionally results in deficient natural killer (NK) cell function. IL-2rγ$^{null}$ refers to a specific knock out modification in mouse CD132 gene. Details can be found, e.g., in PCT/CN2018/079365, which is incorporated herein by reference in its entirety. In some embodiments, the non-human mammal is a B-NDG mouse. The B-NDG mouse additionally has a disruption of FOXN1 gene on chromosome 11 in mice.

In some embodiments, the fertilized eggs for the methods described above are NOD/scid fertilized eggs, NOD/scid nude fertilized eggs, B-NDG fertilized eggs, BNDG-B2M-KO fertilized eggs. Other fertilized eggs that can also be used in the methods as described herein include, but are not limited to, C57BL/6 fertilized eggs, FVB/N fertilized eggs, BALB/c fertilized eggs, DBA/1 fertilized eggs and DBA/2 fertilized eggs.

Fertilized eggs can come from any non-human animal, e.g., any non-human animal as described herein. In some embodiments, the fertilized egg cells are derived from rodents. The genetic construct can be introduced into a fertilized egg by microinjection of DNA. For example, by way of culturing a fertilized egg after microinjection, a cultured fertilized egg can be transferred to a false pregnant non-human animal, which then gives birth of a non-human mammal, so as to generate the non-human mammal mentioned in the method described above.

Methods of Using Genetically Modified Animals

Genetically modified animals that express a B2M/FcRn fusion protein can provide a variety of uses that include, but are not limited to, establishing a human hemato-lymphoid animal model, developing therapeutics for human diseases and disorders, and assessing the efficacy of these therapeutics in the animal models.

In some embodiments, the genetically modified animals can be used for establishing a human hemato-lymphoid system. The methods involve engrafting a population of cells comprising human hematopoietic cells (CD34+ cells) or human peripheral blood cells into the genetically modified animal described herein. In some embodiments, the methods further include the step of irradiating the animal prior to the engrafting. In some embodiments, the step of irradiating is not required prior to the engrafting. The human hemato-lymphoid system in the genetically modified animals can include various human cells, e.g., hematopoietic stem cells, myeloid precursor cells, myeloid cells, dendritic cells, monocytes, granulocytes, neutrophils, mast cells, lymphocytes, and platelets.

The genetically modified animals described herein (e.g., expressing the B2M/FcRn fusion protein) are also an excellent animal model for establishing the human hemato-lymphoid system. In some embodiments, the animal after being engrafted with human hematopoietic stem cells or human peripheral blood cells to develop a human immune system has one or more of the following characteristics:

(a) the percentage of human leukocytes (or CD45+ cells) is at least or about 10%, 15%, 20%, 25%, 30%, 35%, 40%, 45%, 50%, 55%, or 60% of the total live cells from blood (after lysis of red blood cells) in the animal; and (b) the percentage of human T cells (or CD45+CD3+ cells) is at least or about 50%, 55%, 60%, 65%, 70%, 75%, 80%, 85%, 90%, or 95% of human leukocytes (or CD45+ cells) in the animal.

In some embodiments, the one or more characteristics are determined at least or about 2 weeks, at least or about 3 weeks, at least or about 4 weeks, at least or about 5 weeks, at least or about 6 weeks, at least or about 7 weeks, at least or about 8 weeks, at least or about 9 weeks, at least or about 10 weeks, at least or about 11 weeks, at least or about 12 weeks, or at least or about 13 weeks, after the animal (mouse) is engrafted with human hematopoietic stem cells to develop a human immune system.

In some embodiments, the animal has an enhanced engraftment capacity of exogenous cells relative to a NSG mouse, a NOG mouse, a NOD/scid mouse, or a B-NDG mouse. In some embodiments, the animal models described here are better animal models for establishing the human hemato-lymphoid system (e.g. having a higher survival rate). A detailed description of the NSG mice, NOD mice, and B-NDG can be found, e.g., in Ishikawa et al. "Development of functional human blood and immune systems in NOD/SCID/IL2 receptor γ chainnull mice." Blood 106.5 (2005): 1565-1573; Katano et al. "NOD-Rag2null IL-2Rγnull mice: an alternative to NOG mice for generation of humanized mice." Experimental animals 63.3 (2014): 321-330; US20190320631A1; each of which is incorporated herein by reference in the entirety.

In some embodiments, the genetically modified animals can be used to determine the effectiveness of an agent or a combination of agents for the treatment of cancer. The methods involve engrafting tumor cells to the animal as described herein, administering the agent or the combination of agents to the animal; and determining the inhibitory effects on the tumors.

In some embodiments, the tumor cells are from a tumor sample obtained from a human patient. These animal models are also known as Patient derived xenografts (PDX) models. PDX models are often used to create an environment that resembles the natural growth of cancer, for the study of cancer progression and treatment. Within PDX models, patient tumor samples grow in physiologically-relevant tumor microenvironments that mimic the oxygen, nutrient, and hormone levels that are found in the patient's primary tumor site. Furthermore, implanted tumor tissue maintains the genetic and epigenetic abnormalities found in the patient and the xenograft tissue can be excised from the patient to include the surrounding human stroma. As a result, PDX models can often exhibit similar responses to anti-cancer agents as seen in the actual patient who provide the tumor sample.

While the genetically modified immunodeficient animals (e.g., mice with B-NDG background) do not have functional T cells or B cells, the animals still have functional phagocytic cells, e.g., neutrophils, eosinophils (*acidophilus*), basophils, or monocytes. Macrophages can be derived from monocytes, and can engulf and digest cellular debris, foreign substances, microbes, cancer cells. Thus, the genetically modified animals described herein can be used to determine the effect of an agent (e.g., anti-CD47 antibodies, anti-IL6 antibodies, anti-IL15 antibodies, or anti-SIRPα antibodies) on phagocytosis, and the effects of the agent to inhibit the growth of tumor cells.

In some embodiments, human peripheral blood cells (hPBMC) or human hematopoietic stem cells are injected to the animal to develop human hematopoietic system. The genetically modified animals described herein can be used to determine the effect of an agent in human hematopoietic system, and the effects of the agent to inhibit tumor cell growth or tumor growth. Thus, in some embodiments, the methods as described herein are also designed to determine the effects of the agent on human immune cells (e.g., human T cells, B cells, or NK cells), e.g., whether the agent can stimulate T cells or inhibit T cells, whether the agent can upregulate the immune response or downregulate immune response. In some embodiments, the genetically modified animals can be used for determining the effective dosage of a therapeutic agent for treating a disease in the subject, e.g., cancer, or autoimmune diseases.

In some embodiments, the antibody is designed for treating various immune disorder or immune-related diseases (e.g., psoriasis, allergic rhinitis, sinusitis, asthma, rheumatoid arthritis, atopic dermatitis, chronic obstructive pulmonary disease (COPD), chronic bronchitis, emphysema, eczema, osteoarthritis, rheumatoid arthritis, systemic lupus erythematosus, polymyalgia rheumatica, autoimmune hemolytic anemia, systemic vasculitis, pernicious anemia, inflammatory bowel disease, ulcerative colitis, Crohn's disease, or multiple sclerosis). Thus, the methods as described herein can be used to determine the effectiveness of an antibody in inhibiting immune response.

In some embodiments, the immune disorder or immune-related diseases described here include allergy, asthma, myocarditis, nephritis, hepatitis, systemic lupus erythematosus, rheumatoid arthritis, scleroderma, hyperthyroidism, primary thrombocytopenic purpura, autoimmune hemolytic anemia, ulcerative colitis, self-immune liver disease, diabetes, pain, or neurological disorders.

In some embodiments, the tested agent or the combination of tested agents is designed for treating various cancers. As used herein, the term "cancer" refers to cells having the capacity for autonomous growth, i.e., an abnormal state or condition characterized by rapidly proliferating cell growth. The term is meant to include all types of cancerous growths or oncogenic processes, metastatic tissues or malignantly transformed cells, tissues, or organs, irrespective of histopathologic type or stage of invasiveness. The term "tumor" as used herein refers to cancerous cells, e.g., a mass of cancerous cells. Cancers that can be treated or diagnosed using the methods described herein include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus. In some embodiments, the agents described herein are designed for treating or diagnosing a carcinoma in a subject. The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. In some embodiments, the cancer is renal carcinoma or melanoma. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation.

In some embodiments, the cancer types as described herein include, but not limited to, lymphoma, non-small cell lung cancer (NSCLC), leukemia, ovarian cancer, nasopharyngeal cancer, breast cancer, endometrial cancer, colon cancer, rectal cancer, stomach cancer, bladder cancer, lung cancer, bronchial cancer, bone cancer, prostate cancer, pancreatic cancer, liver and bile duct cancer, esophageal cancer, kidney cancer, thyroid cancer, head and neck cancer, testicular cancer, glioblastoma, astrocytoma, melanoma, myelodysplastic syndrome, and sarcoma. In some embodiments, the leukemia is selected from acute lymphocytic (lymphoblastic) leukemia, acute myeloid leukemia, myeloid leukemia, chronic lymphocytic leukemia, multiple myeloma, plasma cell leukemia, and chronic myelogenous leukemia. In some embodiments, the lymphoma is selected from Hodgkin's lymphoma and non-Hodgkin's lymphoma, including B-cell lymphoma, diffuse large B-cell lymphoma, follicular lymphoma, mantle cell lymphoma, marginal zone B-cell lymphoma, T cell lymphoma, and Waldenstrom macroglobulinemia. In some embodiments, the sarcoma is selected from osteosarcoma, Ewing sarcoma, leiomyosarcoma, synovial sarcoma, soft tissue sarcoma, angiosarcoma, liposarcoma, fibrosarcoma, rhabdomyosarcoma, and chondrosarcoma. In some embodiments, the cancer is Cervical cancer, esophageal cancer, kidney cancer, brain cancer, breast cancer, ovarian cancer, prostate cancer, or gastric cancer.

In some embodiments, the tested agent is designed for the treating colon cancer, lung cancer (e.g., lung squamous cell carcinoma), melanoma, primary lung carcinoma, non-small cell lung carcinoma (NSCLC), small cell lung cancer (SCLC), primary gastric carcinoma, bladder cancer, breast cancer, and/or prostate cancer.

In some embodiments, the injected tumor cells are human tumor cells. In some embodiments, the injected tumor cells are colon cancer cells, lung cancer cells, melanoma cells, primary lung carcinoma cells, non-small cell lung carcinoma (NSCLC) cells, small cell lung cancer (SCLC) cells, primary gastric carcinoma cells, bladder cancer cells, breast cancer cells, and/or prostate cancer cells.

The inhibitory effects on tumors can also be determined by any methods known in the art. In some embodiments, the tumor cells can be labeled by a luciferase gene. Thus, the number of the tumor cells or the size of the tumor in the animal can be determined by an in vivo imaging system (e.g., the intensity of fluorescence). In some embodiments, the inhibitory effects on tumors can also be determined by measuring the tumor volume in the animal, and/or determining tumor (volume) inhibition rate ($TGI_{TV}$). The tumor growth inhibition rate can be calculated using the formula $TGI_{TV}$ (%)=(1−TVt/TVc)×100, where TVt and TVc are the mean tumor volume (or weight) of treated and control groups.

In some embodiments, the tested agent can be one or more agents selected from the group consisting of paclitaxel, cisplatin, carboplatin, pemetrexed, 5-FU, gemcitabine, oxaliplatin, docetaxel, and capecitabine.

In some embodiments, the tested agent can be an antibody, for example, an antibody that binds to CSF2, IL3, CSF1, IL15, PD-1, CTLA-4, LAG-3, TIM-3, BTLA, PD-L1, 4-1BB, CD27, CD28, CD47, TWO, TIGIT, CD27, GITR, SIRPα, or OX40. In some embodiments, the antibody is a human antibody.

The present disclosure also relates to the use of the animal model generated through the methods as described herein in the development of a product related to an immunization processes of human cells, the manufacturing of a human antibody, or the model system for a research in pharmacology, immunology, microbiology and medicine.

In some embodiments, the disclosure provides the use of the animal model generated through the methods as described herein in the production and utilization of an animal experimental disease model of an immunization processes involving human cells, the study on a pathogen, or the development of a new diagnostic strategy and/or a therapeutic strategy.

In some embodiments, the genetically-modified non-human animal expressing a B2M/FcRn fusion protein and having a disruption of endogenous B2M gene described herein is less likely to develop graft-versus-host disease (GVHD) or xenogeneic graft-versus-host disease (X-GVHD).

In some embodiments, the genetically-modified non-human animal expressing a B2M/FcRn fusion protein and having a disruption of endogenous B2M gene described herein can be used to evaluate effectiveness of an IgG or Fc-domain containing fragment thereof for treating a disease (e.g., cancer) in a subject. When administered, the half-life of the IgG or fragment thereof is at least 1 day, at least 2 days, at least 3 days, at least 4 days, at least 5 days, at least 6 days, at least 7 days, at least 8 days, at least 9 days, at least 10 days, at least 11 days, or longer. Because the endogenous B2M polypeptide and the endogenous FcRn polypeptide within the B2M/FcRn fusion protein can interact with each other, forming a functional FcRn protein complex, the half-life of the IgG or Fc-domain containing fragment thereof is at least 1 day, at least 2 days, at least 3 days, at least 4 days, or at least 5 days longer than the IgG half-life in an animal expressing the B2M/FcRn fusion protein, without a disruption of endogenous B2M gene (e.g., an animal having a wild-type B2M gene locus). In some embodiments, PK parameters (e.g., calculated from a Non-Compartmental Analysis model) including drug peak concentration ($C_{max}$); peak time ($T_{max}$); area under the blood drug concentration-time curve from Day 0 to Day 24 ($AUC_{0-24}$); area under the blood drug concentration-time curve from the start of administration (Day 0) to theoretical extrapolation ($AUC_{0-inf}$); apparent volume of distribution ($V_z$); clearance rate (Cl); and steady-state apparent volume of distribution ($V_{ss}$) of the animal is improved by at least 10%, 20%, 30%, 40%, 50%, 60%, 70%, 80%, 90%, or 100%, as compared to those of an IgG administered to an animal expressing the B2M/FcRn fusion protein, without a disruption of endogenous B2M gene (e.g., an animal having a wild-type B2M gene locus).

Thus, in one aspect, the genetic modified animals as described herein are particularly suitable for evaluating the efficacy of cell therapy (e.g., T cell based cell therapy). In some embodiments, the disclosure provides a method to verify in vivo efficacy of TCR-T, CAR-T, and/or other immunotherapies (e.g., T-cell adoptive transfer therapies). For example, the methods include transplanting human tumor cells into the animal described herein, and applying immunotherapies (e.g., human CAR-T therapy) to the animal with human tumor cells. Effectiveness of the CAR-T therapy can be determined and evaluated. In some embodiments, the animal is selected from the non-human animal prepared by the methods described herein, the non-human animal described herein, the double- or multi-humanized non-human animal generated by the methods described herein (or progeny thereof), a non-human animal expressing humanized MHC protein complex, or the tumor-bearing or inflammatory animal models described herein. In some embodiments, the TCR-T, CAR-T, and/or other immunotherapies can treat the diseases described herein. In some embodiments, the TCR-T, CAR-T, and/or other immunotherapies provides an evaluation method for treating the diseases (e.g., cancer) described herein.

Animal Models with Additional Genetic Modifications

The present disclosure further relates to methods for generating genetically modified animal models described herein with some additional modifications (e.g., human or chimeric genes or additional gene knockout).

In some embodiments, the animal can comprise a sequence encoding the fusion protein described herein and a sequence encoding an additional human or chimeric protein. In some embodiments, the additional human or chimeric protein can be Colony Stimulating Factor 2 (CSF2), IL3, Colony Stimulating Factor 1 (CSF1), IL15, programmed cell death protein 1 (PD-1), TNF Receptor Superfamily Member 9 (4-1BB or CD137), cytotoxic T-lymphocyte-associated protein 4 (CTLA-4), LAG-3, T-cell immunoglobulin and mucin-domain containing-3 (TIM-3), B And T Lymphocyte Associated (BTLA), Programmed Cell Death 1 Ligand 1 (PD-L1), CD27, CD28, Signal-regulatory protein alpha (SIRPα), CD47, Thrombopoietin (TWO), T-Cell Immunoreceptor With Ig And ITIM Domains (TIGIT), Glucocorticoid-Induced TNFR-Related Protein (GITR), or TNF Receptor Superfamily Member 4 (TNFRSF4; or OX40).

In some embodiments, the animal can comprise a sequence encoding the B2M/FcRn fusion protein and a disruption at some other endogenous genes (e.g., CD132, Beta-2-Microglobulin (B2m) or Forkhead Box N1 (Foxn1)). In some embodiments, the animal has a mutation in KIT. The genetically modified non-human animals with a mutation in KIT is described, e.g., in PCT/CN2020/113608, which is incorporated herein by reference in its entirety.

The methods of generating genetically modified animal model with a B2M/FcRn fusion gene and one or more human or chimeric genes (e.g., humanized genes) can include the following steps:

(a) using the methods of introducing a sequence encoding the fusion protein as described herein to obtain a genetically modified non-human animal;

(b) mating the genetically modified non-human animal with another genetically modified non-human animal, and then screening the progeny to obtain a genetically modified non-human animal with the B2M/FcRn fusion gene and one or more human or chimeric genes.

In some embodiments, in step (b) of the method, the genetically modified animal can be mated with a genetically modified non-human animal with human or chimeric CSF2, IL3, CSF1, IL15, PD-1, CTLA-4, LAG-3, TIM-3, BTLA, PD-L1, 4-1BB, CD27, CD28, SIRPα, CD47, THPO, TIGIT, GITR, or OX40. Some of these genetically modified non-human animals are described, e.g., in PCT/CN2017/090320, PCT/CN2017/099577, PCT/CN2017/099575, PCT/CN2017/099576, PCT/CN2017/099574, PCT/CN2017/106024, PCT/CN2020/125489, PCT/CN2020/142546, CN111172190A, CN111118019A, and CN111073907A; each of which is incorporated herein by reference in its entirety.

In some embodiments, the genetic modification described herein can be directly performed on a genetically modified animal having a human or chimeric CSF2, IL3, CSF1, IL15, PD-1, CTLA-4, LAG-3, BTLA, TIM-3, PD-L1, 4-1BB, CD27, CD28, SIRPα, CD47, THPO, TIGIT, GITR, or OX40 gene.

In some embodiments, the genetic modification described herein can be directly performed on a B2m knockout mouse or a Foxn1 knockout mouse. In some embodiments, the genetic modification described herein can be directly performed on a B-NDG mouse.

As these proteins may involve different mechanisms, a combination therapy that targets two or more of these proteins thereof may be a more effective treatment. In fact, many related clinical trials are in progress and have shown a good effect.

The animal model expressing a B2M/FcRn fusion protein, and/or the animal model with additional genetic modifications can be used for determining effectiveness of a combination therapy.

In some embodiments, the combination of agents can include one or more agents selected from the group consisting of paclitaxel, cisplatin, carboplatin, pemetrexed, 5-FU, gemcitabine, oxaliplatin, docetaxel, and capecitabine.

In some embodiments, the combination of agents can include one or more agents selected from the group consisting of campothecin, doxorubicin, cisplatin, carboplatin, procarbazine, mechlorethamine, cyclophosphamide, adriamycin, ifosfamide, melphalan, chlorambucil, bisulfan, nitrosurea, dactinomycin, daunorubicin, bleomycin, plicomycin, mitomycin, etoposide, verpamil, podophyllotoxin, tamoxifen, taxol, transplatinum, 5-flurouracil, vincristin, vinblastin, and methotrexate.

In some embodiments, the combination of agents can include one or more antibodies that bind to CSF2, IL3, CSF1, IL15, PD-1, CTLA-4, LAG-3, BTLA, PD-L1, 4-1BB, CD27, CD28, SIRPα, CD47, TWO, TIGIT, GITR, and/or OX40.

Alternatively or in addition, the methods can also include performing surgery on the subject to remove at least a portion of the cancer, e.g., to remove a portion of or all of a tumor(s), from the subject.

EXAMPLES

The invention is further described in the following examples, which do not limit the scope of the invention described in the claims.

Materials and Methods

The following materials were used in the following examples.

B-NDG mice were obtained from Biocytogen Pharmaceuticals (Beijing) Co., Ltd. The catalog number is 110586.

BNDG-B2M-KO mice were obtained from Biocytogen Pharmaceuticals (Beijing) Co., Ltd. The catalog number is 110589.

C57BL/6 mice were purchased from the China Food and Drugs Research Institute National Rodent Experimental Animal Center.

NOD/scid mice were purchased from Beijing HFK Bio-Technology Co., Ltd.

Flow cytometer was purchased from Invitrogen with model Attune™ NxT.

Zombie NIR™ Fixable Viability Kit (DMSO) was purchased from BioLegend with catalog number 423106.

UCA kit was obtained from Beijing Biocytogen Co., Ltd. The catalog number is BCG-DX-001.

Ambion™ in vitro transcription kit was purchased from Ambion, Inc. The catalog number is AM1354.

Cas9 mRNA was obtained from SIGMA. The catalog number is CAS9MRNA-1EA.

Purified anti-mouse CD16/32 was purchased from BioLegend with catalog number 101302.

APC/Cy7 anti-mouse CD45 was purchased from BioLegend with catalog number 103116.

Brilliant Violet 510" anti-human CD45 was purchased from BioLegend with catalog number 304036.

PerCP anti-human CD3 was purchased from BioLegend with catalog number 300428.

Brilliant Violet 421™ anti-human CD4 was purchased from BioLegend with catalog number 300532.

PE anti-human CD8a was purchased from BioLegend with catalog number 300908.

FITC mouse anti-human CD56 was purchased from BD Pharmingen with catalog number 562794.

APC anti-human CD25 was purchased from BioLegend with catalog number 302610.

Brilliant Violet 711™ anti-human CD19 was purchased from BioLegend with catalog number 302246.

Human TruStrain FcX was purchased from BioLegend with catalog number 422302.

PE/Cy7 anti-human CD69 was purchased from BioLegend with catalog number 310912.

PerCP/Cy5.5 anti-mouse TCR β chain (mTCR-β) was purchased from BioLegend with catalog number 109228.

Brilliant Violet 605™ anti-mouse CD19 (mCD19) was purchased from BioLegend with catalog number 115540.

PE anti-mouse CD335 (NKp46) (mNKp46) was purchased from BioLegend with catalog number 102812.

FITC anti-mouse F4/80 (mF4-80+) was purchased from BioLegend with catalog number 123108.

Brilliant Violet 605™ anti-mouse/human CD11b was purchased from BioLegend with catalog number 101257.

PE/Cy™ 7 anti-mouse CD11c (mCD11c) was purchased from eBioscience, Inc. with catalog number 25011481.

APC anti-mouse Ly-6C (mLy6C) was purchased from BioLegend with catalog number 128016.

Brilliant Violet 421™ anti-mouse I-A/I-E was purchased from BioLegend with catalog number 107632.

PE anti-mouse H-2Kd (mH-2kd-PE) was purchased from BioLegend with catalog number 116607.

AffiniPure Goat Anti-Human IgG (H+L) was purchased from Jackson ImmunoResearch Inc. with catalog number 109-005-088.

Peroxidase-conjugated AffiniPure F(ab')$_2$ Fragment Goat Anti-HumanIgG Fc was purchased from Jackson ImmunoResearch Inc. with catalog number 109-036-098.

NcoI, NdeI, and BbsI restriction enzymes were purchased from NEB. The catalog numbers are R0193M, R0111S, and R0539S, respectively.

Example 1: Generation of an Immunodeficient Mice Expressing B2M/FcRn Fusion Protein The mouse B2M gene (NCBI Gene ID: 12010, Primary source: MGI: 88127, UniProt ID: P01887) is located in chromosome 2 of the mouse genome (from 122,147,687 to 122,153,082 of NC_000068.7). The transcript sequence NM_009735.3 is set forth in SEQ ID NO: 1, and the corresponding protein sequence NP_033865.2 is set forth in SEQ ID NO: 2. The mouse FcRn gene (NCBI Gene ID: 14132, Primary source: MGI: 103017, UniProt ID: Q61559) is located in chromosome 7 of the mouse genome (from 45,092,993 to 45,103,822 of NC_000073.6). The transcript sequence NM_010189.3 is set forth in SEQ ID NO: 3, and the corresponding protein sequence NP_034319.2 is set forth in SEQ ID NO: 4. Schematic diagrams of mouse B2M and FcRn gene loci are shown in FIG. 1.

Figure 2:
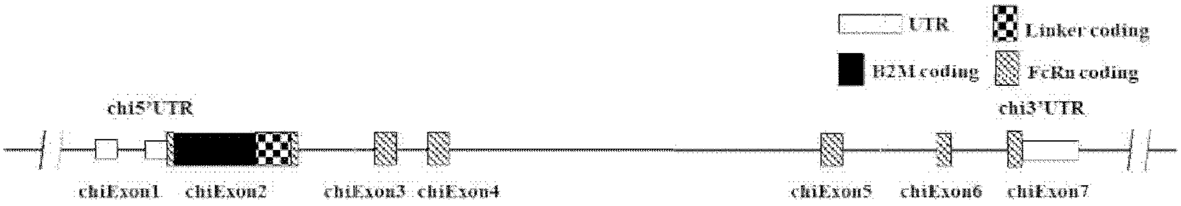
FIG. 2 shows a schematic diagram of B2M/FcRn fusion gene locus.

Cells from a non-human animal (e.g., a mouse) can be modified by gene editing technologies to knock a nucleotide sequence encoding an endogenous B2M protein (e.g., a mouse B2M protein) into the endogenous FcRn locus (e.g., the mouse FcRn locus), such that genetically-modified animal (e.g., the genetically-modified mouse) can express a B2M and FcRn protein complex. A schematic diagram of the modified FcRn locus is shown in FIG. 2. The DNA sequence of the modified FcRn gene is shown in SEQ ID NO: 45, and its transcribed mRNA sequence is shown in SEQ ID NO: 5, in which the mRNA sequence encoding FcRn (without a signal peptide) is set forth in SEQ ID NOs: 43; and the mRNA sequence encoding the signal peptide of FcRn is set forth in SEQ ID NO: 44. The amino acid sequence of the translated protein complex is shown in SEQ ID NO: 6, in which the amino acid sequence of the B2M protein is shown in SEQ ID NO: 40; the amino acid sequence of the FcRn protein is shown in SEQ ID NO: 41; and the amino acid sequence of the signal peptide is shown in SEQ ID NO: 42. Given that mouse FcRn and B2M have multiple subtypes or transcripts, the method described herein can be applied to other subtypes or transcripts.

The CRISPR/Cas system was applied for gene editing, and the targeting strategy is shown in FIG. 3. A targeting vector was designed, containing homologous arm sequences upstream and downstream of mouse FcRn gene, and an “A fragment” encoding mouse B2M protein. The upstream homologous arm sequence (5' homologous arm, SEQ ID NO: 7) has 99% homology with the nucleotide sequence 45103007-45104486 of NCBI accession number NC_000073.6, with a substitution of the “C” at position 45103046 to “G” and a substitution of the “C” at position 45103052 to “A”. The downstream homologous arm sequence (3' homologous arm, SEQ ID NO: 8) is identical to the nucleotide sequence 45101562-45103006 of NCBI accession number NC_000073.6. The mouse B2M nucleotide sequence (SEQ ID NO: 9) in the “A fragment” has 99% homology with the nucleotide sequence 112-408 of NCBI accession number NM_009735.3, with a substitution of the “C” at position 345 to “T”. A flexible linker (GGGGS)$_3$ was used to link the mouse B2M and FcRn protein sequences. The flexible linker is encoded by a 45 bp sequence set forth in SEQ ID NO: 10 (5'-GGAGGTGGCGGATCCGGCGGAGGCGGCTCGGGTGGCGGCGGCTCT-3').

The targeting vector was constructed, e.g., by restriction enzyme digestion/ligation, or gene synthesis. The constructed targeting vector sequence was preliminarily verified by restriction enzyme digestion, then verified by sequencing. The verified targeting vector was used for subsequent experiments.

The targeting sequences are important for the targeting specificity of sgRNAs and the efficiency of Cas9-induced cleavage. Specific sgRNA sequences were designed and synthesized that recognize the targeting sites (sgRNA1-sgRNA8), which are located within exon 2 and intron 2 of the FcRn gene of B-NDG mice (NOD/scid mice with a deletion of sequences spanning from exon 1 to exon 8 of CD132 gene). The targeting site sequence of each sgRNA on the FcRn gene locus is as follows:

```
sgRNA1 targeting site (SEQ ID NO: 11):
5'-CGGGTCACCCTGTCGGAATGGGG-3'

sgRNA2 targeting site (SEQ ID NO: 12):
5'-CCCATTCCGACAGGGTGACCCGG-3'

sgRNA3 targeting site (SEQ ID NO: 13):
5'-AGTGGCATCCCCATTCCGACAGG-3'

sgRNA4 targeting site (SEQ ID NO: 14):
5'-CCATGATGTCCTAGCCTTCATGG-3'

sgRNA5 targeting site (SEQ ID NO: 15):
5'-CTGAGCCCCAGGTCTGAGGCAGG-3'

sgRNA6 targeting site (SEQ ID NO: 16):
5'-GGAGGACCAACAAGAGGCTGAGG-3'
```

-continued

```
sgRNA7 targeting site (SEQ ID NO: 17):
5'-GAGTGTGTCAGGAAGGGGACAGG-3'

sgRNA8 targeting site (SEQ ID NO: 18):
5'-TTACCTGAGCCCCAGGTCTGAGG-3'
```

Figure 4:
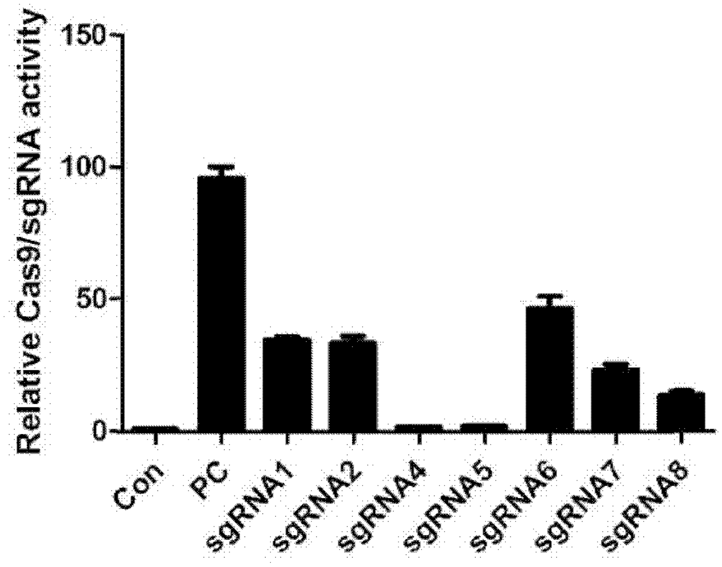
FIG. 4 shows the sgRNA activity detection results. Con is a negative control. PC is a positive control.

The UCA kit was used to detect the activities of sgRNAs. The results showed that the sgRNAs had different activities. The results are shown in the table below and FIG. 4. sgRNA6 was selected for subsequent experiments.

TABLE 3

UCA test results showing sgRNA activity

| Con. | 1.00 ± 0.08 | PC | 95.80 ± 4.35 |
|---|---|---|---|
| sgRNA1 | 34.49 ± 1.25 | sgRNA5 | 2.25 ± 0.32 |
| sgRNA2 | 33.34 ± 2.56 | sgRNA6 | 46.32 ± 4.61 |
| sgRNA3 | — | sgRNA7 | 23.21 ± 2.08 |
| sgRNA4 | 1.88 ± 0.10 | sgRNA8 | 13.82 ± 1.40 |

Oligonucleotides were added to the 5' end and a complementary strand to obtain a forward oligonucleotide and a reverse oligonucleotide (See the table below for the sequences). After annealing, the products were ligated to the pT7-sgRNA plasmid (the plasmid was first linearized with BbsI), respectively, to obtain expression vector pT7-FcRn-6.

TABLE 4 sgRNA6 sequences

| | |
|---|---|
| SEQ ID NO: 20 | Upstream: 5'-GGAGGACCAACAAGAGGCTG-3' |
| SEQ ID NO: 21 (forward oligonucleotide) | Upstream: 5'-TAGGGGAGGACCAACAAGAGGCTG-3' |
| SEQ ID NO: 22 | Downstream: 5'-CAGCCTCTTGTTGGTCCTCC-3' |
| SEQ ID NO: 23 (reverse oligonucleotide) | Downstream: 5'-AAACCAGCCTCTTGTTGGTCCTCC-3' |

The pT7-sgRNA vector was synthesized, which included a DNA fragment containing the T7 promoter and sgRNA scaffold (SEQ ID NO: 24), and was ligated to the backbone vector (Takara, Catalog number: 3299) after restriction enzyme digestion (EcoRI and BamHI). The resulting plasmid was confirmed by sequencing.

The pre-mixed Cas9 mRNA, the targeting vector, in vitro transcription products of the pT7-FcRn-6 plasmid (using Ambion™ in vitro transcription kit to carry out the transcription according to the method provided in the product instruction) were injected into the cytoplasm or nucleus of BNDG-B2M-KO mouse fertilized eggs with a microinjection instrument. The embryo microinjection was carried out according to the method described, e.g., in A. Nagy, et al., “Manipulating the Mouse Embryo: A Laboratory Manual (Third Edition),” Cold Spring Harbor Laboratory Press, 2006. The injected fertilized eggs were then transferred to a culture medium to culture for a short time and then was transplanted into the oviduct of the recipient mouse to produce the genetically modified mice (F0 generation). The mouse population was further expanded by cross-breeding and self-breeding to establish a stable strain of B2M and FcRn fusion gene immunodeficiency mice (hereinafter referred to as BNDG-B2M/FcRn mice).

Figures 5A, 5B:
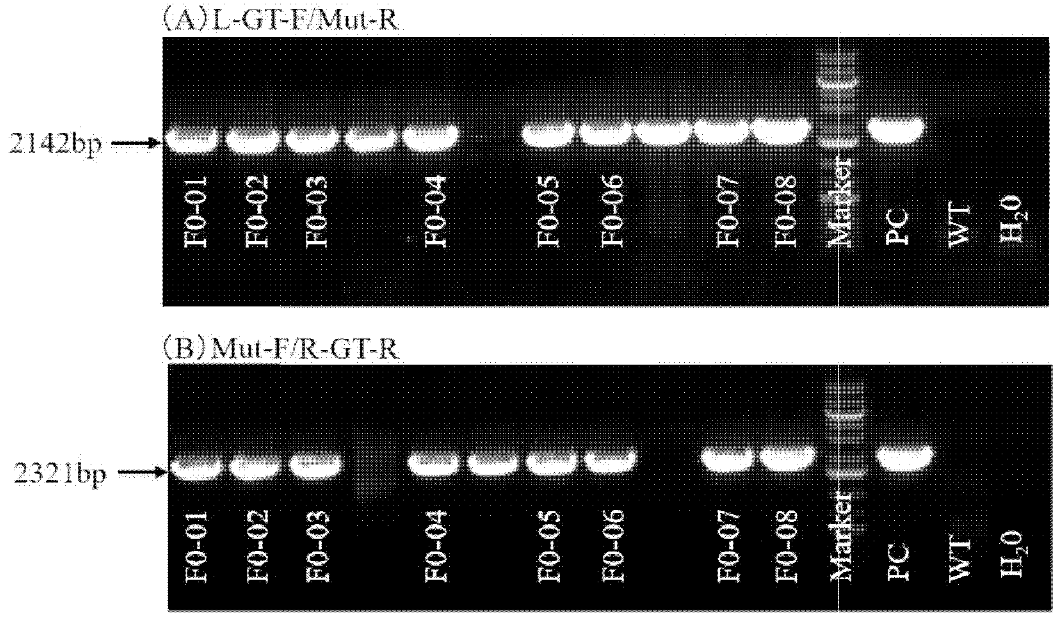
FIG. 5A shows PCR identification results of F0 generation mice by primers L-GT-F and Mut-R. F0-01, F0-02, F0-03, F0-04, F0-05, F0-06, F0-07, and F0-08 are mouse numbers. PC is a positive control. WT is a wild-type control. $H_2O$ is a water control.
FIG. 5B shows PCR identification results of F0 generation mice by primers Mut-F and R-GT-R. F0-01, F0-02, F0-03, F0-04, F0-05, F0-06, F0-07, and F0-08 are mouse numbers. PC is a positive control. WT is a wild-type control. $H_2O$ is a water control.
Figures 6A, 6B, 6C, 6D, 6E, 6F:
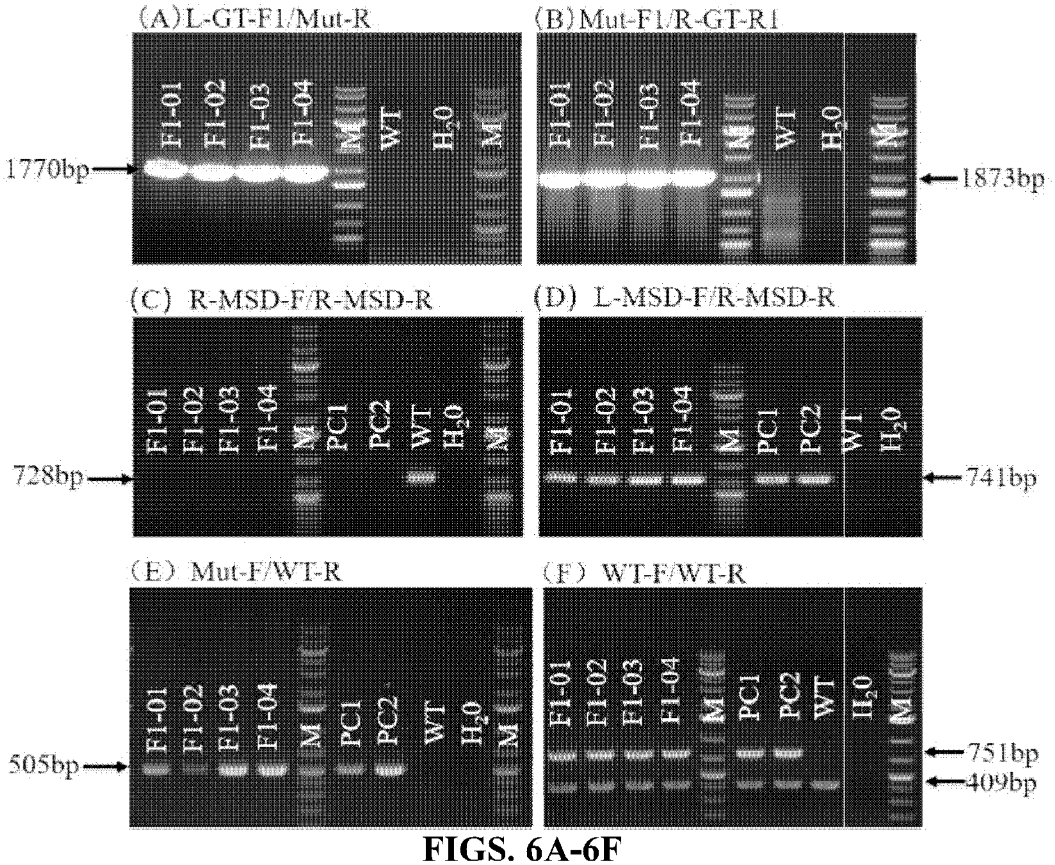
FIGS. 6A-6F show PCR identification results of F1 generation mice. M is a marker. WT is a wild-type control. $H_2O$ is a water control. PC1 and PC2 are positive controls. F1-01, F1-02, F1-03, and F1-04 are mouse numbers.

Experiments were performed to identify somatic cell genotype of the F0 generation mice. For example, PCR analysis was performed using mouse tail genomic DNA of the F0 generation mice. The PCR analysis results for some of the F0 mice are shown in FIGS. 5A-5B, in which 8 mice numbered F0-01 to F0-08 were identified as positive mice. The F0 generation PCR analysis included the primers described in the table below:

TABLE 5

Primers used in F0 PCR analysis

| Primer | SEQ ID NO | Sequence (5'-3') | Target band size |
|---|---|---|---|
| L-GT-F | SEQ ID NO: 25 | GTAGCTGTCTTCAGACACTCCAGAA | Mut: 2142 bp |
| Mut-R | SEQ ID NO: 26 | TGCAGGCATATGTATCAGTCTCAGT | |
| Mut-F | SEQ ID NO: 27 | AATTCAAGTATACTCACGCCACCCA | Mut: 2321 bp |
| R-GT-R | SEQ ID NO: 28 | TAAGTTCAAGTCCCAGCAACCACAT | |

The primer L-GT-F is located upstream of the 5' homologous arm. R-GT-R is located downstream of the 3' homologous arm. Both L-GT-R and R-GT-F are located on the inserted B2M sequence.

The positive F0 generation BNDG-B2M/FcRn mice were bred with B-NDG-B2M-KO mice to generate F1 generation mice. The same method (e.g., PCR) was used for genotypic identification of the F1 generation mice. As shown in FIGS. 6A-6F, 4 mice numbered F1-01, F1-02, F1-03, and F1-04 were identified as positive mice.

The F1 generation PCR analysis included the primers described in the table below.

TABLE 6

Primers used in F1 PCR analysis

| Primer | SEQ ID NO | Sequence (5'-3') | Target band size |
|---|---|---|---|
| L-GT-F1 | SEQ ID NO: 29 | TTGCTTCTGTCTTTCAAGTGTGTGGG | Mut: 1770 bp |
| Mut-R | SEQ ID NO: 26 | TGCAGGCATATGTATCAGTCTCAGT | |
| Mut-F1 | SEQ ID NO: 30 | ATTCAAGTATACTCACGCCACCCACC | Mut: 1873 bp |
| R-GT-R1 | SEQ ID NO: 31 | AGGCTGAGACCAAGAGGATGACAAG | |
| R-MSD-F | SEQ ID NO: 32 | CTGCTTCCCTCTTTCCTGAGCTTCC | WT: 728 bp |
| R-MSD-R | SEQ ID NO: 33 | AAACCCATGCAGGCTGTGTAACTGA | |
| L-MSD-F | SEQ ID NO: 34 | GAATAAATGAAGGCGGTCCCAGGCT | Mut: 741 bp |
| R-MSD-R | SEQ ID NO: 33 | AAACCCATGCAGGCTGTGTAACTGA | |
| Mut-F | SEQ ID NO: 27 | AATTCAAGTATACTCACGCCACCCA | Mut: 505 bp |
| WT-R | SEQ ID NO: 35 | ACGAGCCTGAGATTGTCAAGTGTAT | |
| WT-F | SEQ ID NO: 36 | GTGAAAGTTCACAGAGGAACACTCC | WT: 409 bp |
| WT-R | SEQ ID NO: 35 | ACGAGCCTGAGATTGTCAAGTGTAT | Mut: 751 bp |

The primers L-GT-F1 and R-GT-R1 are respectively located upstream of the 5' homologous arm and downstream of the 3' homologous arm of the FcRn gene. Mut-F1 is located on the inserted B2M sequence. R-MSD-F, R-MSD-R, and L-MSD-F are located upstream of intron 2, intron 3, and exon 1 of the B2M gene, respectively.

The 4 positive F1 generation mice were further analyzed by Southern Blot, to confirm if random insertions were introduced. Specifically, mouse tail genomic DNA was extracted, digested with NcoI or NdeI restriction enzyme, transferred to a membrane, and then hybridized with probes. The 5' probe and 3' probes are located upstream of the 5' homologous arm and on the 3' homology arm, respectively (See the table below).

TABLE 7

Probe length and target fragment

| Restriction enzyme | Probe | WT size | Targeted size |
|---|---|---|---|
| NcoI | 3' probe | 7.7 kb | 3.6 kb |
| NdeI | 5' probe | 5.7 kb | 3.1 kb |

The probes were synthesized using the following primers:

3' Probe-F (SEQ ID NO: 19):
5'-GTTTGAGGAAGGATAATGGGTCTGG-3'

3' Probe-R (SEQ ID NO: 37):
5'-CATCCACAGATTAGCAACGATTTCC-3'

5' Probe-F (SEQ ID NO: 38):
5'-GCTAGCATCAGAAGATCAGGACTCA-3'

-continued

5' Probe-R (SEQ ID NO: 39):
5'-TAGAAAGTCAACCACTCCTACCTGC-3'

Figure 7:
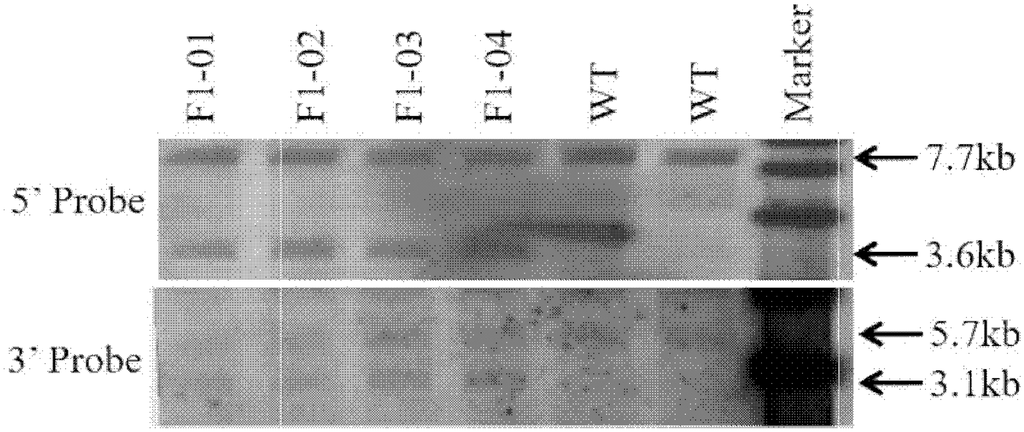
FIG. 7 shows an exemplary Southern Blot results of F1 generation BNDG-B2M/FcRn mice using the 5' Probe and 3' Probe. F1-01, F1-02, F1-03, and F1-04 are positive mouse numbers. WT is a wild-type control.
Figures 8A, 8P:
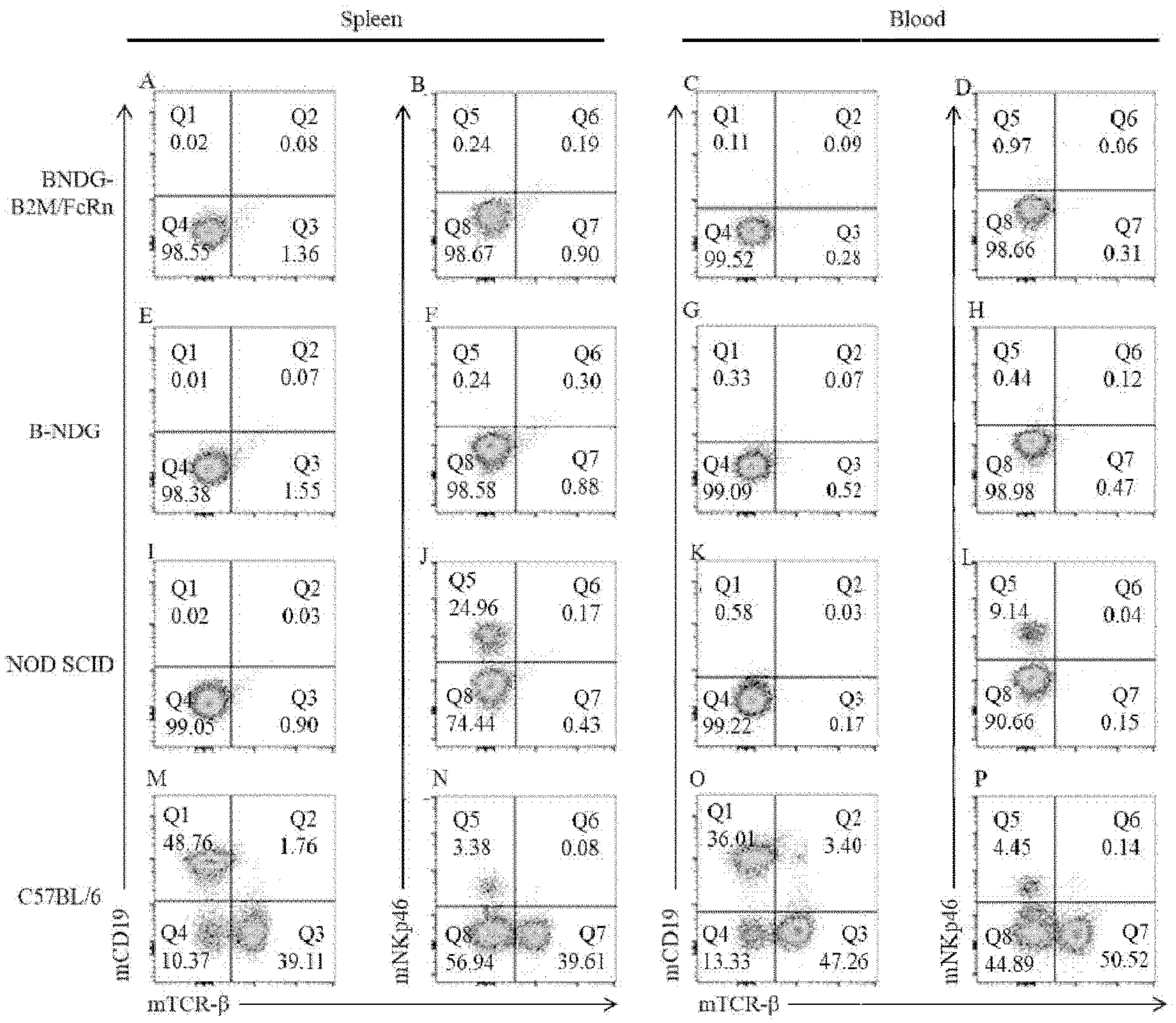
FIG. 8A shows a flow cytometry detection result from spleen cells of BNDG-B2M/FcRn mice. The cells were stained with Brilliant Violet 605™ anti-mouse CD19 (mCD19) and PerCP/Cy5.5 anti-mouse TCR β chain (mTCR-β).
FIG. 8P shows a flow cytometry detection result from blood cells of C57BL/6 mice. The cells were stained with PE anti-mouse CD335 (NKp46) (mNKp46) and PerCP/Cy5.5 anti-mouse TCR β chain (mTCR-β).

The detection result of Southern Blot is shown in FIG. 7. In view of the hybridization results by the 5' and 3' probes, the four F1 generation mice were confirmed to be positive heterozygotes and no random insertions were detected. This indicates that this method can be used to construct genetically engineered mice (i.e., BNDG-B2M/FcRn mice) that can be passed stably without random insertions. Specifically in the BNDG-B2M/FcRn mice, the endogenous B2M gene is knocked out, but a cDNA sequence encoding B2M protein is inserted at the FcRn gene locus to generate a B2M/FcRn fusion gene.

Example 2. Immunophenotyping Detection of BNDG-B2M/FcRn Mice

F2 generation homozygous BNDG-B2M/FcRn mice can be obtained by breeding the F1 generation mice. To confirm whether the differentiation of B cells, T cells, NK cells, dendritic cells (DC), macrophages, and monocytes in the F2 generation mice was consistent with that of B-NDG mice, and whether there was a difference as compared with other immunodeficient mice (e.g., NOD/scid mice) or wild-type C57BL/6 mice, the immune cell subpopulations of the mice were detected by flow cytometry. Specifically, 6-week-old BNDG-B2M/FcRn homozygous mice, B-NDG mice, NOD/scid mice, and wild-type C57BL/6 mice (females) were selected (5 mice per group). After euthanasia, samples of bone marrow (BM), spleen, and blood from each mouse were collected and a single-cell suspension was prepared from the samples. After treating the single-cell suspension with the blocking antibody Purified anti-mouse CD16/32 and the Zombie NIR™ Fixable Viability Kit (DMSO), the cells were labeled with: Brilliant Violet 510™ anti-mouse CD45 (an anti-mouse CD45 antibody); PerCP/Cy5.5 anti-mouse TCR β chain (used to label T cells); Brilliant Violet 605™ anti-mouse CD19 (used to label B cells); PE anti-mouse CD335 (NKp46) (used to label NK cells); FITC anti-mouse F4/80 (used to label microphages); Brilliant Violet 605™ anti-mouse/human CD11b and PE/Cy™ 7 anti-mouse CD11c (used to label dendritic cells); APC anti-mouse Ly-6C and Brilliant Violet 421™ anti-mouse I-A/I-E (used to label monocytes); and PE anti-mouse H-2Kd (used to label MHC class I molecules), respectively, followed by flow cytometry analysis.

The detection results of T cells, B cells, and NK cells in the spleen and blood samples of BNDG-B2M/FcRn mice, B-NDG mice, NOD/scid mice and wild-type C57BL/6 mice are shown in FIGS. 8A-8H and the table below. T cells (FIGS. 8M, 8N, 8O, and 8P), B cells (FIGS. 8M and 8O) and NK cells (FIGS. 8N and 8P) were detected in the blood and spleen samples of wild-type C57BL/6 mice. No T cells (FIGS. 8I, 8J, 8K, and 8L) or B cells (FIGS. 8I and 8K), but NK cells were detected (FIGS. 8J and 8L) were detected in NOD/scid mice. No T cells (FIGS. 8A-8H), B cells (FIGS. 8A, 8C, 8E, and 8G), or NK cells (FIGS. 8B, 8D, 8F, and 8H) were detected in BNDG-B2M/FcRn and B-NDG mice. The results indicate that, compared with NOD/scid mice, BNDG-B2M/FcRn mice did not reduce the degree of immunodeficiency; and both the BNDG-B2M/FcRn mice and B-NDG mice had a higher degree of immunodeficiency.

TABLE 8

Detection results of T cells, B cells and NK cells in mouse spleen or blood samples

| | Spleen | | | | Blood | | | |
|---|---|---|---|---|---|---|---|---|
| | B cells | T cells | | NK cells | B cells | T cells | | NK cells |
| Group | mCD19+/ mTCR-β− | mCD19−/ mTCR-β+ | mNKp46−/ mTCR-β+ | mNKp46+/ mTCR-β− | mCD19+/ mTCR-β− | mCD19−/ mTCR-β+ | mNKp46−/ mTCR-β+ | mNKp46+/ mTCR-β− |
| BNDG-B2M/ FcRn | 0.02% | 1.36% | 0.90% | 0.24% | 0.11% | 0.28% | 0.31% | 0.97% |
| B-NDG | 0.01% | 1.55% | 0.88% | 0.24% | 0.33% | 0.52% | 0.47% | 0.44% |
| NOD SCID | 0.02% | 0.90% | 0.43% | 24.96% | 0.58% | 0.17% | 0.15% | 9.14% |
| C57BL/6 | 48.76% | 39.11% | 39.61% | 3.38% | 36.01% | 47.26% | 50.52% | 4.45% |

Figures 9A, 9B, 9C, 9D, 9E, 9F, 9G, 9H, 9I, 9J, 9K, 9L:
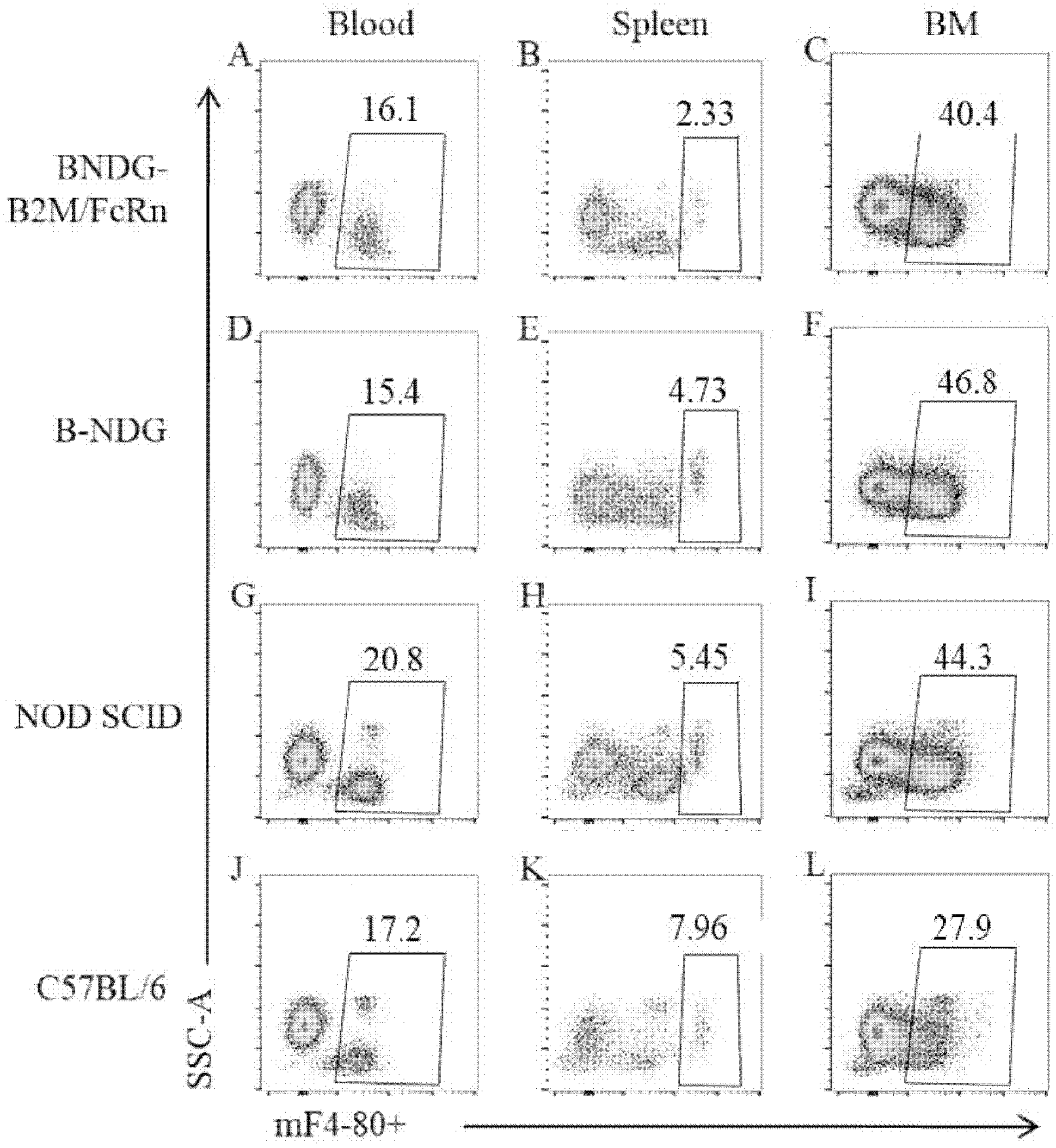
FIG. 9A shows a flow cytometry detection result from blood cells of BNDG-B2M/FcRn mice. The cells were stained with FITC anti-mouse F4/80 (mF4-80+) and the percentage of microphages is indicated.
FIG. 9B shows a flow cytometry detection result from spleen cells of BNDG-B2M/FcRn mice. The cells were stained with FITC anti-mouse F4/80 (mF4-80+) and the percentage of microphages is indicated.
FIG. 9C shows a flow cytometry detection result from bone marrow (BM) cells of BNDG-B2M/FcRn mice. The cells were stained with FITC anti-mouse F4/80 (mF4-80+) and the percentage of microphages is indicated.
FIG. 9D shows a flow cytometry detection result from blood cells of B-NDG mice. The cells were stained with FITC anti-mouse F4/80 (mF4-80+) and the percentage of microphages is indicated.
FIG. 9E shows a flow cytometry detection result from spleen cells of B-NDG mice. The cells were stained with FITC anti-mouse F4/80 (mF4-80+) and the percentage of microphages is indicated.
FIG. 9F shows a flow cytometry detection result from bone marrow (BM) cells of B-NDG mice. The cells were stained with FITC anti-mouse F4/80 (mF4-80+) and the percentage of microphages is indicated.
FIG. 9G shows a flow cytometry detection result from blood cells of NOD/scid mice (NOD SCID). The cells were stained with FITC anti-mouse F4/80 (mF4-80+) and the percentage of microphages is indicated.
FIG. 9H shows a flow cytometry detection result from spleen cells of NOD/scid mice (NOD SCID). The cells were stained with FITC anti-mouse F4/80 (mF4-80+) and the percentage of microphages is indicated.
FIG. 9I shows a flow cytometry detection result from bone marrow (BM) cells of NOD/scid mice (NOD SCID). The cells were stained with FITC anti-mouse F4/80 (mF4-80+) and the percentage of microphages is indicated.
FIG. 9J shows a flow cytometry detection result from blood cells of C57BL/6 mice. The cells were stained with FITC anti-mouse F4/80 (mF4-80+) and the percentage of microphages is indicated.
FIG. 9K shows a flow cytometry detection result from spleen cells of C57BL/6 mice. The cells were stained with FITC anti-mouse F4/80 (mF4-80+) and the percentage of microphages is indicated.
FIG. 9L shows a flow cytometry detection result from bone marrow (BM) cells of C57BL/6 mice. The cells were stained with FITC anti-mouse F4/80 (mF4-80+) and the percentage of microphages is indicated.
Figures 10A, 10B, 10C, 10D, 10E, 10F, 10G, 10H, 10I, 10J, 10K, 10L:
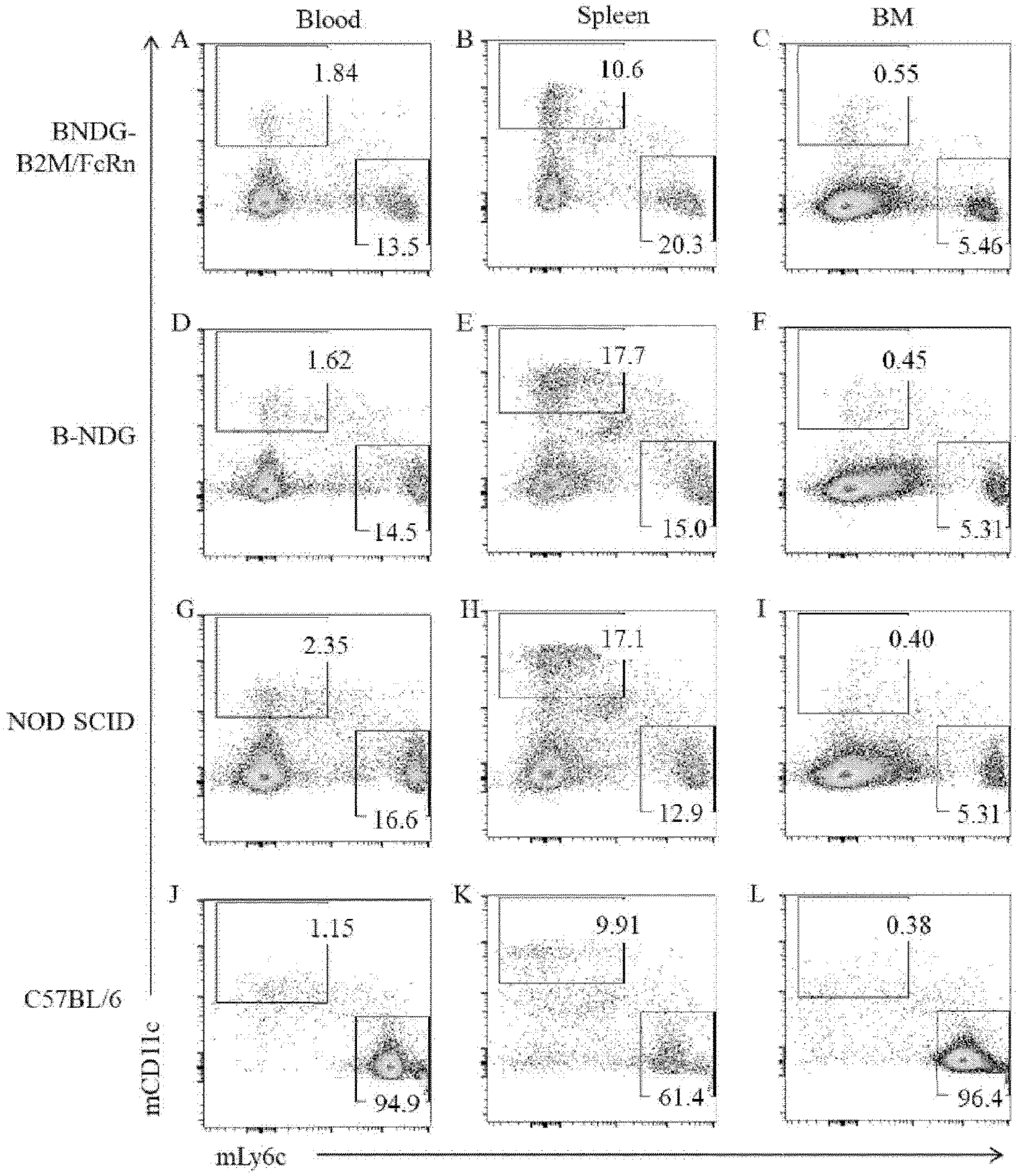
FIG. 10A shows a flow cytometry detection result from blood cells of BNDG-B2M/FcRn mice. The cells were stained with Brilliant Violet 605™ anti-mouse/human CD11b and PE/Cy™ 7 anti-mouse CD11c (mCD11c) and APC anti-mouse Ly-6C (mLy6c). The percentage of dendritic cells (upper left) and monocytes (lower right) are indicated.
FIG. 10B shows a flow cytometry detection result from spleen cells of BNDG-B2M/FcRn mice. The cells were stained with Brilliant Violet 605™ anti-mouse/human CD11b and PE/Cy™ 7 anti-mouse CD11c (mCD11c) and APC anti-mouse Ly-6C (mLy6c). The percentage of dendritic cells (upper left) and monocytes (lower right) are indicated.
FIG. 10C shows a flow cytometry detection result from bone marrow (BM) cells of BNDG-B2M/FcRn mice. The cells were stained with Brilliant Violet 605™ anti-mouse/human CD11b and PE/Cy™ 7 anti-mouse CD11c (mCD11c) and APC anti-mouse Ly-6C (mLy6c). The percentage of dendritic cells (upper left) and monocytes (lower right) are indicated.
FIG. 10D shows a flow cytometry detection result from blood cells of B-NDG mice. The cells were stained with Brilliant Violet 605™ anti-mouse/human CD11b and PE/Cy™ 7 anti-mouse CD11c (mCD11c) and APC anti-mouse Ly-6C (mLy6c). The percentage of dendritic cells (upper left) and monocytes (lower right) are indicated.
FIG. 10E shows a flow cytometry detection result from spleen cells of B-NDG mice. The cells were stained with Brilliant Violet 605™ anti-mouse/human CD11b and PE/Cy™ 7 anti-mouse CD11c (mCD11c) and APC anti-mouse Ly-6C (mLy6c). The percentage of dendritic cells (upper left) and monocytes (lower right) are indicated.
FIG. 10F shows a flow cytometry detection result from bone marrow (BM) cells of B-NDG mice. The cells were stained with Brilliant Violet 605™ anti-mouse/human CD11b and PE/Cy™ 7 anti-mouse CD11c (mCD11c) and APC anti-mouse Ly-6C (mLy6c). The percentage of dendritic cells (upper left) and monocytes (lower right) are indicated.
FIG. 10G shows a flow cytometry detection result from blood cells of NOD/scid mice (NOD SCID). The cells were stained with Brilliant Violet 605™ anti-mouse/human CD11b and PE/Cy™ 7 anti-mouse CD11c (mCD11c) and APC anti-mouse Ly-6C (mLy6c). The percentage of dendritic cells (upper left) and monocytes (lower right) are indicated.
FIG. 10H shows a flow cytometry detection result from spleen cells of NOD/scid mice (NOD SCID). The cells were stained with Brilliant Violet 605™ anti-mouse/human CD11b and PE/Cy™ 7 anti-mouse CD11c (mCD11c) and APC anti-mouse Ly-6C (mLy6c). The percentage of dendritic cells (upper left) and monocytes (lower right) are indicated.
FIG. 10I shows a flow cytometry detection result from bone marrow (BM) cells of NOD/scid mice (NOD SCID). The cells were stained with Brilliant Violet 605™ anti-mouse/human CD11b and PE/Cy™ 7 anti-mouse CD11c (mCD11c) and APC anti-mouse Ly-6C (mLy6c). The percentage of dendritic cells (upper left) and monocytes (lower right) are indicated.
FIG. 10J shows a flow cytometry detection result from blood cells of C57BL/6 mice. The cells were stained with Brilliant Violet 605™ anti-mouse/human CD11b and PE/Cy™ 7 anti-mouse CD11c (mCD11c) and APC anti-mouse Ly-6C (mLy6c). The percentage of dendritic cells (upper left) and monocytes (lower right) are indicated.
FIG. 10K shows a flow cytometry detection result from spleen cells of C57BL/6 mice. The cells were stained with Brilliant Violet 605™ anti-mouse/human CD11b and PE/Cy™ 7 anti-mouse CD11c (mCD11c) and APC anti-mouse Ly-6C (mLy6c). The percentage of dendritic cells (upper left) and monocytes (lower right) are indicated.
FIG. 10L shows a flow cytometry detection result from bone marrow (BM) cells of C57BL/6 mice. The cells were stained with Brilliant Violet 605™ anti-mouse/human CD11b and PE/Cy™ 7 anti-mouse CD11c (mCD11c) and APC anti-mouse Ly-6C (mLy6c). The percentage of dendritic cells (upper left) and monocytes (lower right) are indicated.
Figures 11A, 11B, 11C, 11D, 11E, 11F, 11G, 11H, 11I:
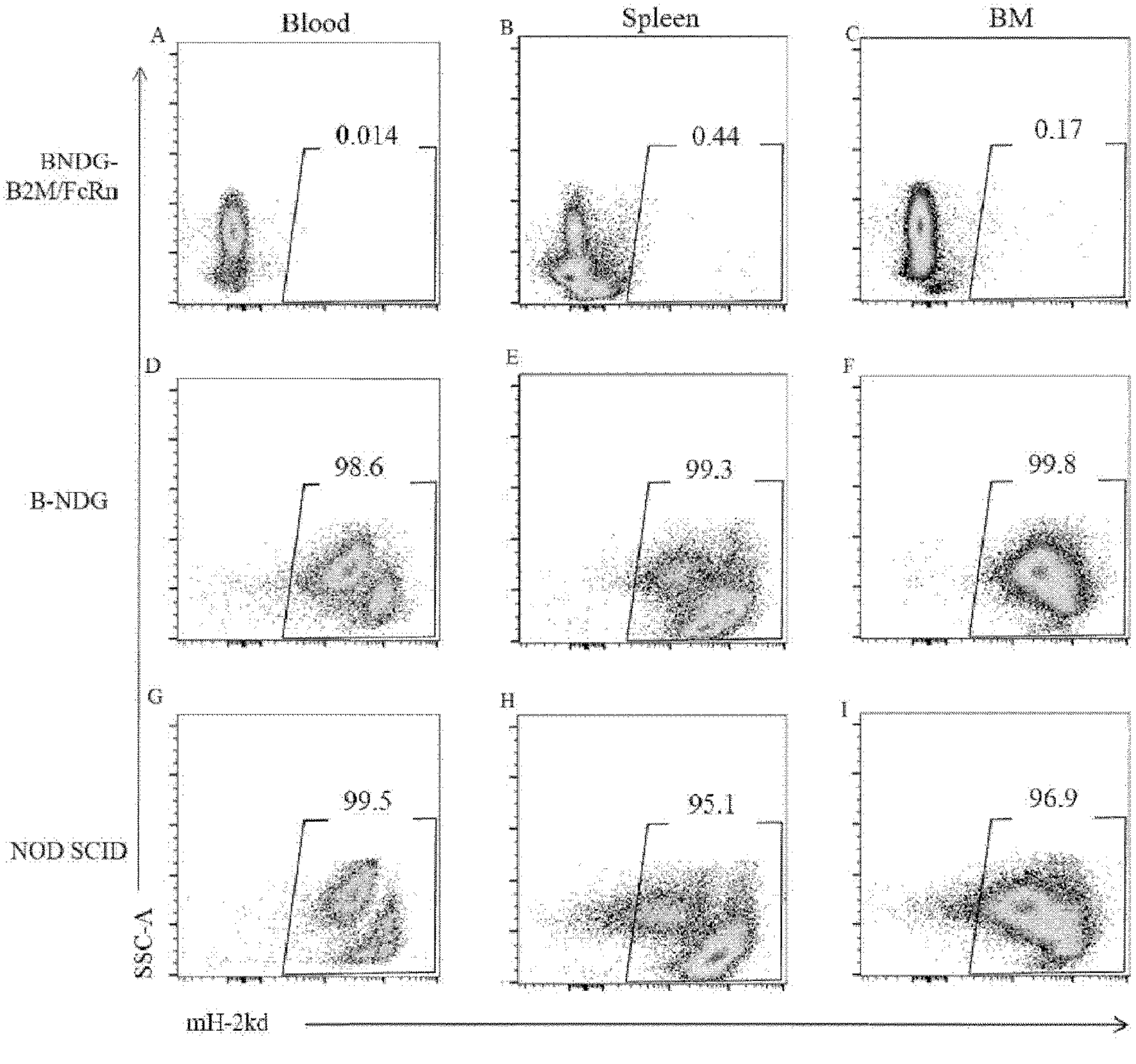
FIG. 11A shows a flow cytometry detection result from blood cells of BNDG-B2M/FcRn mice. The cells were stained with PE anti-mouse H-2Kd (mH-2kd) and the percentage of MHC class I positive cells are indicated.
FIG. 11B shows a flow cytometry detection result from spleen cells of BNDG-B2M/FcRn mice. The cells were stained with PE anti-mouse H-2Kd (mH-2kd) and the percentage of MHC class I positive cells are indicated.
FIG. 11C shows a flow cytometry detection result from bone marrow (BM) cells of BNDG-B2M/FcRn mice. The cells were stained with PE anti-mouse H-2Kd (mH-2kd) and the percentage of MHC class I positive cells are indicated.
FIG. 11D shows a flow cytometry detection result from blood cells of B-NDG mice. The cells were stained with PE anti-mouse H-2Kd (mH-2kd) and the percentage of MHC class I positive cells are indicated.
FIG. 11E shows a flow cytometry detection result from spleen cells of B-NDG mice. The cells were stained with PE anti-mouse H-2Kd (mH-2kd) and the percentage of MHC class I positive cells are indicated.
FIG. 11F shows a flow cytometry detection result from bone marrow (BM) cells of B-NDG mice. The cells were stained with PE anti-mouse H-2Kd (mH-2kd) and the percentage of MHC class I positive cells are indicated.
FIG. 11G shows a flow cytometry detection result from blood cells of NOD/scid mice (NOD SCID). The cells were stained with PE anti-mouse H-2Kd (mH-2kd) and the percentage of MHC class I positive cells are indicated.
FIG. 11H shows a flow cytometry detection result from spleen cells of NOD/scid mice (NOD SCID). The cells were stained with PE anti-mouse H-2Kd (mH-2kd) and the percentage of MHC class I positive cells are indicated.
FIG. 11I shows a flow cytometry detection result from bone marrow (BM) cells of NOD/scid mice (NOD SCID). The cells were stained with PE anti-mouse H-2Kd (mH-2kd) and the percentage of MHC class I positive cells are indicated.

The results of macrophage detection in spleen, blood and bone marrow samples of BNDG-B2M/FcRn mice, B-NDG mice, NOD SCID mice, and wild-type C57BL/6 mice are shown in FIGS. 9A-9L. In the spleen of BNDG-B2M/FcRn mice, B-NDG mice, and NOD/scid mice, a lower amount of macrophages were detected than the microphage levels in the spleen of wild-type C57BL/6 mice (FIGS. 9B, 9E, 9H, and 9K). In the blood of BNDG-B2M/FcRn mice, and B-NDG mice, a lower amount of macrophages were detected than the microphage levels in the blood of wild-type C57BL/6 mice (FIGS. 9A, 9D, and 9J). In particular, compared with NOD/scid mice, BNDG-B2M/FcRn mice and B-NDG mice had less macrophages in blood and spleen, thereby rendering a higher degree of immunodeficiency in such mice.

The detection results of DC and monocytes in the spleen, blood, and bone marrow samples of BNDG-B2M/FcRn mice, B-NDG mice, NOD/scid mice, and wild-type C57BL/6 mice are shown in FIGS. 10A-10L and the table below. DC and monocytes were detected in blood, spleen, and bone marrow samples of BNDG-B2M/FcRn mice, B-NDG mice, NOD/scid mice, and wild-type C57BL/6 mice (FIGS. 10A-10I). The results indicate that the degree of immunodeficiency of BNDG-B2M/FcRn mice is similar to that of B-NDG mice.

TABLE 9

Detection results of DC and monocytes in mouse spleen, blood and bone marrow samples

| | Blood | | Spleen | | BM | |
|---|---|---|---|---|---|---|
| Group | DC cells | Monocytes | DC cells | Monocytes | DC cells | Monocytes |
| BNDG-B2M/FcRn | 1.84% | 13.5% | 10.6% | 20.3% | 0.55% | 5.46% |
| B-NDG | 1.62% | 14.5% | 17.7% | 15.0% | 0.45% | 5.31% |
| NOD SCID | 2.35% | 16.6% | 17.1% | 12.9% | 0.40% | 5.31% |
| C57BL/6 | 1.15% | 94.9% | 9.91% | 61.4% | 0.38% | 96.4% |

The detection results of MHC class I molecules in the spleen, blood, and bone marrow samples of BNDG-B2M/FcRn mice, B-NDG mice, and NOD/scid mice are shown in FIGS. 11A-11I. The results showed that MHC class I molecules were detected in the blood, spleen, and bone marrow samples of B-NDG mice and NOD SCID mice (FIGS. 11D-11I). However, no MHC class I molecules were detected in blood, spleen, and bone marrow samples (FIGS. 11A-11C) of BNDG-B2M/FcRn mice. The results indicate that lack of free B2M protein expression in BNDG-B2M/FcRn mice hindered the expression of MHC class I molecules.

Example 3. Histopathological Section of Spleen of BNDG-B2M/FcRn Mice

The spleen tissues of 6-week-old C57BL/6 wild-type mice, NOD/scid mice, B-NDG mice, and BNDG-B2M/FcRn mice were paraffin-embedded, sectioned, and stained with hematoxylin and eosin (H&E). The histological morphology of mouse spleen was observed under a microscope.

Figures 12A, 12B, 12C, 12D, 12E, 12F:
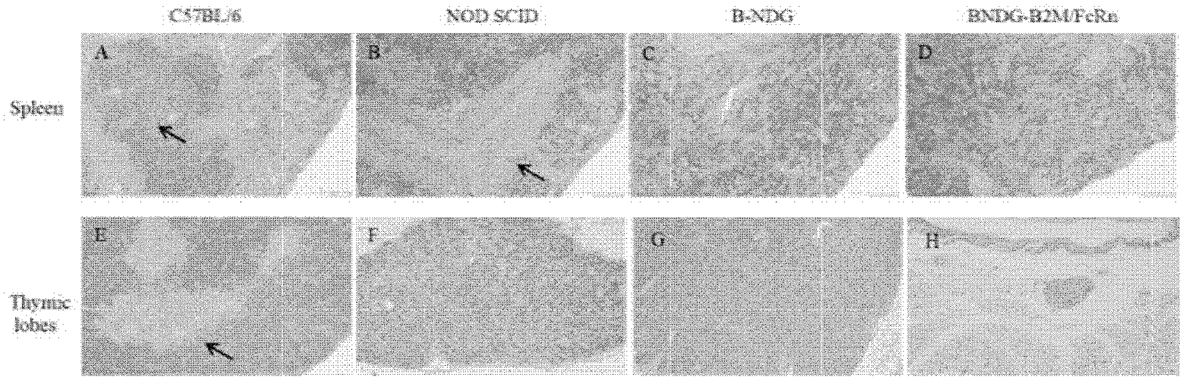
FIG. 12A shows H&E stain result of spleen tissues from C57BL/6 mice.
FIG. 12B shows H&E stain result of spleen tissues from NOD/scid mice (NOD SCID).
FIG. 12C shows H&E stain result of spleen tissues from B-NDG mice.
FIG. 12D shows H&E stain result of spleen tissues from BNDG-B2M/FcRn mice.
FIG. 12E shows H&E stain result of thymic lobes (in spleen) of C57BL/6 mice.
FIG. 12F shows H&E stain result of thymic lobes (in spleen) of NOD/scid mice (NOD SCID).

The results of H&E staining of mouse spleen tissue are shown in FIGS. 12A-12F. The spleen structure of the C57BL/6 wild-type mice was normal; the boundaries of follicles were clear (FIG. 12A); the thymus lobe structure was also normal; and the cortex boundary was clear (FIG. 12E). The spleens of NOD/scid mice showed hypoplasia of white pulp (FIG. 12B), hypoplasia of thymus lobe, and lack of clear cortex (FIG. 12F). The follicular structure in the spleen of B-NDG and BNDG-B2M/FcRn mice was completely lost (FIGS. 12C-12D). B-NDG mouse thymus lobe showed hypoplasia and lacked clear cortex structures (FIG. 12G), and BNDG-B2M/FcRn mice did not show thymic lobes in the standard anatomical position (FIG. 1211).

Example 4. Pharmacokinetics (PK) in BNDG-B2M/FcRn Mice

A double-antibody sandwich ELISA method was used to detect the PK of human immunoglobulin (hIgG) in B-NDG mice, BNDG-B2M-KO mice, BNDG-B2M/FcRn mice, and wild-type C57BL/6 mice.

Specifically, 6-week-old BNDG-B2M/FcRn homozygous mice, BNDG-B2M-KO mice, B-NDG mice, and C57BL/6 wild-type mice were selected (5 mice per group). All mice were fasted (except water) for 12 hours prior to the experiment. After fasting, 10 mg/kg of hIgG was intravenously (i.v.) injected through the tail vein, and 60 μL of blood from the orbital venous sinus was collected from the mice at the following time points: 3 days prior to hIgG administration; 15 minutes, 6 hours, 24 hours, 48 hours, 96 hours, 144 hours, 192 hours, 288 hours, and 384 hours after administration. The serum was isolated by centrifugation, and was then frozen for subsequence use. The specific grouping and dosage regimen are shown in the table below.

TABLE 10

Grouping and dosing schedule

| Group | Animal | Number | Treatment | Dose level (mg/kg) | Administration route | Administration frequency and total times |
|---|---|---|---|---|---|---|
| G1 | B-NDG | 5 | hIgG | 10 | i.v. | Single administration |
| G2 | BNDG-B2M-KO | 5 | hIgG | 10 | i.v. | Single administration |
| G3 | BNDG-B2M/FcRn | 5 | hIgG | 10 | i.v. | Single administration |
| G4 | C57BL/6 | 5 | hIgG | 10 | i.v. | Single administration |

Figure 13:
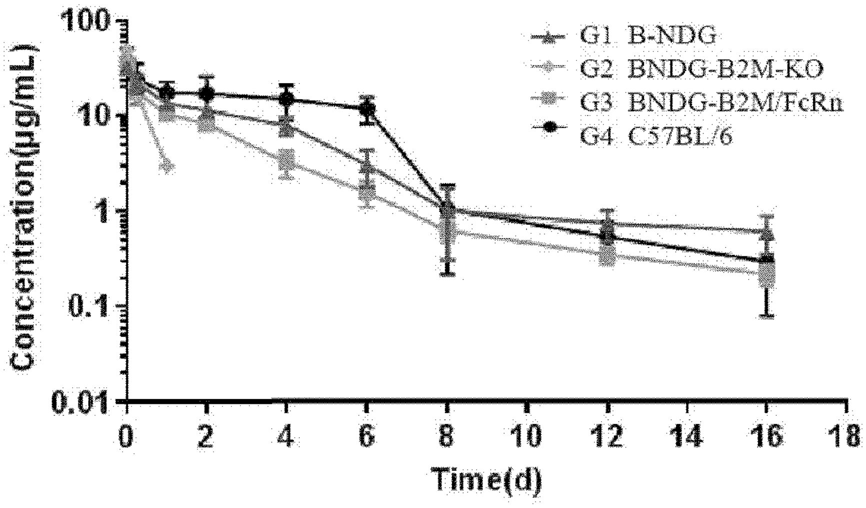
FIG. 13 shows the blood hIgG concentration-time curve in B-NDG mice (G1), BNDG-B2M-KO mice (G2), BNDG-B2M/FcRn mice (G3), and C57BL/6 mice (G4).

The double-antibody sandwich ELISA method was used to detect the hIgG concentration in each serum sample. Specifically, affinity-purified goat anti-human IgG capture antibody AffiniPure Goat Anti-Human IgG (H+L) was used to coat a 96-well ELISA plate. The plate was washed by phosphate-buffered saline (PBS) to remove excess capture antibody and the serum samples were added to the plate. Afterwards, the detection antibody horseradish peroxidase (HRP) conjugated AffiniPure $F(ab')_2$ Fragment Goat Anti-Human IgG Fc and a color development reagent were added to the plate. The blood concentration-time curve was drawn using the ELISA detection results. The curves of hIgG concentration in mouse serum over time at each time point in the four groups are shown in FIG. 13. There was no significant difference of the PK results of BNDG-B2M/FcRn mice and B-NDG mice, as compared with that of the wild-type C57BL/6 mice. However, the blood hIgG concentration in the BNDG-B2M-KO mice was not detected at any time point after the second day. Because the B2M gene in the BNDG-B2M-KO mice was knocked out, the FcRn/B2M-mediated antibody endocytosis was impaired, which could have resulted in a rapid clearance of the antibody. In the BNDG-B2M/FcRn mice prepared in Example 1, the expressed B2M/FcRn protein complex completely rescued the defect of impaired endocytosis, and the PK result was in line with the pharmacokinetic characteristics.

Phoenix Winnolin 8.0 software was used to establish a model for Non-Compartmental Analysis (NCA) to calculate the PK parameters including: half-life ($T_{1/2}$); drug peak concentration ($C_{max}$); peak time ($T_{max}$); area under the blood drug concentration-time curve from Day 0 to Day 24 ($AUC_{0-24}$); area under the blood drug concentration-time curve from the start of administration (Day 0) to theoretical extrapolation ($AUC_{0-inf}$); apparent volume of distribution ($V_z$); clearance rate (Cl); and steady-state apparent volume of distribution ($V_{ss}$). The table below shows the overall pharmacokinetic parameters of hIgG in mice of the four groups (G1, G2, G3, and G4).

TABLE 11

Overall pharmacokinetic parameters

| Group | $T_{1/2}$ (day) | $T_{max}$ (day) | $C_{max}$ (ng/mL) | $AUC_{0-24}$ (day*ng/mL) | $AUC_{0-obs}$ (day*ng/mL) | Vz (mL/kg) | Cl (mL/day/kg) | Vss (mL/kg) |
|---|---|---|---|---|---|---|---|---|
| G1 | 11.19 | 0.01 | 31.71 | 72.76 | 82.72 | 1951.36 | 120.89 | 801.03 |
| G2 | 0.26 | 0.01 | 48.04 | 15.66 | 16.77 | 221.49 | 596.36 | 172.04 |
| G3 | 5.37 | 0.01 | 34.5 | 47.82 | 49.54 | 1565.25 | 201.86 | 653.94 |
| G4 | 4.34 | 0.01 | 37.12 | 116.61 | 118.46 | 528.96 | 84.42 | 307.46 |

The average half-lives of hIgG in B-NDG mice, BNDG B2M-KO mice, BNDG-B2M/FcRn mice, and wild-type C57BL/6 mice were 11.19 days, 0.26 days, 5.37 days, and 4.34 days, respectively. Since immune-mediated elimination of hIgG is impaired in B-NDG mice, the half-life of hIgG in B-NDG mice (11.19 days) was longer than that of wild-type C57BL/6 mice (4.34 days). The reason for the shorter hIgG half-life in BNDG-B2M-KO mice (0.26 days) was likely due to the knockout of the B2M gene. When the B2M nucleotide sequence was inserted into the FcRn locus (in BNDG-B2M/FcRn mice), the half-life of hIgG was partially restored (5.37 days).

Example 5. Immune Reconstitution in BNDG-B2M/FcRn Mice

The BNDG-B2M/FcRn mice obtained by the method described herein can be transplanted with human peripheral blood cells (hPBMC) or artificial hematopoietic stem cells to construct a mouse model of human immune system.

Figure 14:
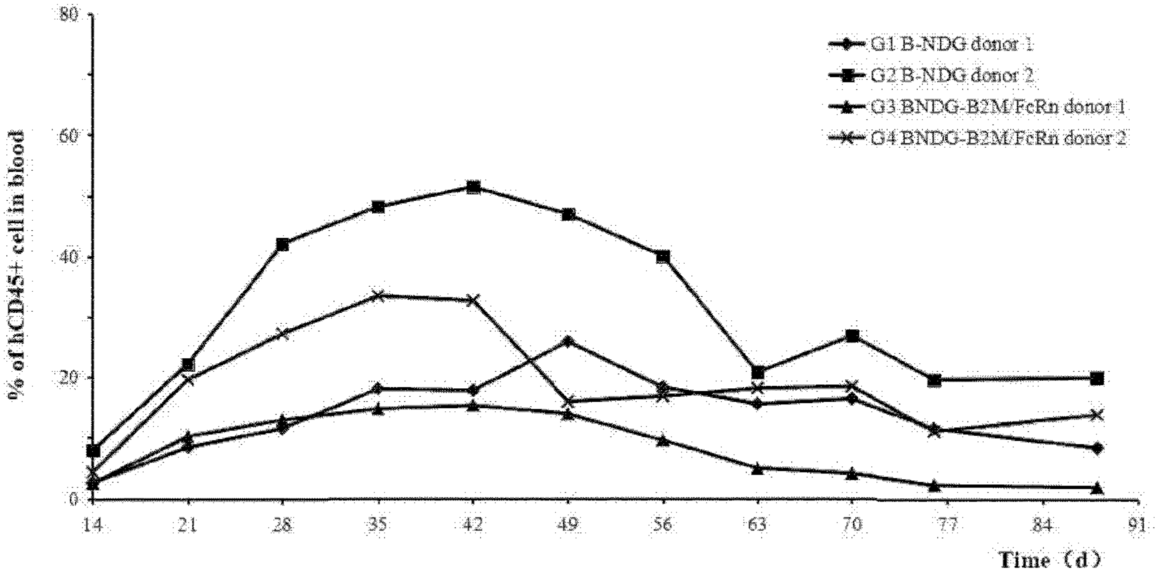
FIG. 14 shows the percentage curve of human leukocytes (hCD45+ cells) in the blood from immune reconstituted B-NDG mice that were injected with hPBMC from donor 1 (G1) or donor 2 (G2); or from immune reconstituted BNDG-B2M/FcRn mice that were injected with hPBMC from donor 1 (G3) or donor 2 (G4).

In one example, hPBMC was used for human immune system reconstitution. Specifically, 7-week-old female B-NDG mice and BNDG-B2M/FcRn homozygous mice were selected (12 mice each) and placed into 4 groups according to body weight. The specific grouping and the amount of inoculated cells are shown in the table below. $5\times10^6$ cells of hPBMC from 2 donors (donor 1 and donor 2) were injected via tail, and blood was drawn after 2 weeks for flow cytometry detection. As shown in FIG. 14, after hPBMC injection, cells expressing human leukocyte surface marker (CD45+) were detected in all B-NDG mice and BNDG-B2M/FcRn homozygous mice.

TABLE 12

Grouping and cell inoculation amount

| Group | Animal | Number | Donor | amount of inoculated cells | Volume of inoculated cells |
|---|---|---|---|---|---|
| G1 | B-NDG | 6 | Donor 1 | $5 \times 10^6$/mouse | 0.2 ml/mouse |
| G2 | B-NDG | 6 | Donor 2 | $5 \times 10^6$/mouse | 0.2 ml/mouse |
| G3 | BNDG-B2M/FcRn | 6 | Donor 1 | $5 \times 10^6$/mouse | 0.2 ml/mouse |
| G4 | BNDG-B2M/FcRn | 6 | Donor 2 | $5 \times 10^6$/mouse | 0.2 ml/mouse |

Figure 15:
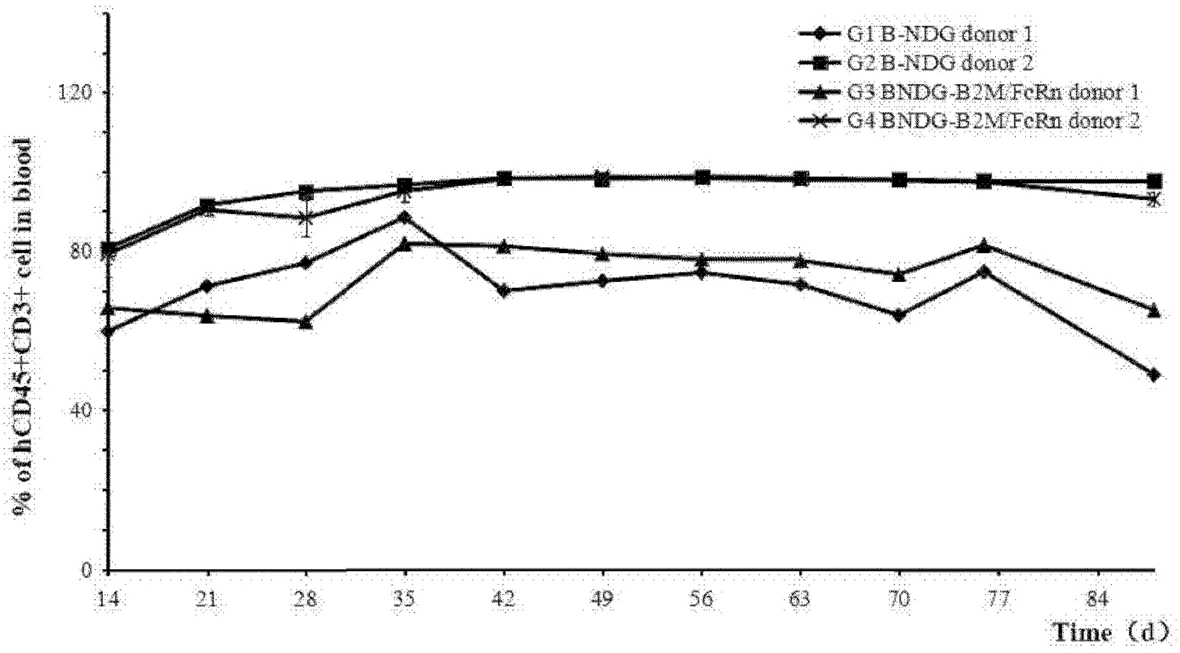
FIG. 15 shows the percentage curve of human T cells (hCD45+CD3+ cells) in leukocytes (hCD45+ cells) from immune reconstituted B-NDG mice that were injected with hPBMC from donor 1 (G1) or donor 2 (G2); or from immune reconstituted BNDG-B2M/FcRn mice that were injected with hPBMC from donor 1 (G3) or donor 2 (G4).

Further analysis found that the reconstitution of peripheral blood cells was mainly T cells. The results of T cell detection in mice in the 4 groups are shown in FIG. 15. After the immune reconstitution, the number of T cells in mice exhibited a correlation with the source of the donor. After the immune reconstitution using hPBMC from donor 2, the number of T cells in both B-NDG mice and BNDG-B2M/FcRn mice were higher as compared to mice injected with hPBMC from donor 1.

Figure 16:
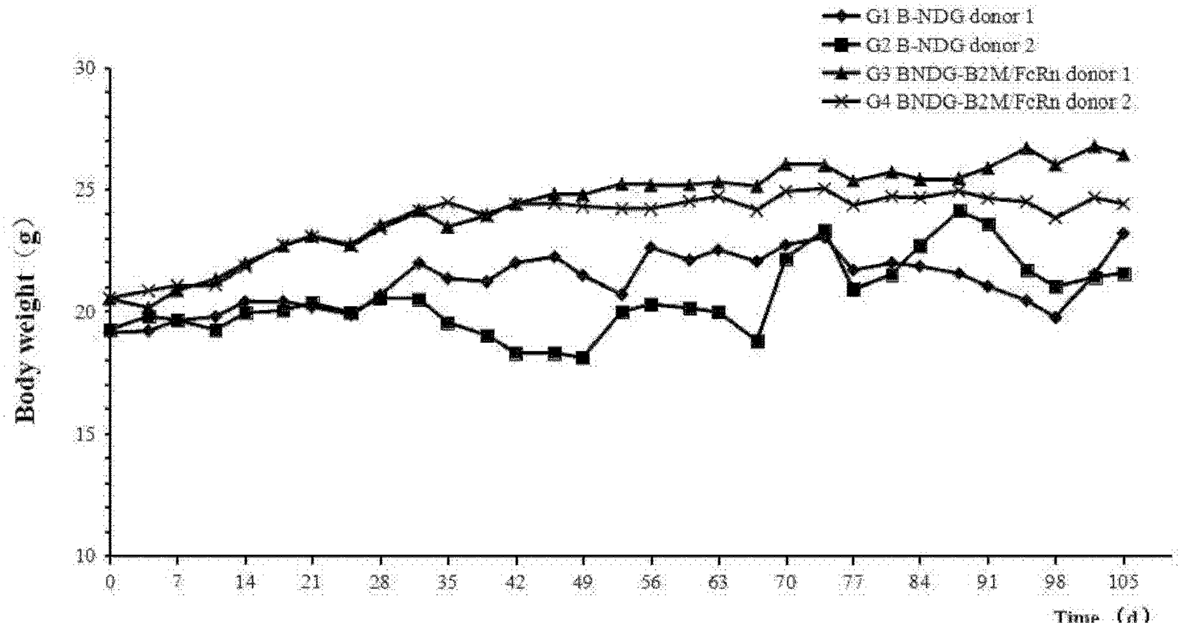
FIG. 16 shows the body weight of immune reconstituted B-NDG mice that were injected with hPBMC from donor 1 (G1) or donor 2 (G2); or immune reconstituted BNDG-B2M/FcRn mice that were injected with hPBMC from donor 1 (G3) or donor 2 (G4).

The body weight changes of the 4 groups of mice are shown in FIG. 16. After injection of two different sources of hPBMC, the body weight of BNDG-B2M/FcRn mice gradually increased, and the overall trend was increasing. After B-NDG mice were injected with two different sources of hPBMC, the body weight showed slight fluctuations, but the overall trend was increasing. The results showed that hPBMC immune reconstitution did not affect the weight gain of BNDG-B2M/FcRn mice and B-NDG mice. Moreover, compared with B-NDG mice, BNDG-B2M/FcRn mice gained body weight more stably after hPBMC immune reconstitution, indicating that a mouse model of hPBMC immune reconstitution was successfully constructed.

Figure 17:
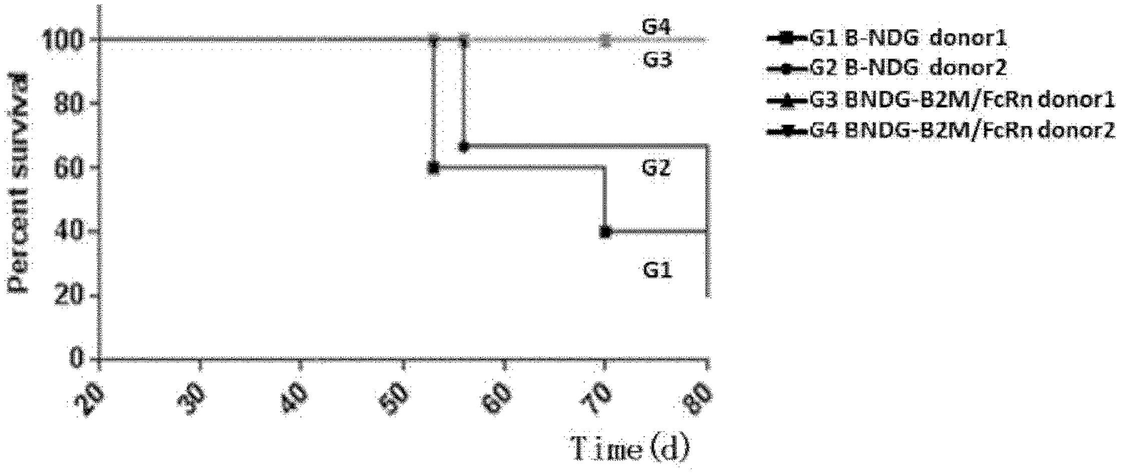
FIG. 17 shows the survival curve of immune reconstituted B-NDG mice that were injected with hPBMC from donor 1 (G1) or donor 2 (G2); or immune reconstituted BNDG-B2M/FcRn mice that were injected with hPBMC from donor 1 (G3) or donor 2 (G4).

The statistical results of the mouse survival rate (after the injection of hPBMC) in each group are shown in FIG. 17. The survival period of both B-NDG mice and BNDG-B2M/FcRn mice exceeded 80 days. Compared with B-NDG mice, BNDG-B2M/FcRn mice showed a higher survival rate, reaching 100%. Thus, the BNDG-B2M/FcRn mice can provide a longer experimental window for subsequent drug screening and evaluation.

In conclusion, the results indicate that BNDG-B2M/FcRn mice are more suitable for hPBMC immune reconstitution as compared to B-NDG mice.

Figure 18:
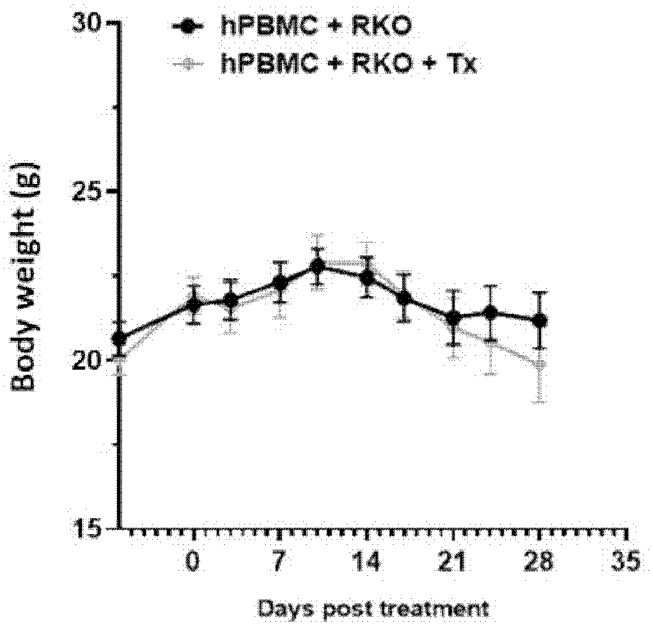
FIG. 18 shows the body weight of immune reconstituted BNDG-B2M/FcRn mice that were xenografted with human colon cancer cells RKO, and then treated with anti-human PD-1 monoclonal antibodies pembrolizumab and ipilimumab (hPBMC+RKO+Tx). Immune reconstituted BNDG-B2M/FcRn mice that were xenografted with human colon cancer cells RKO without antibody treatment (hPBMC+RKO) were used as a control.
Figure 19:
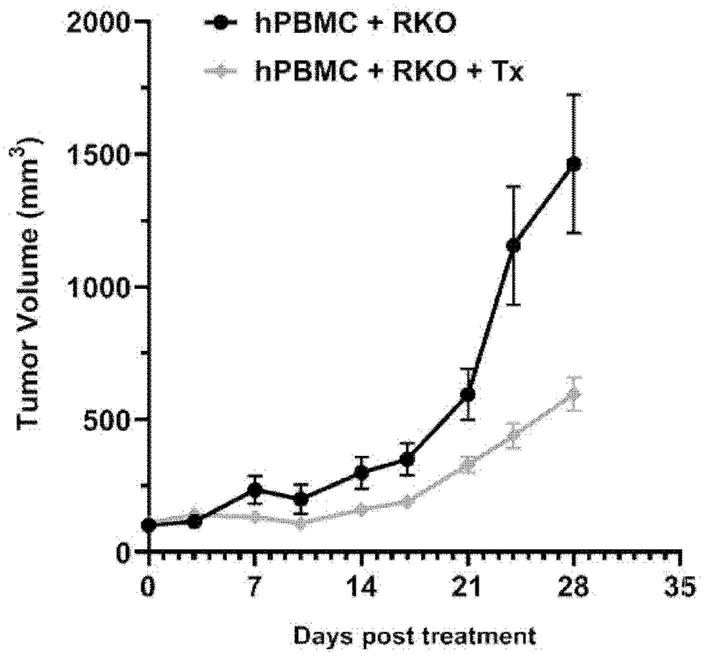
FIG. 19 shows the tumor volume of immune reconstituted BNDG-B2M/FcRn mice that were xenografted with human colon cancer cells RKO, and then treated with anti-human PD-1 monoclonal antibodies pembrolizumab and ipilimumab (hPBMC+RKO+Tx). Immune reconstituted BNDG-B2M/FcRn mice that were xenografted with human colon cancer cells RKO without antibody treatment (hPBMC+RKO) were used as a control.

Example 6. Drug Efficacy Verification in BNDG-B2M/FcRn Immune Reconstituted Xenograft Tumor Model The reconstituted BNDG-B2M/FcRn mice can be used to establish xenograft tumor models, which can be widely used for drug screening, pharmacodynamic research, etc., to improve the clinical conversion rate of drugs. Specifically, 15 BNDG-B2M/FcRn mice were subjected to hPBMC immune reconstitution, and 14 days later, human colon cancer cells RKO were subcutaneously inoculated. After 6 days (when tumor volume reached about 100 $mm^3$), the 15 mice were placed into a control group (hPBMC+RKO; 7 mice) and a treatment group (hPBMC+RKO+Tx; 8 mice) according to the tumor volume. The treatment group mice were administered with anti-human PD-1 monoclonal antibodies pembrolizumab and ipilimumab (obtained by immunizing mice, See Murphy, et al., *Janeway's immunobiology*. Garland Science, 2016 (9th edition)). The dose level was 200 μg/mouse/antibody and the antibodies were administered by intraperitoneal injection (i.p.) twice a week for a total of 8 administrations. The tumor volume was measured twice a week. The mouse body weight and tumor volume measurement results during the experimental period are shown in FIG. 18 and FIG. 19, respectively.

The table below lists the data and analysis results of each experiment, including tumor volume at the time of grouping (Day 0), 14 days after grouping (Day 14), 21 days after grouping (Day 21), or at the end of the experimental period (Day 28); the number of survived mice on Day 28; the number of tumor-free mice on Day 28; the tumor growth inhibition value based on tumor volume ($TGI_{TV}$ or $TGI_{TV}$ %); and the statistical difference (P value) of the tumor volume between the treatment group and the control group.

TABLE 13

Tumor volume, mouse survival, $TGI_{TV}$

| Group | Tumor volume ($mm^3$) Day 0 | Day 14 | Day 21 | Day 28 | Survived mice on Day 28 | Tumor-free mice on Day 28 | $TGI_{TV}$% | Tumor volume P value |
|---|---|---|---|---|---|---|---|---|
| Control | 102 ± 14 | 300 ± 60 | 595 ± 97 | 1464 ± 260 | 7/7 | 0/7 | N/A | N/A |
| Treatment | 111 ± 18 | 162 ± 6 | 331 ± 30 | 595 ± 64 | 8/8 | 0/8 | 64.46% | 0.004 |

All mice in the control group and the treatment group survived at the end of the experiment. Tumors in all control group mice continued to grow during the experimental period. At the end of the experimental period, the average tumor volume of the control group mice and the treatment group mice were 1464±260 $mm^3$ and 595±64 $mm^3$, respectively. Compared with the tumor volume of the control group mice, there was a significant difference (P≤0.05) (FIG. 19), and $TGI_{TV}$ reached 64.46% in the treatment group mice. The results indicate that the anti-human PD-1 monoclonal antibodies exhibited an inhibitory effect of tumor growth. The results also indicate that the BNDG-B2M/FcRn immune reconstitution xenograft tumor model prepared by the method described herein can be used for antibody screening and in vivo drug efficacy testing, and can also be used as a living substitute model for in vivo research for screening, evaluation and treatment of immuno-modulators.

Figure 20:
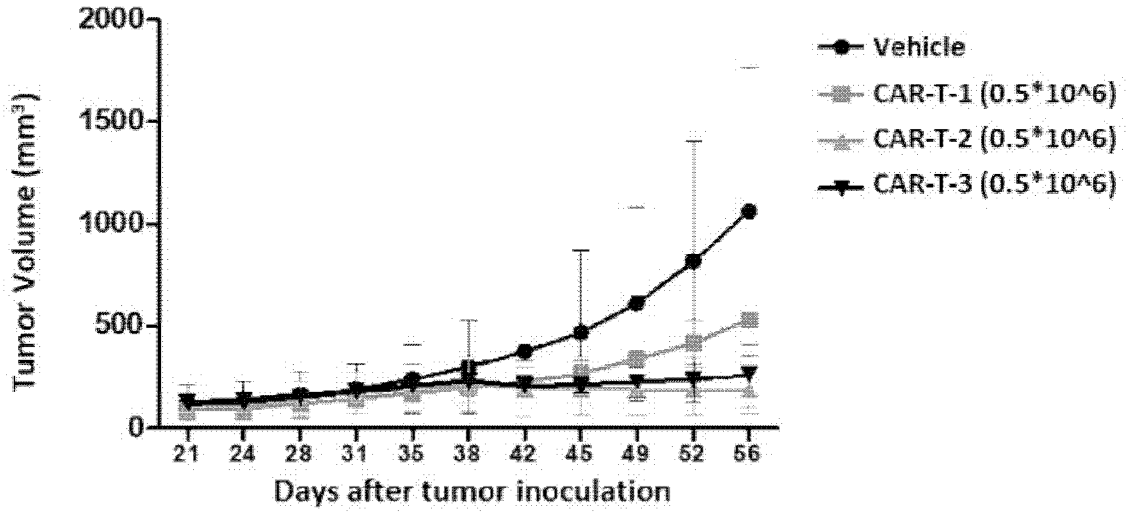
FIG. 20 shows the tumor volume of immune reconstituted BNDG-B2M/FcRn mice that were xenografted with human lung squamous cell carcinoma cells NCI-H226, and then treated with a CAR-T product (CAR-T-1, CAR-T-2, or CAR-T-3). Immune reconstituted BNDG-B2M/FcRn mice that were xenografted with NCI-H226 cells and then treated with T cells transduced with an empty vehicle (Vehicle) were used as a control.
Figure 21:
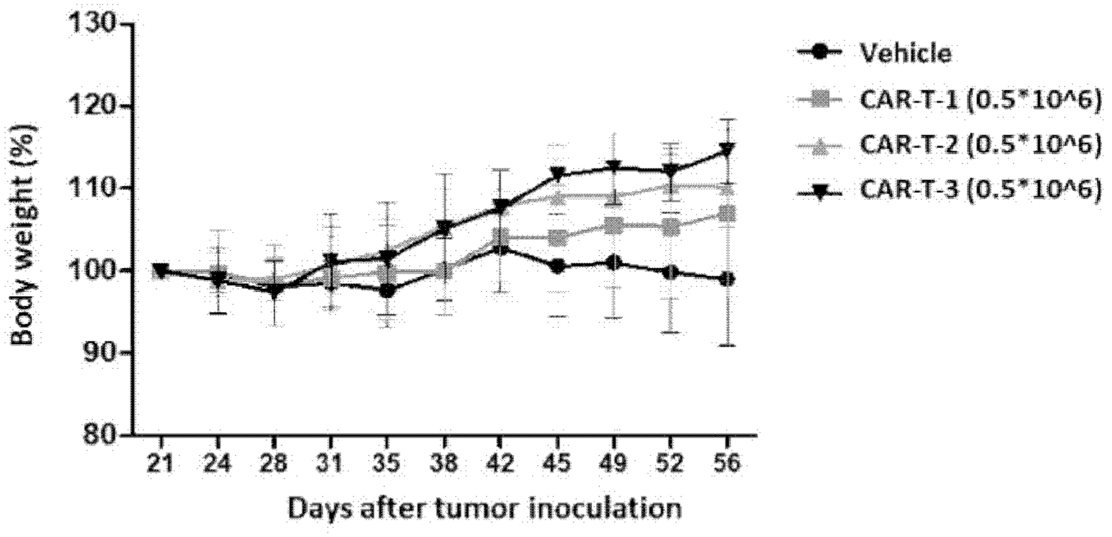
FIG. 21 shows the body weight of immune reconstituted BNDG-B2M/FcRn mice that were xenografted with human lung squamous cell carcinoma cells NCI-H226, and then treated with a CAR-T product (CAR-T-1, CAR-T-2, or CAR-T-3). Immune reconstituted BNDG-B2M/FcRn mice that were xenografted with NCI-H226 cells and then treated with T cells transduced with an empty vehicle (Vehicle) were used as a control.

Example 7. Drug Efficacy Verification in BNDG-B2M/FcRn Immune Reconstituted Xenograft Tumor Model for CAR-T The BNDG-B2M/FcRn immune reconstituted xenograft tumor model can also be used to verify the efficacy of CAR-T. Specifically, human lung squamous cell carcinoma cells NCI-H226 were subcutaneously transplanted into BNDG-B2M/FcRn mice with successful immune reconstitution of hPBMC. When tumor volume reached about 150±50 $mm^3$, the mice were placed into a control group (vehicle) and three treatment group (CAR-T-1, CAR-T-2, and CAR-T-3). The treatment group mice were administered with $5\times10^6$ CAR-T products. The mouse body weight and tumor volume measurement results during the experimental period are shown in FIG. 20 and FIG. 21, respectively.

Overall, Animals in each group were in good health during the experimental period. At the end of the experiment, the body weight of each group of mice fluctuated slightly, but the overall trend was normal. Compared with the control group mice, all treatment group mice showed no significant differences in body weight (FIG. 21), indicating that the animals tolerated the treatment well. According to the results of tumor volume (FIG. 20), compared with the control group mice, the tumor volume of the treatment group mice was significantly reduced, indicating that the three CAR-T products all exhibited different degrees of tumor cell clearance capabilities. In particular, the tumor clearance ability of CAR-T-2 was significantly higher than that of CAR-T-1 or CAR-T-3. The results indicate that the BNDG-B2M/FcRn immune reconstitution xenograft tumor model prepared by the method described herein can be used for the drug efficacy detection of CAR-T products, and can also be used as a living substitute model for in vivo research for the screening, evaluation and treatment of immuno-modulators.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A genetically-modified rodent expressing a fusion protein comprising a β2 microglobulin (B2M) and a neonatal Fc receptor (FcRn); wherein the FcRn comprises an extracellular region, a transmembrane region, and a cytoplasmic region.

2. The rodent of claim 1, wherein the genome of the rodent comprises at least one chromosome comprising a sequence encoding the fusion protein.

3. The rodent of claim 2, wherein the sequence encoding the fusion protein is operably linked to an endogenous regulatory element at an endogenous FcRn gene locus or an endogenous B2M locus in the at least one chromosome.

4. The rodent of claim 1, wherein the fusion protein comprises an endogenous B2M and an endogenous FcRn.

5. The rodent of claim 1, wherein the fusion protein comprises:

(a) a signal peptide of an endogenous FcRn;

(b) an endogenous B2M without a signal peptide; and (c) an endogenous FcRn without a signal peptide.

6. The rodent of claim 1, wherein the B2M comprises an amino acid sequence that is at least 70% identical to amino acids 21-119 of SEQ ID NO: 2.

7. The rodent of claim 1, wherein the FcRn comprises an amino acid sequence that is at least 70% identical to amino acids 22-365 of SEQ ID NO: 4.

8. The rodent of claim 1, wherein the fusion protein comprises an amino acid sequence that is at least 70% identical to SEQ ID NO: 6.

9. The rodent of claim 1, wherein the rodent is heterozygous or homozygous with respect to the sequence encoding the fusion protein.

10. The rodent of claim 1, wherein the rodent does not express endogenous B2M or endogenous FcRn.

11. The rodent of claim 1, wherein the B2M and FcRn can-associate with each other, forming a functional FcRn protein complex.

12. The rodent of claim 1, wherein the rodent is an immunodeficient mouse.

13. The rodent of claim 1, wherein the genome of the rodent comprises a disruption in the rodent's endogenous CD132 gene.

14. The rodent of claim 1, wherein the rodent further comprises a sequence encoding an additional human or chimeric protein.

15. A method of determining effectiveness of an agent or a combination of agents for the treatment of cancer, comprising:

(a) engrafting tumor cells to the rodent of claim 1, thereby forming one or more tumors in the rodent;

(b) administering the agent or the combination of agents to the rodent; and (c) determining inhibitory effects on the tumors.

16. The method of claim 15, wherein the agent is an antibody or antigen-binding fragment thereof, a chimeric antigen receptor (CAR), a T cell receptor (TCR), or an antigen-binding fragment thereof.

17. A method of producing a rodent comprising a human hemato-lymphoid system, the method comprising:

engrafting a population of cells comprising human hematopoietic cells or human peripheral blood cells into the rodent of claim 1.

* * * * *